(12) United States Patent
Guss et al.

(10) Patent No.: US 9,795,664 B2
(45) Date of Patent: Oct. 24, 2017

(54) VACCINE AGAINST STREPTOCOCCAL INFECTIONS BASED ON RECOMBINANT PROTEINS

(71) Applicant: Intervacc AB, Hagersten (SE)

(72) Inventors: Bengt Guss, Uppsala (SE);
Jan-Ingmar Flock, Bromma (SE);
Lars Frykberg, Storvreta (SE);
Margareta Flock, Bromma (SE)

(73) Assignee: Intervacc AB, Hagersten (SE)

( * ) Notice: Subject to any disclaimer, the term of this patent is extended or adjusted under 35 U.S.C. 154(b) by 0 days.

(21) Appl. No.: 14/959,672

(22) Filed: Dec. 4, 2015

(65) Prior Publication Data
US 2016/0082096 A1    Mar. 24, 2016

Related U.S. Application Data

(62) Division of application No. 13/683,522, filed as application No. PCT/SE2011/050652 on May 25, 2011, now Pat. No. 9,333,252.

(60) Provisional application No. 61/348,376, filed on May 26, 2010.

(51) Int. Cl.
| | |
|---|---|
| *A61K 39/09* | (2006.01) |
| *C07K 14/315* | (2006.01) |
| *C07K 16/12* | (2006.01) |
| *A61K 31/7088* | (2006.01) |
| *A61K 39/40* | (2006.01) |
| *C07K 19/00* | (2006.01) |
| *A61K 39/00* | (2006.01) |

(52) U.S. Cl.
CPC ........ *A61K 39/092* (2013.01); *A61K 31/7088* (2013.01); *A61K 39/40* (2013.01); *C07K 14/315* (2013.01); *C07K 16/1275* (2013.01); *C07K 19/00* (2013.01); *A61K 2039/543* (2013.01); *A61K 2039/552* (2013.01)

(58) Field of Classification Search
None
See application file for complete search history.

(56) References Cited

U.S. PATENT DOCUMENTS 5,583,014 A    12/1996    Brown et al.

FOREIGN PATENT DOCUMENTS

| WO | 8700436 | 1/1987 |
|---|---|---|
| WO | 9507296 | 3/1995 |
| WO | 9801561 | 1/1998 |
| WO | 0037496 | 6/2000 |
| WO | 2004032957 A1 | 4/2004 |
| WO | 2007115059 A2 | 10/2007 |
| WO | 2008071418 A2 | 6/2008 |
| WO | 2009033670 A2 | 3/2009 |
| WO | 2009075646 A1 | 6/2009 |
| WO | 2009093014 A2 | 7/2009 |
| WO | 2011059385 A1 | 5/2011 |

OTHER PUBLICATIONS

Albert, et al. "In vivo enzymatic modulation of IgG glycosylation inhibits autoimmune disease in an IgG subclass-dependent manner" PNAS; Sep. 30, 2008; vol. 105; No. 39; pp. 15005-15009.
Allhorn, et al. "Sugar-free Antibodies—The Bacterial Solution to Autoimmunity?" Contemporary Challenges in Autoimmunity; 2009; vol. 1173; pp. 664-669.
Allhorn, et al. "Human IgG/Fc_R Interactions are Modulated by Streptococcal IgG Glycan Hydrolysis" PLoS One; Jan. 2008; Issue 1; pp. 1-12.
Allhorn, et al. "EndoS from *Streptococcus pyogenes* is hydrolyzed by the cysteine proteinase SpeB and requires glutamic acid 235 and tryptophans for IgG glycan-hydrolyzing activity" BMC Microbiology; Jan. 8, 2008; vol. 8; No. 3; pp. 1-10.
Barnham, et al. "Human infection with *Streptococcus zooepidemicus* (Lancefield group C): three case reports" Epidem. Inf; 1987; vol. 98; pp. 183-190.
Bisno, et al. "Molecular basis of group A streptococcal virulence" The Lancet Infectious Disease; Apr. 2003; vol. 3; pp. 191-200.
Chhatwal, et al. "Uncovering the mysteries of invasive streptococcal diseases" Trends in Molecular Medicine; Apr. 2005; vol. 11; No. 4; pp. 152-155.
Collin, et al. "EndoS, a novel secreted protein from *Streptococcus pyogenes* with endoglycosidase activity on human IgG" The EMBO Journal; 2001; vol. 20; No. 12; pp. 3046-3055.
Collin, et al. "Extracellular Enzymes with Immunomodulating Activities: Variations on a Theme in *Streptococcus pyogenes*" Infection and Immunity; Jun. 2003; vol. 71; No. 6; pp. 2983-2992.
Fernandez, et al, "*Streptococcus equi* subsp. *ruminatorum* subsp. nov., isolated from mastitis in small ruminants" International Journal of Systematic and Evolutionary Microbiology; 2004; vol. 54; pp. 2291-2296.
Flock, et al. "Recombinant *Streptococcus equi* Proteins Protect Mice in Challenge Experiments and Induce Immune Response in Horses" Infection and Immunity; Jun. 2004; vol. 72; No. 6; pp. 3228-3236.
Flock, et al. "Protective effect of vaccination with recombinant proteins from *Streptococcus equi* subspecies *equi* in a strangles model in the mouse" Vaccine: 2006; vol. 24; pp. 4144-4151.

(Continued)

*Primary Examiner* — Brian J Gangle
(74) *Attorney, Agent, or Firm* — Pierce Atwood LLP; Kevin M. Ferrell; David J. Wilson

(57) ABSTRACT

An antigenic composition comprises several antigenic components derived from antigens of *Streptococcus equi* subsp. *equi* or subsp. *zooepidemicus*, wherein at least one component is a fusion protein or polypeptide comprimising two or more such antigens or fragments thereof. The antigenic composition may be used for immunization of mammals against *S. equi* subsp. *equi* and/or subsp. *zooepidemicus*. A vaccine composition comprising the antigenic composition as immunizing component is also disclosed.

24 Claims, 7 Drawing Sheets

(56) References Cited

OTHER PUBLICATIONS

Guss, et al. "Protective vaccination in the horse against *Streptococcus equi* with recombinant antigens" Available from Nature Precedings; Mar. 26, 2009; <http://hdl.handle.net/10101/npre.2009.2985.1>; pp. 1-18.

Guss, et al. "Getting to Grips with Strangles: An Effective Multi-Component Recombinant Vaccine for the Protection of Horses from *Streptococcus equi* Infection" PLoS Pathogens; Sep. 2009; vol. 5; Issue 9; pp. 1-9.

Holden, et al. "Genomic Evidence for the Evolution of *Streptococcus equi*: Host Restriction, Increased Virulence, and Genetic Exchange with Human Pathogens" PLoS Pathogens; Mar. 2009; vol. 5; Issue 3; pp. 1-14.

Hulting, et al. "Two novel IgG endopeptidases of *Streptococcus equi*" FEMS; 2009; vol. 298; pp. 44-50.

Jacobs, et al. "Investigations towards an efficacious and safe strangles vaccine: submucosal vaccination with a live attenuated *Streptococcus equi*" Veterinary Record; Nov. 11, 2000; vol. 147; pp. 563-567.

Jacobsson, et al. "Shot-gun phage display mapping of two streptococcal cell-surface proteins" Microbiological Research; 1997; vol. 152; pp. 121-128.

Janulczyk, et al. "Improved pattern for Genome-Based Screening Identifies Novel Cell Wall-Attached Proteins in Gram-Positive Bacteria" Infection and Immunity; Jun. 2001; vol. 69; No. 6; pp. 4019-4026.

Jonsson, et al. "A Protein G-Related Cell Surface Protein in *Streptococcus zooepidemicus*" Infection and Immunity; Aug. 1995; vol. 63; No. 8; pp. 2968-2975.

Karlstrom, et al. "Identification of a novel collagen-like protein, Sc1C, in *Streptococcus equi* using signal sequence phage display" Veterinary Microbiology; 2004; vol. 104; pp. 179-188.

Karlstrom, et al. "Sc1C is a member of a novel family of collagen-like proteins in *Streptococcus equi* subspecies *equi* that are recognized by antibodies against Sc1C" Veterinary Microbiology; 2006; vol. 114; pp. 72-81.

Kemp-Symonds, et al. "Modified live *Streptococcus equi* ('strangles') vaccination followed by clinically adverse reactions associated with bacterial replication" Equine Veterinary Journal; 2007; vol. 39; No. 3; pp. 284-286.

Lannergard "Potentially Virulence-Related Extracellular Proteins of *Streptococcus equi*" 2006; Doctoral thesis; Swedish University of Agricultural Sciences; pp. 1-46.

Lannergard, et al. "CNE, a collagen-binding protein of *Streptococcus equi*" FEMS Microbiology Letters; 2003; vol. 222; pp. 69-74.

Lannergard, et al. "IdeE, an IgG-endopeptidase of *Streptococcus equi* ssp. *equi*" FEMS Microbiology Letters; 2006; vol. 262; pp. 230-235.

Lindmark "Characterization of Adhesive Extracellular Proteins from *Streptococcus equi*" 1999; Doctoral Thesis; Swedish University of Agricultural Sciences; 61 pages.

Lindmark, et al. "SFS, a Novel Fibronectin-Binding Protein from *Streptococcus equi*, Inhibits the Binding between Fibronectin and Collagen" Infection and Immunity; May 1999; vol. 67; No. 5; pp. 2383-2388.

Lindmark, et al. "Fibronectin-Binding Protein of *Streptococcus equi* subsp. *zooepidemicus*" Infection and Immunity; Oct. 1996; vol. 64; No. 10; pp. 3993-3999.

Lindmark, et al. "Pulsed-field gel electrophoresis and distribution of the genes zag and fnz in isolates of *Streptococcus equi*" Research in Veterinary Science; 1999; vol. 66; pp. 93-99.

Lindmark et al. "Comparison of the Fibronectin-Binding Protein FNE from *Streptococcus equi* Subspecies *equi* with FNZ from *S. equi* Subspecies *zooepidemicus* Reveals a Major and Conserved Difference" Infection and Immunity; May 2001; vol. 69; No. 5; pp. 3159-3163.

Morein, et al. "Functional aspects of iscoms" Immunology and Cell Biology; 1998; vol. 76; pp. 295-299.

Nakata, et al. "Mode of Expression and Functional Characterization of FCT-3 Pilus Region-Encoded Proteins in *Streptococcus pyogenes* Serotype M49" Infection and Immunity; Jan. 2009; vol. 77; No. 1; pp. 32-44.

Nandakumar, et al. "Endoglycosidase treatment abrogates IgG arthritogenicity: Importance of IgG glycosylation in arthritis" European Journal of Immunology; 2007; vol. 37; pp. 2973-2982.

Newton, et al. "Investigation of suspected adverse reactions following strangles vaccination in horses" Veterinary Record; Feb. 26, 2005; pp. 291-292.

Rasmussen, et al. "Protein GRAB of *Streptococcus pyogenes* Regulates Proteolysis at the Bacterial Surface by Binding Alpha.sub.2-Macroglobulin" Journal of Biological Chemistry; May 28, 1999; vol. 274; No. 22; pp. 15336-15344.

Schneewind, et al. "Structure of the Cell Wall Anchor of Surface Proteins in *Staphylococcus aureus*" Science; Apr. 7, 1995; vol. 268; pp. 103-106.

Sutcliffe, et al. "Pattern searches for the identification of putative lipoprotein genes in Gram-positive bacterial genomes" Microbiology; 2002; vol. 148; pp. 2065-2077.

Sweeney, et al. "*Streptococcus equi* Infections in Horses: Guidelines for Treatment, Control, and Prevention of Strangles" Journal Veterinary Internal Medicine; 2005; vol. 19; pp. 123-134.

Timoney "The pathogenic equine streptococci" Veterinary Research; 2004; vol. 35; pp. 397-409.

Timoney, et al. "Early pathogenesis of equine *Streptococcus equi* infection (strangles)" Equine Veterinary Journal; 2008; vol. 40; No. 7; pp. 637-642.

Timoney, et al. "Vaccine potential of novel surface exposed and secreted proteins of *Streptococcus equi*" Vaccine; 2007; vol. 25; pp. 5583-5590.

Turner, et al. "Impact of immunization against SpyCEP during invasive disease with two streptococcal species: *Streptococcus pyogenes* and *Streptococcus equi*" Vaccine; 2009; vol. 27; pp. 4923-4929.

Walker, et al. "Construction of a stable non-mucoid deletion mutant of the *Streptococcus equi* Pinnacle vaccine strain" Veterinary Microbiology; 2002; vol. 89; pp. 311-321.

Waller, et al. "Vaccination of horses against strangles using recombinant antigen from *Streptococcus equi*" Vaccine; 2007; vol. 25; pp. 3629-3635.

Timoney, et al. Novel, Protectively Immunogenic, Surface Exposed, and Secreted Proteins of *Streptococcus equi*: Research Accomplishment Reports; 2009; last modified on May 10, 2010; 2 pages.

Weinreich Olsen, et al. "Protection of Mice with a Tuberculosis Subunit Vaccine Based on a Fusion Protein of Antigen 85B and ESAT-6" Infection and Immunity; May 2001; vol. 69; No. 5; pp. 2773-2778.

Zhang, et al. "Enhanced Immunogenicity of a Genetic Chimeric Protein Consisting of Two Virulence Antigens of *Streptococcus mutans* and Protection against Infection" Infection and Immunity; Dec. 2002; vol. 70; No. 12; pp. 6779-6787.

Waller, et al. "Getting a grip on strangles: Recent progress towards improved diagnostics and vaccines" The Veterinary Journal; 2007; vol. 173; pp. 492-501.

(Panels A, B and C)

(Panels D, E and F)

(Panels G and H)

FIG. 2

Post mortem values in combined studies I and II

Added PM values (y-axis: 0 to 70)

○ Strangvacc 2
□ Strangvacc 3/4
△ Strangvacc 5
◇ Strangvacc 7
◆ Strangvacc 8
● Placebo

VACCINE AGAINST STREPTOCOCCAL INFECTIONS BASED ON RECOMBINANT PROTEINS

SEQUENCE LISTING

The instant application contains a Sequence Listing which has been submitted electronically in ASCII format and is hereby incorporated by reference in its entirety. Said ASCII copy, created on Feb. 24, 2017, is named UPDATE~1.txt and is 77.2 KB in size.

FIELD OF THE INVENTION

This invention relates to subunit immunogenic or vaccine compositions and use thereof for immunization of mammals susceptible to streptococcal infections. The invention also relates to methods for preparing, formulating and administrating such compositions.

BACKGROUND OF THE INVENTION

Streptococcal infections in horses are mainly caused by the species *Streptococcus equi*, which comprises three subspecies designated *equi*, *zooepidemicus*, and *ruminatorium* respectively hereafter simply called *S. equi*, *S. zooepidemicus* and *S. ruminatorium* (Refs. 15, 24, 40).

*S. equi* which is virtually confined to horses is the causative agent of strangles, a world-wide distributed and highly contagious serious disease of the upper respiratory tract of the Equidae. Strangles is one of the most frequently reported equine diseases world-wide and is characterized by fever, nasal discharge, and abscess formation in the retropharyngeal and mandibular lymph nodes. In some cases the disease shows a metastatic course in the body, so called "bastard strangles". The disease has a world-wide distribution and causes great economic losses (Ref. 39).

*S. zooepidemicus* is considered as an opportunistic commensal often occurring in the upper respiratory tract of healthy horses. However, after stress or virus infection, it can cause a secondary infection, which results in strangles-like symptoms. Moreover, *S. zooepidenzicus* infects not only horses but also a wide range of other animals, like pigs, goats, dogs, cats, and cows. Even human cases of infection due to subsp. *zooepidemicus* have been reported (Ref. 5). This subspecies has been implicated as the primary pathogen in conditions such as endometritis, cervicitis, abortion, mastitis, pneumonia, abscesses and joint infections.

*S. ruminatorium* has been isolated from milk of sheep and goats with mastitis (Ref. 10).

*Streptococcus pyogenes* is an important human pathogen which causes a variety of diseases e.g. impetigo, pharyngitis, necrotizing fasciitis and toxic shock syndrome.

Although it is possible to treat and cure these streptococcal infections with antibiotics, such as penicillin, tetracycline or gentamicin, an effective prophylactic agent that could prevent outbursts of such infections and obviate or reduce the risk for development of resistant strains associated with antibiotic treatment, would be appreciated.

DESCRIPTION OF THE RELATED ART

However, although many attempts have been made to develop prophylactic agents such as vaccines against *S. equi*, at the present time no efficient and safe vaccines are available on the market, neither for the subsp. *equi* nor for the subsp. *zooepidemicus*, subsp. *ruminatorium* or *S. pyogenes*.

Existing vaccines against strangles are based on inactivated, e. g. heat-killed, or attenuated strains of *S. equi* or acid extracts/mutanolysin enriched in M-protein(s), i.e. immunogenic protein(s) produced by *S. equi*. A vaccine against *S. zooepidemicus* based on an M-like protein is disclosed in U.S. Pat. No. 5,583,014. In WO 87/00436, Ref. 17 and WO 2009/093014 A2 attenuated strains of *S. equi* are disclosed for use as a vaccine against infections caused by *S. equi*.

A commercial vaccine against strangles, Equilis StrepE from Intervet, UK, was released in 2004. However, the safety and efficacy of this vaccine, which is based on an attenuated (living, deletion mutated) strain of *S. equi* can be questioned (Refs. 23, 35).

Since the previously developed vaccines or immunizing preparations based on living or inactivated bacteria are hampered by side-effects and may provide insufficient protection there is a need for efficient and safe prophylactic agents, such as vaccines, that protect against *S. equi* infections and/or prevent spread thereof without giving rise to undesirable side-effects.

For years, streptococcal surface proteins, that interact with and/or bind to different components of the Extracellular Matrix (ECM) or plasma proteins of the host cell have been identified and characterized. Examples of extracellular surface proteins of *S. equi* and *S. zooepidemicus* that have been characterized are FNZ (Ref. 29), EAG (Ref. 27), the collagen-like proteins (SclC, SclD, SclE, SclF, SclG, SclH and SclI) (Refs. 21, 22), CNE (also called Sec) (Ref. 25), ZAG (Ref. 18 and WO 95/07296). Furthermore, examples of *S. equi* extracellular proteins that are supposed to be released into the surrounding medium are SFS (Ref. 28), IdeE and IdeZ (Ref. 26), IdeE2 and IdeZ2 (Ref. 16). These types of proteins are potential candidates for use as active component (s) for immunizing purposes.

The uses of this type of proteins as components in a potential vaccine for protection of horses against strangles are disclosed in WO 2004/032957 A1, WO 00/37496, WO 2007/115059 A2, WO 98/01561 and WO 2009/075646 A1.

In Flock, M., et al (2004) (Ref. 11), it is reported that in a mouse model of equine strangles, parts of the proteins designated FNZ, SFS and EAG, respectively, were used to immunize mice. FNZ and EAG were considered as promising candidates for development of a safe and efficacious vaccine against strangles.

Timoney et al (2007) (Ref. 42) reported that recombinant DNA produced extracellular proteins of subsp. *equi* are useless as vaccine components. It was speculated therein that earlier reported results for some *S. equi* proteins produced by recombinant DNA technology, showing protection in mice experiments, are not applicable to horses. Thus, it is not obvious that recombinant forms of extracellular localized *S. equi* proteins necessarily are functional as vaccine components.

In Ref. 45, vaccination of horses against strangles using the recombinant antigens EAG, CNE and SclC from *S. equi* is reported. In this study, vaccinated horses showed, after challenge with *S. equi*, significantly reduced recovery of bacteria and significantly lower levels of nasal discharge.

Although many efforts have been made to develop efficient vaccines and some of the immunizing components presented in Refs. 14 and 15, WO 2004/032957 A1, WO2009/075646 A1, are promising candidates for use in a vaccine that protects against *S. equi* infection, development of safe vaccines having a high degree of immunogenicity and exhibiting limited or no side effects is still desirable.

The human pathogen *Streptococcus pyogenes* also expresses a great number of extracellular proteins interacting with ECM and/or blood components of the host (Refs. 6, 7, 9, 33). Among these are an endoglycosidase, called EndoS that has the ability to hydrolyse the chitobiose core of the asparagine-linked glycan on human immunoglobulin G (IgG) (Ref. 8). EndoS has been further characterized in a series of articles, describing e.g. enzymatic properties, specificity etc (Refs. 1, 2, 3, 4, 34). The use of EndoS in treating or preventing diseases mediated by IgG antibodies such as autoimmune diseases is disclosed in WO/2008/071418 A2 and the in vitro use of EndoS to isolate and analyse IgG in WO 2009/033670 A2. The use of EndoSe of *Streptococcus equi* subsp. *equi* and EndoSz of *Streptococcus equi* subsp. *zooepidemicus*, or fragments thereof, as a component in a vaccine against bacterial infections or to elicit an immunogenic response or a protective immune response is disclosed in WO 2011/059385 A1 (the entire disclosure of which is incorporated by reference herein).

BRIEF SUMMARY OF THE INVENTION

The present invention is based on an antigenic, suitably an immunogenic, composition comprising multiple antigens, suitably immunogens that comprise at least one antigenic epitope or antigenic determinant derived from a protein present in one or both of *S. equi* and *S. zooepidemicus* and use thereof for immunization of non-human mammals against *S. equi* and/or *S. zooepidemicus*. According to the invention, at least one component of the composition is a fusion protein or polypeptide comprising two or more antigens or fragments thereof.

The present invention is also directed to a subunit immunogen or vaccine composition comprising the aforesaid antigenic composition as immunizing component; to methods to prepare said antigenic, suitably immunogenic, composition or vaccine composition; to methods to induce an immune response against *S. equi* and/or *S. zooepidemicus* in non-human mammals; and to methods for prophylactic or therapeutic treatment of *S. equi* and/or *S. zooepidemicus* infection in non-human mammals.

The invention is also directed to specific antigenic fusion polypeptides per se.

According to a suitable embodiment, the present invention is directed to a vaccine that protects equines, such as horses, against diseases caused by *S. equi*, e.g. strangles, upper respiratory tract infections, wound infections and endometritis. The word "protects" is a general term including anything between full protection and reduction of the severity of infection. The degree of protection can be measured in various ways, concerning e.g. *S. equi* infections in horses the effect of the vaccine can be reduced clinical symptoms and reduced clinical disease, where reduced increase in temperature, reduced swelling of lympnodes and reduced dissemination of bacteria from infected animals etc can be observed. Methods and procedures how to measure the efficacy of an immunizing composition after challenge can be obtained from e.g. Ref. 14, and WO 2009/075646 A1.

For various reasons, before performing vaccination and challenge experiments in horses, the evaluation of novel antigens to be used in a vaccine are studied in a small animal model. Concerning upper respiratory tract infections caused by subsp. *equi* a suitable and well established vaccination and experimental infection model has been described (Refs. 11, 12, 13, 14, 16, 43, WO 2004/032957 A1, WO 2009/075646 A1). This model has been used with a high degree of reliability to screen and evaluate *S. equi* antigens with a potential to provoke a protective immunogenic response in horses (Refs. 13, 14).

In the context of infections caused by *S. equi*, the expression "non-human mammals" primarily refers to animals belonging to the family Equidae that consists of horses, donkeys and zebras and to hybrids thereof, such as mules and hinnies. Camels and dromedaries are also encompassed therein.

In connection with infections caused by *S. zooepidemicus*, the expression "non-human mammals" in addition refers also to other mammals such as cows, pigs, dogs and cats.

The above-mentioned aspects of the invention, and preferred embodiments thereof, are defined in the appended claims.

In particular embodiments, the present invention makes use of one or more polypeptides selected from the amino acid sequences SEQ ID NOS: 22, 24, 26, 28, 30, 32, 34, 38, 42 and one or more nucleotide sequences selected from the nucleotide sequences SEQ ID NOS: 21, 23, 25, 27, 29, 31, 33, 37, 41.

The practice of the present invention will employ, unless otherwise indicated, conventional techniques of microbiology, recombinant DNA technology and molecular biology and immunology, which are within the skills of the art. Such techniques are explained in literature e.g. Sambrook et al (2001) Molecular Cloning: A laboratory manual, $3^{rd}$ ed. Cold Spring Harbour Press. Unless defined otherwise, all scientific and technical terms used herein have the same meaning as commonly understood by a person with ordinary skill in the art to which the invention pertains.

A "fragment" of a molecule such as a protein or nucleic acid is meant to refer to a portion of the amino acid or nucleotide sequence.

The term "analog" refers to a nucleic acid or amino acid sequence variant having a sequence homology ("identity") of 80% or more, especially 90% or more, with the reference sequence. In general, "identity" refers to an exact nucleotide to nucleotide or amino acid to amino acid correspondence of two polynucleotides or polypeptide sequences, respectively. Techniques for determining nucleic acid sequence identity are well known in the art, and software programs for calculating identity between sequences are available.

Many of the *S. equi* proteins have different designations in various reports. To facilitate the reading of this application to previous reports/patent applications references and alternative designation is shown in Table 1 below.

TABLE 1

| Present application | References | Alternative designation |
| --- | --- | --- |
| CNE | WO 2004/032957 A1, WO 2009/075646 A1 Ref. 25 | SEC |
| EAG | WO 2004/032957 A1, WO 2009/075646 A1 Ref. 11 | |
| Eq8 | WO 2009/075646 A1 Ref. 14 | SEQ0402 |
| Eq5 | WO 2009/075646 A1 Ref. 14 | SEQ0256 |
| A21 | Ref. 22 | SclF |
| A36 | Ref. 22 | SelI |
| A42 | WO 2004/032957 A1, WO 2009/075646 A1 Ref. 22 | SclC |
| IdeE | WO 2009/075646 A1 Refs. 16, 26 | |
| EndoSe | WO 2011/059385 A1 | |
| Eq54 | Ref. 14 | SEQ0939 |
| Eq27 | Ref. 14 | SEQ0944 |

BRIEF DESCRIPTION OF THE DRAWINGS

FIG. 2 is a diagram showing accumulated post mortem values for individual ponies vaccinated in Studies I and II.

DETAILED DESCRIPTION OF THE INVENTION

Figure 1A:
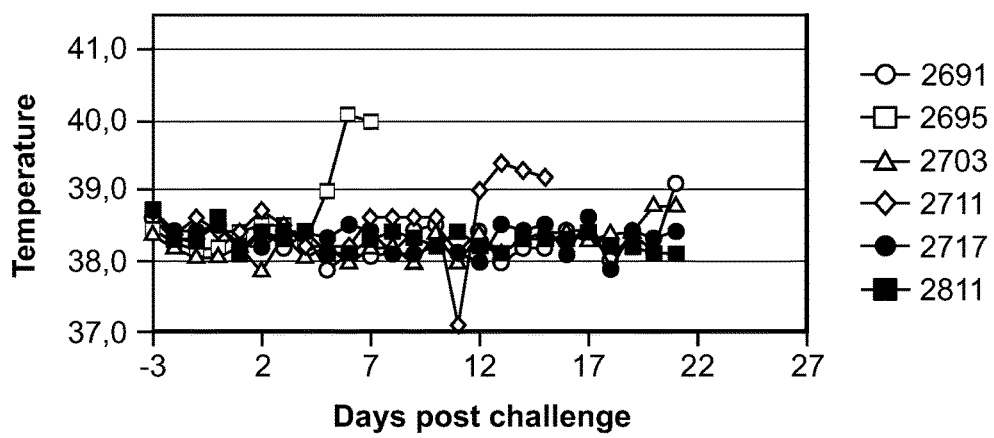
FIG. 1A is diagrams showing rectal temperature versus days post challenge in ponies vaccinated in Study I with Strangvacc 2, Strangvacc 3/4 or placebo for Panels A, B and C.
Figure 1A:
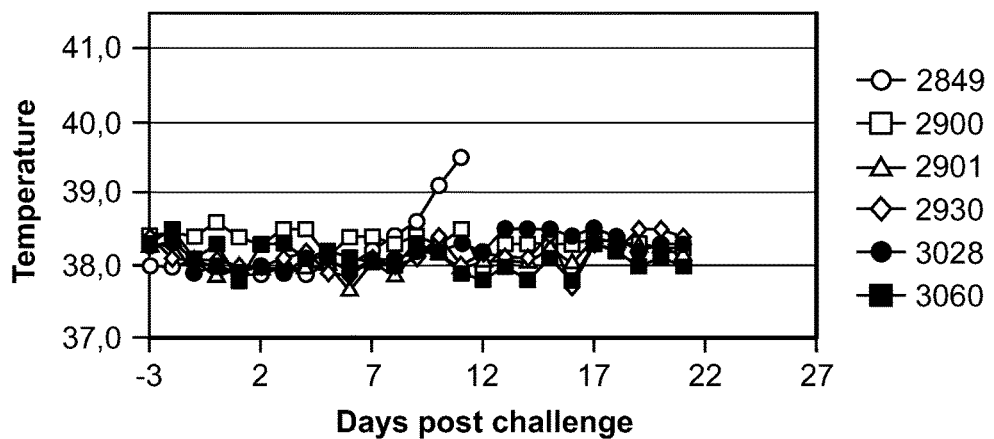
Figure 1A:
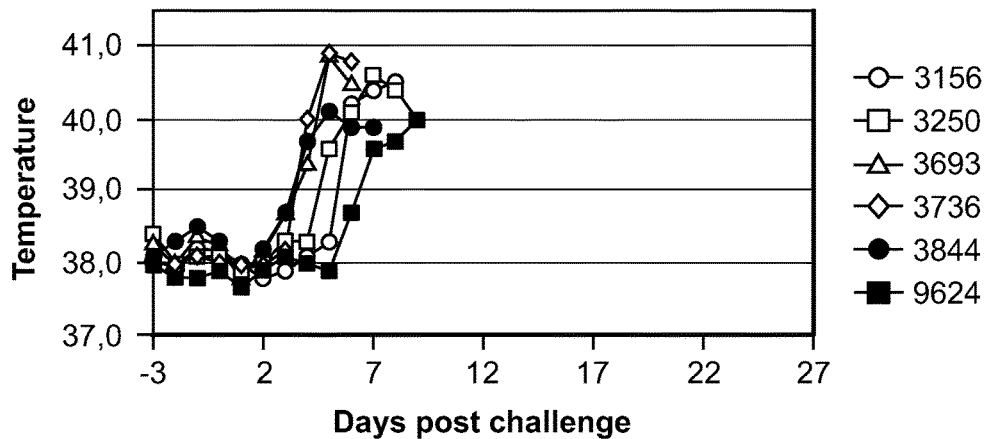
Figure 1B:
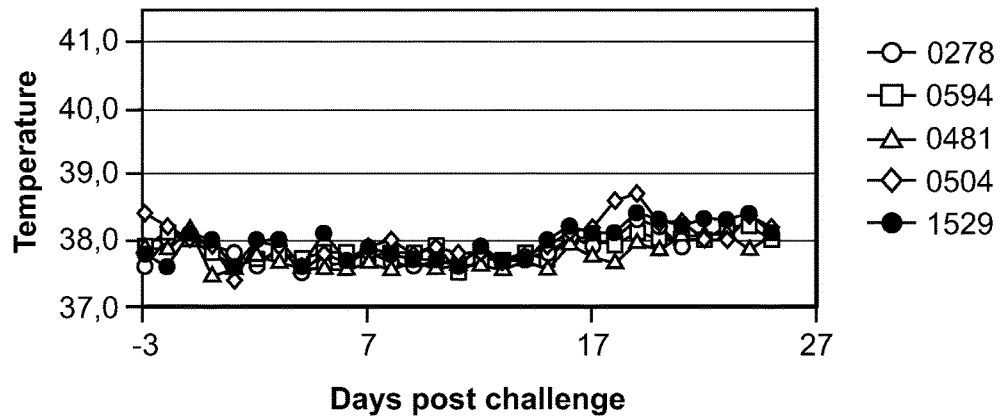
FIG. 1B is diagrams showing rectal temperature versus days post challenge in ponies vaccinated in Study II with Strangvacc 3/4, 5 or 7 for Panels D, E and F.
Figure 1B:
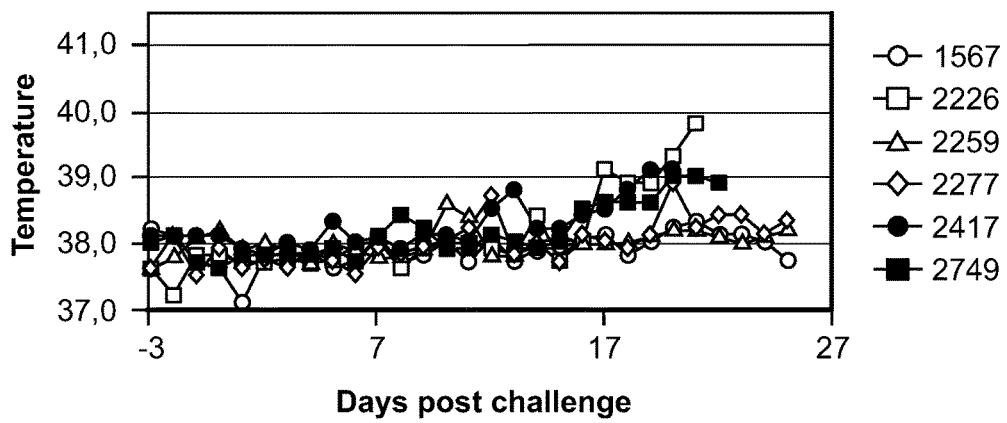
Figure 1B:
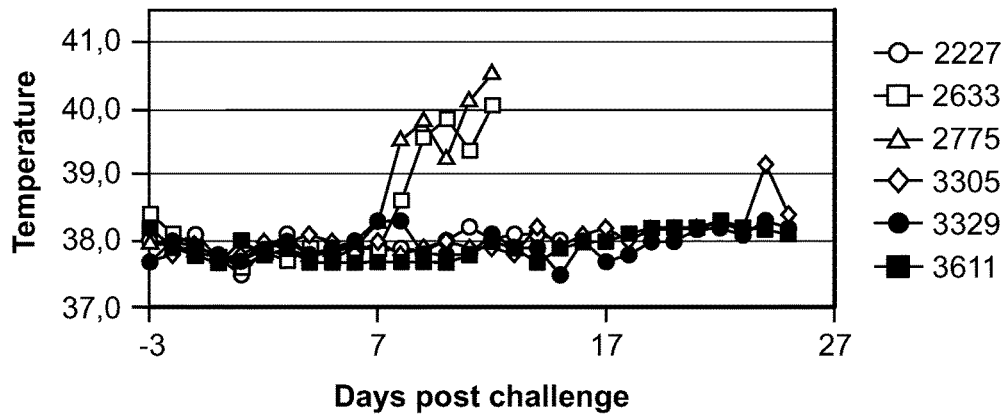
Figure 1C:
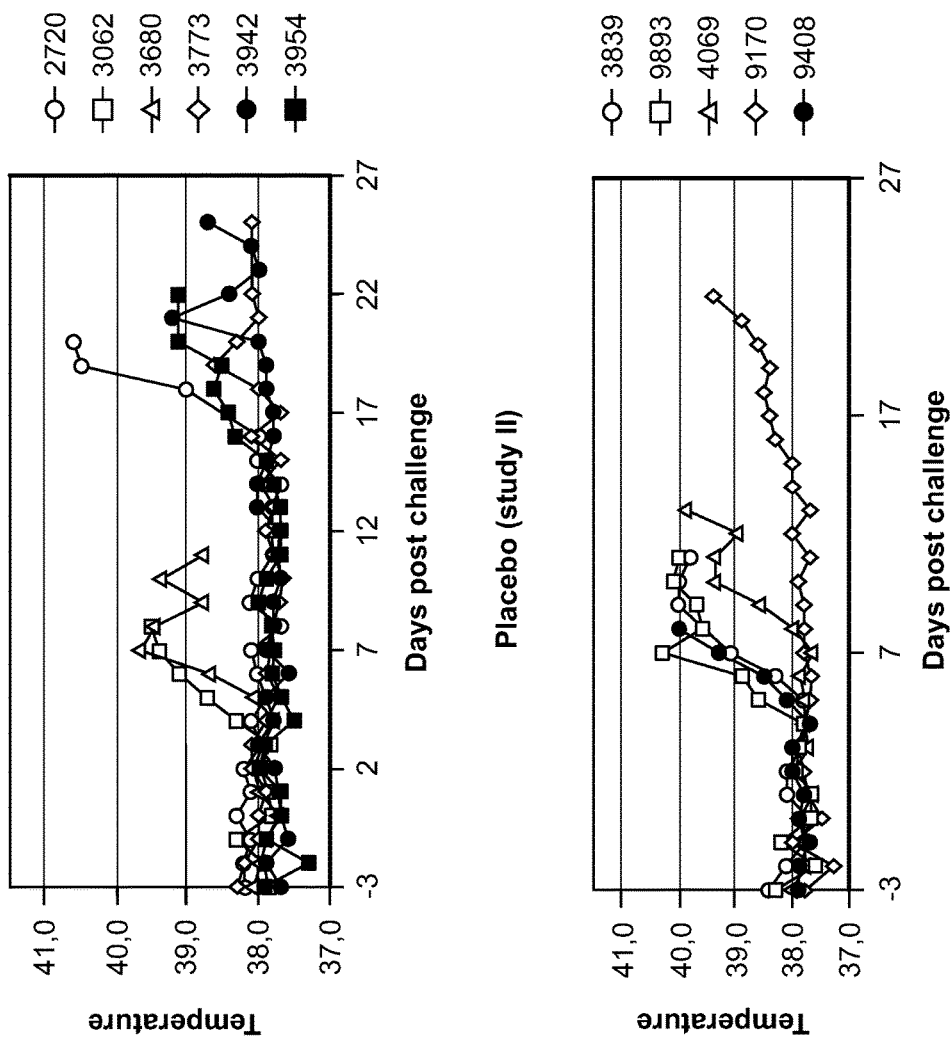
FIG. 1C is diagrams showing rectal temperature versus days post challenge in ponies vaccinated in Study II with Strangvacc 8 or placebo for Panels G and H.

As mentioned above, the present invention is generally concerned with identification of polypeptides or proteins of *S. equi* or *S. zooepidemicus* that are able to elicit an immunogenic response, when administered to a mammal; and to the identification of polynucleotides or genes encoding these polypeptides or proteins.

The present invention is also concerned with fragments or analogs of said polypeptides or proteins or of said polynucleotides or genes.

More specifically, the invention discloses how gene fragments of *S. equi* or *S. zooepidemicus* encoding various extracellular proteins can be combined by gene fusion technology, expressed in a suitable host and used as antigens in a vaccine against streptococcal infections in mammals. While based on such studies, the present invention is not limited to the specific combinations disclosed. Basically, the individual antigens represented in each fusion protein can be arranged in various number, order or combinations. In principal, an order of the antigens can e.g. be N-terminus-A-B-C-D-E-C-terminus, but the position of each individual antigen can be changed and the number thereof varied. Further, the invention also discloses how fusion proteins can be combined in a vaccine with non-fusion proteins to obtain efficient vaccine compositions.

In the following, reference will be made to various patent and literature references, the relevant disclosures of which are incorporated by reference herein.

According to one embodiment, the present invention is directed to an antigenic composition comprising several antigens, wherein each antigen comprises at least part of a protein or polypeptide of *S. equi* or *S. zooepidemicus*, and said at least part of said protein or polypeptide comprises at least one antigenic epitope or antigenic determinant of *S. equi* or *S. zooepidemicus*, and wherein said at least part of a protein or polypeptide is selected from the group comprising:

a protein or polypeptide which is designated Eq85 and has an amino acid sequence as shown in SEQ ID NO: 22;

a protein or polypeptide which is designated CCE and has an amino acid sequence as shown in SEQ ID NO: 24;

a protein or polypeptide which is designated IdcE and has an amino acid sequence as shown in SEQ ID NO: 26;

a protein or polypeptide which is designated CNEEAG and has an amino acid sequence as shown in SEQ ID NO: 28;

a protein or polypeptide which is designated IE5 and has an amino acid sequence as shown in SEQ ID NO: 30;

a protein or polypeptide which is designated EndoSe and has an amino acid sequence as shown in SEQ ID NO: 32;

a protein or polypeptide which is designated CPCE and has an amino acid sequence as shown in SEQ ID NO: 34;

a protein or polypeptide which is designated Eq54 and has an amino acid sequence as shown in SEQ ID NO: 38;

a protein or polypeptide which is designated Eq27 and has an amino acid sequence as shown in SEQ ID NO: 42;

and fragments and analogs thereof;

wherein at least one antigen is a fusion protein or polypeptide.

The above-mentioned antigen or antigens may further be combined with at least a part of a protein or polypeptide selected from the group comprising:

a protein or polypeptide which is designated CNE and has an amino acid sequence as shown in WO 2004/032957 A1, SEQ ID NO: 4;

a protein or polypeptide which is designated FNZ and has an amino acid sequence as shown in WO 2004/032957 A1, SEQ ID NO: 2;

a protein or polypeptide which is designated SFS and has an amino acid sequence as shown in WO 2004/032957 A1, SEQ ID NO: 3;

a protein or polypeptide which is designated SclC and has an amino acid sequence as shown in WO 2004/032957 A1, SEQ ID NO: 23;

a protein or polypeptide which is designated EAG and has an amino acid sequence as shown in WO 2004/032957 A1, SEQ ID NO: 1, and WO 2009/075646 A1, SEQ ID NO: 13;

a protein or polypeptide which is designated IdeE and has an amino acid sequence as shown in WO 2009/075646 A1, SEQ ID NO: 10;

a protein or polypeptide which is designated IdeE2 and has an amino acid sequence as shown in WO 2009/075646 A1, SEQ ID NO: 1;

a protein or polypeptide which is designated Eq5 and has an amino acid sequence as shown in WO 2009/075646 A1, SEQ ID NO: 3;

a protein or polypeptide which is designated Eq8 and has an amino acid sequence as shown in WO 2009/075646 A1, SEQ ID NO: 5;

a protein or polypeptide which is designated IdeZ2 and has an amino acid sequence as shown in WO 2009/075646 A1, SEQ ID NO: 7;

a protein or polypeptide which is designated Eqz5 and has an amino acid sequence as shown in WO 2009/075646 A1, SEQ ID NO: 8; and a protein or polypeptide which is designated Eqz8 and has an amino acid sequence as shown in WO 2009/075646 A1, SEQ ID NO: 9;

or an analog or a fragment thereof.

For convenience, the polypeptides having amino acid sequences as shown in the sequence listing of WO 2009/075646 A1 and WO 2004/032957 A1 mentioned above are frequently only designated CNE, FNZ, ScIC, SFS, EAG, IdeE, IdeE2, Eq5, Eq8, IdeZ2, Eqz5, and Eqz8, respectively. EAG, IdeE, IdeE2, Eq5, and Eq8 designate proteins that can be found in S. equi and IdeZ2, Eqz5, and Eqz8 designate proteins that can be found in S. zooepidemicus. Other examples are the M or M-like proteins e.g. SeM described in Ref. 42.

Further examples of antigens that may be included in the antigenic composition of the invention comprise the ScIC proteins SCID-ScII (genbank acc. nos. DQ158080, DQ158081, DQ158082, DQ158083, DQ158084, DQ158085), FNE (acc. no. AF360373), FNEB (acc. no AY898649), FNEC-FNEF (Ref. 24), SeM (acc. no. U73162 also called FBP acc. no. YP002747233), SzPSe (acc. no. U73162), seeH (acc. no. AF186180), seeM (acc. no. AJ583528), seeI (GenBank, Gene ID7697191, SEQ_2037, Ref. 15), seeL (acc. no. AJ1583527), Se51.9 (acc. no. AF521601), Se46.8 (acc. no. AF521600), Se24.3 (acc. no. AY137521), Se75.3 (ace. no. AY137528), Se110.0 (acc. no. AY137519), Se24.3 (AY137521), Se42.0 (acc. no AY137521), Se117.0 (acc. no. AY137523), Se18.9 (acc. no. DQ068464), ZAG (acc. no. U25852), slaA (acc. no. CAW93317), slaB (acc. no. CAW95519), sagA (acc. no. ACG61862), streptolysin S biosynthesis proteins (CW92800, CW92802, CW92798), streptolysin S precursor (CW92796), SpyCEP (acc. no. DQ413032), the SpyCEP similar proteins SeCEP and SzoCEP (Ref. 43).

However, the proteins or polypeptide fragments that may be included in the antigenic compositions of the invention are not restricted to those listed above. In general, the invention can be used in principle with any extracellular protein or fragments thereof expressed on the surface or proteins transported into the environment of pathogenic streptococci, e.g. different subsp. of S. equi or S. pyogenes. By DNA sequence analysis of the genome of these bacteria e.g.www.sanger.ac.nk/Projects/S_equi/;

www.sanger.ac.uk/Progects/S_zooepidemicus/;

www.sanger.ac.uk/Projects/S_pyogenes/, open reading frames can be identified coding for extracellular proteins. These proteins are usually characterized by harboring an N-terminal signal sequence responsible for the transport across the membrane after translation. A particular interesting group of protein for vaccine development is proteins which in addition to harboring the signal sequence also display an easily recognized C-terminal domain including an amino acid motif generally defined as e.g. LPXTG [SEQ ID NO: 43], important for anchoring an extracellular protein to the peptidoglycan structure of the bacterial cell wall (Ref. 37). How to identify such proteins by bioinformatics methods, e.g. computer program SignalP (www.cbs.dtu.dk/services/SignalP/), (Refs. 19, 38), is well known to people skilled in the art.

The antigens or immunogens of the present antigenic or immunogenic compositions may comprise the entire amino acid sequence of said protein or polypeptide or may comprise a fragment, e.g. a C-terminal or N-terminal fragment thereof, or an analog thereof. These antigens may be used alone or in combinations. According to the invention, they may also by gene fusion technology be fused in various combinations and used as antigens in a vaccine. Furthermore, these fusion combinations may be used alone or in combination with other fusion combinations and/or in combination with single antigens.

According to the present invention, the antigenic compositions may comprise at least one antigen which is produced by recombinant technology and/or at least one antigen which is an isolated or purified antigen, or fragment thereof, such as the native forms produced by the streptococcal bacteria (or overproducing mutants). The native forms may be isolated from cells or growth media from bacteria grown in suitable media resulting in high production of the respective protein. In addition, after finding the optimal growth conditions (including physiological conditions) to obtain the native proteins it is also possible to construct overproducing streptococcal strains. Using methods well known for people skilled in the art there are several ways to generate and isolate overproducing strains, e.g. by site directed mutagenesis, chemical mutagenesis, ultraviolet light etc. The procedure of purifying and isolating an extracellular protein from growth media is well known for people skilled in the art.

From the above, it is evident that the present antigens or immunogens that are derived from proteins of S. equi, or S. zooepidemicus may comprise the entire protein, a fragment of said protein or an analog of said protein (like for instance synthetic peptides) which is immunogenic. Thus, the present invention is not limited to the fragments of proteins that are specifically disclosed herein.

The antigenic composition of the present invention may comprise at least one recombinant vector and at least one polynucleotide inserted therein that encodes said at least one protein or polypeptide, and which vector is able to express said polypeptide in vivo in a non-human mammal susceptible to infection with S. equi and/or S. zooepidemicus.

According to one embodiment of the present invention, the vector is an expression vector which is a plasmid or a viral vector and wherein said polynucleotide has a nucleotide sequence that encodes an antigen of the present invention.

The application of the present invention is not restricted to the usage of E. coli and vectors suitable for this bacterium as vehicles and tools to express recombinant polypeptides. Other hosts and vectors are well known in the art and can be found in literature and in literature cited in WO 2007/115059 A2. Furthermore, the application of the present application is not restricted to the specific nucleotide sequences of the antigens disclosed in the invention since it may be necessary to adapt the codon usage of the specific nucleotide sequences to the production host to be used. The technique to synthesize and adapt the codon usage is well known for people skilled in the art.

A further embodiment of the present invention is concerned with a vaccine composition for protecting non-human mammals against infection of S. equi, which comprises an antigenic composition as disclosed above as immunizing component, and a pharmaceutically acceptable carrier.

Suitably, the present vaccine composition comprises an antigenic or immunogenic composition that contains one or more of the present antigens or immunogens as immunizing component(s). Optionally, one or more of these antigens or immunogens are comprised of analogs of said proteins or fragments thereof.

The vaccine composition may comprise further components, such as an adjuvant. Suitably, said adjuvant stimulates systemic or mucosal immunity. Such adjuvants are well known in the art.

Suitable adjuvants for use according to the present invention comprise (1) polymers of acrylic or methacrylic acid, maleic anhydride and alkenyl derivative polymers, (2) immunostimulating sequences (ISS), (3) an oil in water emulsion, (4) cation lipids containing a quaternary ammonium salt, (5) cytokines, (6) aluminum hydroxide or aluminum phosphate, (7) saponin or (8) nanoparticles or (9) any combinations or mixtures thereof. Further examples of suitable adjuvants may also be found in literature cited in WO 2007/115059 A2.

A suitable adjuvant for use according to the present invention is the adjuvants Abisco, Matrix C and Matrix Q from Isconova AB, Sweden. The key components of ISCOMS are *Quillaia saponins* derived from the bark of the Chilean soap bark tree *Quillaia saporinaria* molina. *Quillaia saponins* are well known for their ability to activate the immune system (Ref. 32). *Quillaia saponins* mixed with cholesterol, and phospholipids under specific stochiomectry form spherical open cage like structures known as ISCOMS.

Another suitable adjuvant is *Ginseng*. *Ginseng* is a dry extract prepared from the root of the plant *Panax ginseng*, C. A. Meyer. *Ginseng* contains a number of active substances named ginsenosides that are a kind of saponins, chemically tri-terpenoid glycosides of the danunaran series. The ginsenosides have adjuvant properties and one of the most active adjuvants is the fraction named Rb1. It has been proved that the fraction Rb1 elicits a balanced Th1 and Th2 immune response as determined by measuring the levels of the cytokines IFN-γ, IL-2, IL-4, IL-10 secreted post vaccination with a Rb1 adjuvanted vaccine. In addition *ginseng* and the fraction Rb1 stimulate a strong antigen specific antibody response.

According to a suitable embodiment, the vaccine composition is a vaccine that protects susceptible mammals, suitably horses, against strangles caused by *S. equi* and against infections caused by *S. zooepidemicus*.

The vaccine composition of the present invention is provided in a physiologically administrable form. Suitably, it is administrable by intramuscular, subcutaneous, intradermal or intranasal inoculation.

Suitably, the vaccine composition of the present invention stimulates serum, mucosal and/or bronchial antibody responses directed to *S. equi* and/or *S. zooepidemicus* antigens in mammals susceptible to these bacteria, suitably horses.

The present invention is also related to a method for producing an antigen or immunogen to be used in an antigenic or immunogenic composition of the present invention, which method comprises the steps of (a) providing a DNA fragment encoding said antigen and introducing said fragment into an expression vector;

(b) introducing said vector, which contains said DNA fragment, into a compatible host cell;

(c) culturing said host cell provided in step (b) under conditions required for expression of the product encoded by said DNA fragment; and (d) isolating the expressed product from the cultured host cell.

Preferably, the method further comprises a step (e) wherein the isolated product from step (d) is purified, e.g. by affinity chromatography or other chromatographic methods known in the art.

Accordingly, the antigens of the present invention are usually produced according to recombinant techniques.

A further embodiment of the present invention is concerned with a method for preparation of a vaccine of the present invention, which vaccine contains as immunizing component an antigenic or immunogenic composition as disclosed above, said method comprising mixing said antigenic composition and a pharmaceutically acceptable carrier.

The present invention is also related to a method for the production of an antiserum, said method comprising administering an antigenic preparation of the present invention to an animal host to produce antibodies in said animal host and recovering antiserum containing said antibodies produced in said animal host.

Moreover, the present invention is concerned with a method of prophylactic or therapeutic treatment of *S. equi* and/or *S. zooepidemicus* infection in mammals, suitably horses, comprising administering to said mammal an immunologically effective amount of a vaccine or an antiserum of the present invention.

Accordingly, the present invention is related to a method for protecting horses against *S. equi* infection, which method comprises inoculating a horse subcutaneously, intranasally, intradermally, orally or intramuscularly, or any combination thereof with a vaccine composition of the present invention to induce an immune response against *S. equi* in said horse. Suitably, an immune response, in the form of IgG and/or IgA and/or IgM antibodies in the nasopharyngeal mucus, and/or serum is induced in said horse.

The present invention also relates to an antibody preparation comprising at least one, and suitably at least two, antibodies specific for a protein or a polypeptide of the present antigenic composition, which antibody/antibodies is/are polyclonal or monoclonal; or which preparation comprises a fragment of said antibodies.

The antibody preparation of the present invention could be used prophylactically or therapeutically against strangles and provides passive immunization when administered to a non-human mammal susceptible to infection by *S. equi* or infected by *S. equi*.

The present invention provides a vaccine composition comprising one or several antigen components which have been prepared according to the present method using *E. coli* as host cells. The source of these antigens might also be the native bacteria, if methods are developed for expression and purification thereof. Alternatively, the antigens of the present invention can also be produced according to methods that are based on fusion strategies where various parts of the respective antigen are recombined resulting in a fusion protein consisting of parts from different antigens. This fusion strategy could also be suitable for introducing an immune reactive part(s), e.g. T-cell epitopes or attenuated toxins (or parts thereof), thereby introducing other features suitable for optimizing the antigen presentation or localization.

The present invention may also be used in other vaccines or subunit immunogenic compositions, where the invention can be combined with one or more immunogens, antigens or epitopes selected from other pathogenic microorganisms or viruses to form multivalent subunit immunogenic compositions or vaccines. For example, concerning equine, such a multivalent subunit immunogenic composition or vaccine may comprise at least one polypeptide according to the present invention and at least one immunogen, antigen, or epitope from WEEV, EEV, VEEV, equine influenza virus, EHV-1, EHV-4, EAV, WNV, tetanus, *Rhodococcus*.

The present invention also provides diagnostic methods to measure antibodies against the various proteins (or fragments thereof) included in the vaccine composition. For instance, these types of methods may be used to determine antibody titers in sera before and/or after immunization or to determine antibody titers in infected mammals. The methods may also be applied to screen individual mammals to detect infected or chronical carriers of S. equi and S. zooepidemicus. Furthermore, the invention also provides a method to determine antibodies with neutralizing activity against the antigens in the vaccine thereby making it possible to measure the effect of e.g. immunization procedures or to identify individuals who lack antibodies that neutralize the antigens.

EXPERIMENTAL PART

Example 1

PCR Amplifications and Constructions of E. coli Clones

S. equi subspecies equi strain 1866 (obtained from Nordvacc Läkemedel AB, Sweden), (WO 2004/032957 A1, Ref. 25) was used as source of DNA for cloning. Chromosomal DNA from subspecies equi strain 1866 was prepared and used as a template to amplify various gene fragments presented in the Examples 2-8 and 16 further below. The sequences of primers used to amplify the various gene fragments are listed in Tables 2, 4 and 5. Cleavage sites for the restriction enzymes were included in the primer sequences. The plasmid vector pGEX-6P-1 (GE Healthcare, Uppsala, Sweden) (alternatively the pTYB4 vector, New England Biolabs, was used) was used for cloning and expression. The PCR amplifications were performed using the primers (20 pmol/µl) and FideliTaq™ PCR Master Mix (USB Corporation, Cleveland, Ohio) using the following programme: Step 1, pre-heat 1 minute at 95° C., DNA strand separation; Step 2, 30 seconds at 95° C.; Step 3, annealing 15 seconds at 5 degrees below the respective primer combination melting point; and Step 4, elongation for 2 minutes at 72° C., Steps 2-4 were run for 26 cycles. The PCR products were analysed on a 1% agarose gel, and thereafter purified using the QIAquick PCR Purification Kit™ (Qiagen). After cleavage with the restriction enzymes the fragments were purified one additional time using the same kit. After purification the fragments were ligated into the vector using ReadyToGo T4DNA Ligase (GE Healthcare, Uppsala, Sweden). After ligation, the respective sample were transformed into competent cells of E. coli strainTG1 using electroporation, and spread on LA-Amp plates (Luria-Bertani broth agar (15 g/L) plates supplemented with ampicillin, final conc. 50 µg/ml) and incubated over night at 37° C. Next day colonies were picked and analysed by PCR using the respective primer combination. Clones with the expected insert were grown and plasmid prepared. The sequence of the respective insert was also determined by DNA sequencing. Correct clones were transformed into competent cells of E. coli strain BL21 (DE3) pLys for protein expression.

TABLE 2

Primer sequences 5'-3'

| SEQ ID NO: 1. | CneBam: ggttggatccactaatcttagtgacaacatcac |
| SEQ ID NO: 2. | CneSac: TCCAGAGCTCCTTGACAGTAAAGCTGGTATAG |

TABLE 2-continued

Primer sequences 5'-3'

| SEQ ID NO: 3. | EagSac: agtggagctcttagacgcagcaacagtg |
| SEQ ID NO: 4. | EagXho: CACCCTCGAGTTATTTGGCTTTGTTGATTAAGGTC |
| SEQ ID NO: 5. | Eqc9: cgtagagctctcggaacccaatccatatc |
| SEQ ID NO: 6. | Eqc10: GAGGTCTAGAAGGACCTTGTTTGCCATTT |
| SEQ ID NO: 7. | Eqc11: agcatctagattatctggtccgccagga |
| SEQ ID NO: 8. | Eqc12: GAGGCTGCAGTGGACCTCGGGTACCGCCTT |
| SEQ ID NO: 9. | Eqc13: agtactgcaggaccagccagcagcactaa |
| SEQ ID NO: 10. | ScSac: TGCAGAGCTCTGGCTTTTGGGCAGCTTCTTC |
| SEQ ID NO: 11. | Eq8Bam: catggatccgcgactaccctagcaggac |
| SEQ ID NO: 12. | Eq8Nco: CTAGCCATGGGTGCTTAAGCTTTTCAATCTG |
| SEQ ID NO: 13. | 85Nco: agtaccatgggaaacgactactgctagtgc |
| SEQ ID NO: 14. | Eq5C2: CTGGCTCGAGTTATTTAGCAACCAAGGCTGC |
| SEQ ID NO: 15. | IdEG1: tactggatccgacgattaccaaaggaatgctac |
| SEQ ID NO: 16. | IdEG2: TGATCTCGAGTTAGCTCAGTTTCTGCCATATG |
| SEQ ID NO: 17. | Eq61p1: gtcggatccgaggataaggttgtgcaaactag |
| SEQ ID NO: 18. | Eq61p6: GCCTCTCGAGGGATAAGCTAGTCTGTCTTTGG |
| SEQ ID NO: 19. | 54Sac: ggcagagctcgatacagcaagctataccatcac |
| SEQ ID NO: 20. | 54Xba: TATTTCTAGAAGTTTTATAGGTGAAAACGATAACC |

Example 2

Construction of a Clone Expressing Fusion Protein Eq85

A gene fragment of eq8 was PCR amplified using primer pairs eq8Bam and eq8Nco. After amplification and purification the fragment was digested with BamHI and NcoI. Also a gene fragment of eq5 was PCR amplified using primer pairs 85Nco and eq5C2. After amplification and purification the fragment was digested with NcoI and XhoI. Both fragments were ligated into the BamHI and XhoI cleaved vector pGEX-6P-1.

SEQ ID NO: 21. Showing the nucleotide sequence of the gene fusion fragment encoding Eq85 inserted in the pGEX-6P-1 vector. The BamHI and XhoI sites are indicated in bold and the vector sequences are underlined. Note that the nucleotide A in bold and italics is different in this position compared to the published sequence in www.sanger.ac.uk/Projects/S_equi/;

TCTGTTCCAGGGGCCCCTGGGATCCGCGACTACCCTAGCAGGACAAACA
GAAGTACGGGCTGATAATATCTTACGCTTAGATATGACAGATAAAGAAG
CAGTTGAAAAATTCGCTAACGAGCTTAAAAATGAAGTCCATAAAAACTA
TCGTGGTAGTAATACTTGGCAAAAGCTTACCCTTATACTTAATGGTTAT
CAAAACCTTAGAGAACAAATAGAGACCGAGCTAAAAAATAGTGAACAAA
AAGTAAAAGAGCTTAATGATAAGGTTAATAGTGAAACTCAAGGAAAACA
AGAGTTACAGAATCAGCTTGAGAAAGAAAAAGAAGAGTTAGAAACACTA
AAAAAAGAGCTTGAAGCTGAGAAGGCTAAAGGAACTGGAGAAACAGAGA
AGCTTCAAAAGGAAATTGAAGCAAAAAATGCAATGATTTCTGACCTACA
AAAACAGCTTGAGGAAACTAAGCAAAGGGTTCAAGAGTTTGAAGCTGAA
GTAGGTAAATTAATGGCCGAAAAGGCAGACCTACAAACAAAATTAAATG
AACAAGAGCAGCTTAACGCTAAGCTTCAAAAAGAAATTGAAGACTTAAA
GGCTCAGATTGAAAAGCTTAAGCACCCATGGGAAACGACTACTGCTAGT
GCATTTGAAAATAATGGGACAGGTCAACATCTGAACTGGCACATAGATA
TTCCACAAGAATATACAGTTGAATTAGGAGAACCAATTACTATCTCAGA
TCTTATGAGTCAAATTACGGTTACTCGTAAAGGTAGTAATGGGACTGTT
AATGATGGAGATACTTTTGACTTTATTTCGAATGGAGATGGTTCAAGAG
GAATTGATACCCCTGGAGTAAAAATATGGTTTGACTTTTACAATGCTGC
GGGTACTTCCTTTTTAACTGATGAAATGTTAGCTTCGCCTACATATGCT
GTACCGGGGGGATCTTATACTATTAAAGCTTGGGTATTCTATGGGAAAA
ATGATACCAAAAAGCTCTTCACATTTAAACTAAAAAATTCCAACAGCAA
TAAAACTGAGTTAAGGAAGTCGTTAGAGGAGGCTAAGCTAAAACTCAGC
CAGCCTGAAGGAACGTATTCTGATGAATCACTGCAAGCCTTGCAATCAG
CGGTTACTATTGGTAAGACCTATTTAAACAGTGACCCTGATCAAAATAC
AGTAGATCAATCTGTTACTACTATTGATTCCGCTATTACTAGTCTTGTT
AATCTTAATGCTTTAAATGAAGCTATTAATCAAGCTACACCTTTTATAA
CAGATGGCAAAGAGTATCCTAAAGAAGCGTATGACGGTCTTGTGCAAAA
GCTTGCAGCGGCAGCTAAGCTTCAAAATTCATTTGGTCCTTCACAAGGA
GATGTTGATAAGGCTGCGACTGATTTAACGCAAGCTCTTACGACGCTTA
AGACTGCTGTAGCGCATGAAGCCTTAGATCAAGCCTTGGCTAAGCTGTT
AGAGCTTTACCGAGAAATCCAAATCTTGCTTTGACATCAGAGTCTTTG
AAGGAATTGTACAATAAGGCCATTGAAGCAGCAGGTACCTTCTATAGAA
CTGTTAACAAGGATAAAGAGAGAAAAGACATTTCCCTTTATGAGCTAGA
GCGCTACACTACAGAAACAAATTCAGTTGTTGATACTATTTTAAAGGTA
AAGGCTGCGATTGCCGAAGAAGGAAAGGCAAAATTGCGTTCTGCTTTAG
ACCAATTAAATGCTCTTATCGGAGAAAATCTAGACCTATCTCCATATAC
AGCAGCTTCTGCTCAAGCCTATACAGACCAGCTAGCTAAGGCTAAGGAG
GTCGCAGCAGCGGGTGAGACAGCTTATGCTCAGGAGACAGAACCGACAG

CTATTACTAACAGCTTGGTTAAGGTGTTAAATGCTAAGAAATCCCTCTC
AGATGCCAAGGCAGCCTTGGTTGCTAAATAACTCGAGCGGCCGCATCGT
G

SEQ ID NO: 22. Eq85 Fusion Protein. Underlined amino acids indicate the sequence originating from the vector. The * indicates a scissor protease cleavage site. Note that the amino acids in bold originate from the construction work of the fusion protein and that these amino acids could be changed or even absent if another fusion strategy is used. Note that the amino acid Ile (I) in bold and italics in this position is different compared to the published sequence in www.sanger.ac.uk/Projects/S_equi/;

LEVLFQ*GPLGSATTLAGQTEVRADNILRLDMTDKEAVEKFANELKNEV
HKNYRGSNTWQKLTLILNGYQNLREQIETELKNSEQKVICELNDKVNSE
TQGKQELQNQLEKEKEELETLKKELEAEKAKGTGETEKLQKEIEAKNAM
ISDLQKQLEETKQRVQEFEAEVGKLMAEKADLQTKLNEQEQLNAKLQKE
IEDLKAQIEKLKHPWETTTASAFENNGTGQHLNWHIDIPQEYTVELGEP
ITISDLMSQITVTRKGSNGTVNDGDTFDFISNGDGSRGIDTPGVKIWFD
FYNAAGTSFLTDEMLASPTYAVPGGSYTIKAWVFYGKNDTKKLFTFKLK
NSNSNKTELRKSLEEAKLKLSQPEGTYSDESLQALQSAVTIGKTYLNSD
PDQNTVDQSVTTIDSAITSLVNLNALNEAINQATPFITDGKEYPKEAYD
GLVQKLAAAAKLQNSFGPSQGDVDKAATDLTQALTTLKTAVAHEALDQA
LAKLLELYRENPNLALTSESLKELYNKAIEAAGTFYRTVNKDKERKDIS
LYELERYTTETNSVVDTILKVKAAIAEEGKAKLRSALDQLNALIGENLD
LSPYTAASAQAYTDQLAKAKEVAAAGETAYAQETEPTAITNSLVKVLNA
KKSLSDAKAALVAK

Example 3

Construction of a Clone Expressing Fusion Protein CCE

This gene fusion construct is made of five different *S. equi* gene fragments (cne, eq21, eq36, eq42 and eag). First a gene fragment of cne was PCR amplified using primer pairs CneBam and CneSac. After amplification and purification the fragment was digested with BamHI and SacI. Second, a gene fragment of eag was PCR amplified using primer pairs EagSac and EagXho. After amplification and purification the fragment was digested with SacI and XhoI. The purified cne and eag fragments were ligated into the BamHI and XhoI cleaved vector pGEX-6P-1. After transformation into *E. coli* a correct clone was identified and denoted pCNEEAG. Thereafter, a gene fragment of eq21 was PCR amplified using primer pairs eqc9 and eqc10. After amplification and purification the fragment was digested with SacI and XbaI. The gene fragment of eq36 was PCR amplified using primer pairs eqc11 and eqc12. After amplification and purification the fragment was digested with XbaI and PstI. The gene fragment of eq42 was PCR amplified using primer pairs eqc13 and ScSac. After amplification and purification the fragment was digested with PstI and SacI. The three cleaved fragments (eq21, eq36 and eq42) were ligated together and a new PCR was performed using primer pairs eqc9 and ScSac. The obtained PCR product was cleaved with SacI and ligated into SacI cleaved pCNEEAG generating pCCE harboring the gene fragments in the following order cne-eq21-eq36-eq42-eag.

SEQ ID NO: 23. Showing the nucleotide sequence of the gene fusion fragment of cne-eq21-eq36-eq42-eag inserted in the pGEX-6P-1 vector. The BamHI and XhoI sites are indicated in bold and the vector sequences are underlined.

<u>CTGGAAGTTCTGTTCCAGGGGCCCCTGGGATCC</u>ACTAATCTTAGTGACA

ACATCACATCATTGACGGTTGCTTCTTCATCACTCCGAGATGGAGAGAG

AACGACGGTAAAGGTTGCGTTTGATGACAAAAAACAGAAAATCAAGGCA

GGGGATACGATAGAGGTCACCTGGCCTACAAGTGGTAATGTCTACATTC

AGGGCTTTAATAAAACCATACCGCTTAATATTAGAGGGGTAGATGTTGG

TACCTTGGAGGTCACGCTAGACAAGGCTGTTTTCACATTCAATCAAAAT

ATTGAAACAATGCATGATGTCTCTGGTTGGGGAGAGTTTGATATTACTG

TTAGAAATGTGACACAAACCACCGCTGAAACATCAGGAACGACCACAGT

AAAGGTAGGCAATCGCACTGCTACTATCACTGTTACTAAGCCTGAGGCA

GGCACTGGTACCAGCTCATTTTATTATAAGACTGGTGATATGCAGCCCA

ATGATACTGAGCGTGTGAGATGGTTCCTGCTGATTAACAACAACAAGGA

ATGGGTGGCCAATACTGTTACAGTCGAAGACGATATTCAAGGTGGTCAA

ACCTTGGATATGAGCAGCTTTGACATCACCGTATCTGGTTATCGTAACG

AGCGCTTCGTTGGGGAAAACGCTCTGACAGAGTTTCATACAACATTTCC

AAATTCTGTCATTACGGCAACAGATAATCACATTAGTGTGCGGTTAGAT

CAATATGATGCCTCACAAAACACTGTCAACATTGCTTATAAGACAAAGA

TAACGGACTTTGACCAAAAAGAATTTGCCAACAACAGTAAAATCTGGTA

CCAGATTTTATACAAGGATCAGGTATCGGGTCAAGAGTCAAACCACCAA

GTAGCCAATATCAATGCTAACGGCGGGGTTGATGGCAGTCGCTATACCA

GCTTTACTGTCAAGGAGCTCTCGGAACCCAATCCATATCCAGATGTGAG

GCGTTTCCTTGATGAGAAGTACGATGGAGATGTGGATAAATTATCTAAA

CAACTTCAAGGTTATTTTGGTAGTTTAAGAGAGTATATAGAGTTTGAAC

TTAAAAATGGCAAACAAGGTCCTTCTAGATTATCTGGTCCGCCAGGATA

CCCACTTACTCGTGATTTCTCCCGTAACTTCCTAGAAGAAAATACTGCA

AAATATTTAGATCAATTAAGAGAACATCTACAGCACAGATTTAGTGAAC

TTGAGAGCTTAACAAGAAAATTAGAGAAAGAAGGCGGTACCCGAGGTCC

ACTGCAGGACCAGCCAGCAGCACTAAAATATCCAGAACCTAGAGACTAT

TTTCTTCATACTCGTGAAGGTGATGTTATTTATGATGAGGATATAAAAA

GATATTTTGAGGATTTAGAAGCCTATTTAACAGCTAGACTTGGTGGGAT

TGATAAAAAAGTAGAAGAAGCTGCCCAAAAGCCAGAGCTCTTAGACGCA

GCAACAGTGTTAGAGCCTACAACAGCCTTCATTAGAGAAGCTGTTAGGG

AAATCAATCAGCTGAGTGATGACTACGCTGACAATCAAGAGCTTCAGGC

TGTTCTTGCTAATGCTGGAGTTGAGGCACTTGCTGCAGATACTGTTGAT

CAGGCTAAAGCAGCTCTTGACAAAGCAAAGGCAGCTGTTGCTGGTGTTC

AGCTTGATGAAGCAAGACGTGAGGCTTACAGAACAATCAATGCCTTAAG

TGATCAGCACAAAAGCGATCAAAAGGTTCAGCTAGCTCTAGTTGCTGCA

GCAGCTAAGGTGGCAGATGCTGCTTCAGTTGATCAAGTGAATGCAGCCA

TTAATGATGCTCATACAGCTATTGCGGACATTACAGGAGCAGCCTTGTT

GGAGGCTAAAGAAGCTGCTATCAATGAACTAAAGCAGTATGGCATTAGT

GATTACTATGTGACCTTAATCAACAAAGCCAAATAACTCGAG<u>CGGCCGC</u>

<u>AT</u>

SEQ ID NO: 24. CCE fusion protein. Underlined amino acids indicate the sequence originating from the vector. The * indicates a scissor protease cleavage site. Note that the amino acids in bold originate from the construction work of the fusion protein and that these amino acids could be changed or even absent if another fusion strategy is used.

<u>LEVLFQ</u>*<u>GPLGS</u>TNLSDNITSLTVASSSLRDGERTTVKVAFDDKKQKINA

GDTIEVTWPTSGNVYIQGFNKTIPLNIRGVDVGTLEVTLDKAVFTFNQNI

ETMHDVSGWGEFDITVRNVTQTTAETSGTTTVKVGNRTATITVTKPEAGT

GTSSFYYKTGDMQPNDTERVRWFLLINNNKEWVANTVTVEDDIQGGQTLD

MSSFDITVSGYRNERFVGENALTEFHTTFPNSVITATDNHISVRLDQYDA

SQNTVNIAYKTKITDFDQKEFANNSKIWYQILYKDQVSGQESNHQVANIN

ANGGVDGSRYTSFTVKELSEPNPYPDVRRFLDEKYDGDVDKLSKQLQGYF

GSLREYIEFELKNGKQGPSRLSGPPGYPLTRDFSRNFLEENTAKYLDQLR

EHLQHRFSELESLTRKLEKEGGTRGPLQDQPAALKYPEPRDYFLHTREGD

VIYDEDIKRYFEDLEAYLTARLGGIDKKVEEAAQKPELLDAATVLEPTTA

FIREAVREINQLSDDYADNQELQAVLANAGVEALAADTVDQAKAALDKAK

AAVAGVQLDEARREAYRTINALSDQHKSDQKVQLALVAAAAKVADAASVD

QVNAAINDAHTAIADITGAALLEAKEAAINELKQYGISDYYVTLINKAK

Example 4

Construction of a Clone Expressing IdeE

A gene fragment of the ideE gene was PCR amplified using primer pairs IdEG1 and IdEG2. After amplification and purification the fragment was digested with BamHI and XhoI and ligated into the BamHI and XhoI cleaved vector pGEX-6P-1.

SEQ ID NO: 25. The nucleotide sequence of the ideE gene inserted in the pGEX-6P-1 vector. The BamHI and XhoI sites are indicated in bold and the vector sequences are underlined.

<u>CTGGAAGTTCTGTTCCAGGGGCCCCTGGGATCC</u>GACGATTACCAAAGGAA

TGCTACGGAAGCTTATGCCAAAGAAGTACCACATCAGATCACTTCTGTAT

GGACCAAAGGTGTTACACCACTAACACCCGAGCAGTTTCGATATAATAAC

GAAGATGTGATCCATGCGCCATATCTTGCTCATCAAGGCTGGTACGATAT

CACCAAGGCCTTCGATGGGAAGGATAATCTCTTGTGTGGCGCAGCAACGG

CAGGTAATATGCTGCATTGGTGGTTTGATCAAAATAAAACAGAGATTGAA

GCCTATTTAAGTAAACACCCCTGAAAAGCAAAAAATCATTTTTAACAACCA

AGAGCTATTTGATTTGAAAGCTGCTATCGATACCAAGGACAGTCAAACCA
ATAGTCAGCTTTTTAATTATTTTAGAGATAAAGCCTTTCCAAATCTATCA
GCACGTCAACTCGGGGTTATGCCTGATCTTGTTCTAGACATGTTTATCAA
TGGTTACTACTTAAATGTGTTTAAAACACAGTCTACTGATGTCAATCGAC
CTTATCAGGACAAGGACAAACGAGGTGGTATTTTCGATGCTGTTTTCACC
AGAGGAGATCAGACAACGCTCTTGACAGCTCGTCATGATTTAAAAAATAA
AGGACTAAATGACATCAGCACCATTATCAAGCAAGAACTGACTGAAGGAA
GAGCCCTTGCTTTATCACATACCTACGCCAATGTTAGCATTAGCCATGTG
ATTAACTTGTGGGGAGCTGATTTTAATGCTGAAGGAAACCTTGAGGCCAT
CTATGTCACAGACTCAGATGCTAATGCGTCTATTGGTATGAAAAAATATT
TTGTCGGCATTAATGCTCATAGACATGTCGCCATTTCTGCCAAGAAATA
GAAGGAGAAAACATTGGCGCTCAAGTATTAGGCTTATTTACGCTTTCCAG
TGGCAAGGACATATGGCAGAAACTGAGCTAACTCGAGCGGCCGCAT

SEQ ID NO: 26. IdeE protein. Underlined amino acids indicate the sequence originating from the vector. The * indicates a scissor protease cleavage site.

LEVLFQ*GPLGSDDYQRNATEAYAKEVPHQITSVWTKGVTPLTPEQFRYN
NEDVIHAPYLAHQGWYDITKAFDGKDNLLCGAATAGNMLHWWFDQNKTEI
EAYLSKHPEKQKIIFNNQELFDLKAAIDTKDSQTNSQLFNYFRDKAFPNL
SARQLGVMPDLVLDMFINGYYLNVFKTQSTDVNRPYQDKDKRGGIFDAVF
TRGDQTTLLTARHDLKNKGLNDISTIIKQELTEGRALALSHTYANVSISH
VINLWGADFNAEGNLEAIYVTDSDANASIGMKKYFVGINAHREVAISAKK
IEGENIGAQVLGLFTLSSGKDIWQKLS

Example 5

Construction of a Clone Expressing Fusion Protein CNEEAG

A gene fragment of cne was PCR amplified using primer pairs CneBam and CneSac. After amplification and purification the fragment was digested with BamHI and SacI. Also gene fragment of eag was PCR amplified using primer pairs EagSac and EagXho. After amplification and purification the fragment was digested with SacI and XhoI. Both fragments were ligated into the BamHI and XhoI cleaved vector pGEX-6P-1.

SEQ ID NO: 27. Showing the nucleotide sequence of the gene fusion fragment cne-eag encoding CNEEAG inserted in the pGEX-6P-1 vector. The BamHI and XhoI sites are indicated in bold and the vector sequences are underlined.

CTGGAAGTTCTGTTCCAGGGGCCCCTGGGATCCACTAATCTTAGTGACAA
CATCACATCATTGACGGTTGCTTCTTCATCACTCCGAGATGGAGAGAGAA
CGACGGTAAAGGTTGCGTTTGATGACAAAAAACAGAAAATCAAGGCAGGG
GATACGATAGAGGTCACCTGGCCTACAAGTGGTAATGTCTACATTCAGGG
CTTTAATAAAACCATACCGCTTAATATTAGAGGGGTAGATGTTGGTACCT
TGGAGGTCACGCTAGACAAGGCTGTTTTCACATTCAATCAAATATTGAA
ACAATGCATGATGTCTCTGGTTGGGGAGAGTTTGATATTACTGTTAGAAA
TGTGACACAAACCACCGCTGAAACATCAGGAACGACCACAGTAAAGGTAG
GCAATCGCACTGCTACTATCACTGTTACTAAGCCTGAGGCAGGCACTGGT
ACCAGCTCATTTTATTATAAGACTGGTGATATGCAGCCCAATGATACTGA
GCGTGTGAGATGGTTCCTGCTGATTAACAACAACAAGGAATGGGTGGCCA
ATACTGTTACAGTCGAAGACGATATTCAAGGTGGTCAAACCTTGGATATG
AGCAGCTTTGACATCACCGTATCTGGTTATCGTAACGAGCGCTTCGTTGG
GGAAAACGCTCTGACAGAGTTTCATACAACATTTCCAAATTCTGTCATTA
CGGCAACAGATAATCACATTAGTGTGCGGTTAGATCAATATGATGCCTCA
CAAAACACTGTCAACATTGCTTATAAGACAAAGATAACGGACTTTGACCA
AAAAGAATTTGCCAACAACAGTAAAATCTGGTACCAGATTTTATACAAGG
ATCAGGTATCGGGTCAAGAGTCAAACCACCAAGTAGCCAATATCAATGCT
AACGGCGGGGTTGATGGCAGTCGCTATACCAGCTTTACTGTCAAGGAGCT
CTTAGACGCAGCAACAGTGTTAGAGCCTACAACAGCCTTCATTAGAGAAG
CTGTTAGGGAAATCAATCAGCTGAGTGATGACTACGCTGACAATCAAGAG
CTTCAGGCTGTTCTTGCTAATGCTGGAGTTGAGGCACTTGCTGCAGATAC
TGTTGATCAGGCTAAAGCAGCTCTTGACAAAGCAAAGGCAGCTGTTGCTG
GTGTTCAGCTTGATGAAGCAAGACGTGAGGCTTACAGAACAATCAATGCC
TTAAGTGATCAGCACAAAAGCGATCAAAAGGTTCAGCTAGCTCTAGTTGC
TGCAGCAGCTAAGGTGGCAGATGCTGCTTCAGTTGATCAAGTGAATGCAG
CCATTAATGATGCTCATACAGCTATTGCGGACATTACAGGAGCAGCCTTG
TTGGAGGCTAAAGAAGCTGCTATCAATGAACTAAAGCAGTATGGCATTAG
TGATTACTATGTGACCTTAATCAACAAAGCCAAATAACTCGAGCGGCCGC
AT

SEQ ID NO: 28. CNEEAG Fusion Protein. Underlined amino acids indicate the sequence originating from the vector. The * indicates a scissor protease cleavage site. Note that the amino acids in bold originate from the construction work of the fusion protein and that these amino acids could be changed or even absent if another fusion strategy is used.

LEVLFQ*GPLGSTNLSDNITSLTVASSSLRDGERTTVKVAFDDKKQKIKA
GDTIEVTWPTSGNVYIQGFNKTIPLNIRGVDVGTLEVTLDKAVFTFNQNI
ETMHDVSGWGEFDITVRNVTQTTAETSGTTTVKVGNRTATITVTKPEAGT
GTSSFYYKTGDMQPNDTERVRWFLLINNNKEWVANTVTVEDDIQGGQTLD
MSSFDITVSGYRNERFVGENALTEFHTTFPNSVITATDNHISVRLDQYDA
SQNTVNIAYKTKITDFDQKEFANNSKIWYQILYKDQVSGQESNHQVANIN
ANGGVDGSRYTSFTVKELLDAATVLEPTTAFIREAVREINQLSDDYADNQ
ELQAVLANAGVEALAADTVDQAKAALDKAKAAVAGVQLDEARREAYRTIN
ALSDQHKSDQKVQLALVAAAAKVADAASVDQVNAAINDAHTAIADITGAA
LLEAKEAAINELKQYGISDYYVTLINKAK

Example 6

Construction of a Clone Expressing Fusion Protein IE5

A gene fragment of the ideE gene was PCR amplified using primer pairs IdEG1 and IENco. After amplification and purification the fragment was digested with BamHI and NcoI. Also gene fragment of eq5 was PCR amplified using primer pairs 85Nco and eq5C2. After amplification and purification the fragment was digested with NcoI and XhoI. Both fragments were ligated into the BamHI and XhoI cleaved vector pGEX-6P-1.

SEQ ID NO: 29. The nucleotide sequence of the ideE-eq5 fusion inserted in the pGEX-6P-1 vector. The BamHI and XhoI sites are indicated in bold and the vector sequences are underlined.

```
CTGGAAGTTCTGTTCCAGGGGCCCCTGGGATCCGACGATTACCAAAGGAA
TGCTACGGAAGCTTATGCCAAAGAAGTACCACATCAGATCACTTCTGTAT
GGACCAAAGGTGTTACACCACTAACACCCGAGCAGTTTCGATATAATAAC
GAAGATGTGATCCATGCGCCATATCTTGCTCATCAAGGCTGGTACGATAT
CACCAAGGCCTTCGATGGGAAGGATAATCTCTTGTGTGGCGCAGCAACGG
CAGGTAATATGCTGCATTGGTGGTTTGATCAAAATAAAACAGAGATTGAA
GCCTATTTAAGTAAACACCCTGAAAAGCAAAAAATCATTTTTAACAACCA
AGAGCTATTTGATTTGAAAGCTGCTATCGATACCAAGGACAGTCAAACCA
ATAGTCAGCTTTTTAATTATTTTAGAGATAAAGCCTTTCCAAATCTATCA
GCACGTCAACTCGGGGTTATGCCTGATCTTGTTCTAGACATGTTTATCAA
TGGTTACTACTTAAATGTGTTTAAAACACAGTCTACTGATGTCAATCGAC
CTTATCAGGACAAGGACAAACGAGGTGGTATTTTCGATGCTGTTTTCACC
AGAGGAGATCAGACAACGCTCTTGACAGCTCGTCATGATTTAAAAAATAA
AGGACTAAATGACATCAGCACCATTATCAAGCAAGAACTGACTGAAGGAA
GAGCCCTTGCTTTATCACATACCTACGCCAATGTTAGCATTAGCCATGTG
ATTAACTTGTGGGGAGCTGATTTTAATGCTGAAGGAAACCTTGAGGCCAT
CTATGTCACAGACTCAGATGCTAATGCGTCTATTGGTATGAAAAAATATT
TTGTCGGCATTAATGCTCATAGACATGTCGCCATTTCTGCCAAGAAAATA
GAAGGAGAAACATTGGCGCTCAAGTATTAGGCTTATTTACGCTTTCCAG
TGGCAAGGACATATGGCAGAAACTGAGCCCATGGGAAACGACTACTGCTA
GTGCATTTGAAAATAATGGGACAGGTCAACATCTGAACTGGCACATAGAT
ATTCCACAAGAATATACAGTTGAATTAGGAGAACCAATTACTATCTCAGA
TCTTATGAGTCAAATTACGGTTACTCGTAAAGGTAGTAATGGGACTGTTA
ATGATGGAGATACTTTTGACTTTATTTCGAATGGAGATGGTTCAAGAGGA
ATTGATACCCCTGGAGTAAAAATATGGTTTGACTTTTACAATGCTGCGGG
TACTTCCTTTTTAACTGATGAAATGTTAGCTTCGCCTACATATGCTGTAC
CGGGGGGATCTTATACTATTAAAGCTTGGGTATTCTATGGGAAAAATGAT
ACCAAAAAGCTCTTCACATTTAAACTAAAAAATTCCAACAGCAATAAAAC
TGAGTTAAGGAAGTCGTTAGAGGAGGCTAAGCTAAAACTCAGCCAGCCTG
AAGGAACGTATTCTGATGAATCACTGCAAGCCTTGCAATCAGCGGTTACT
ATTGGTAAGACCTATTTAAACAGTGACCCTGATCAAAATACAGTAGATCA
ATCTGTTACTACTATTGATTCCGCTATTACTAGTCTTGTTAATCTTAATG
CTTTAAATGAAGCTATTAATCAAGCTACACCTTTTATAACAGATGGCAAA
GAGTATCCTAAAGAAGCGTATGACGGTCTTGTGCAAAAGCTTGCAGCGGC
AGCTAAGCTTCAAAATTCATTTGGTCCTTCACAAGGAGATGTTGATAAGG
CTGCGACTGATTTAACGCAAGCTCTTACGACGCTTAAGACTGCTGTAGCG
CATGAAGCCTTAGATCAAGCCTTGGCTAAGCTGTTAGAGCTTTACCGAGA
AAATCCAAATCTTGCTTTGACATCAGAGTCTTTGAAGGAATTGTACAATA
AGGCCATTGAAGCAGCAGGTACCTTCTATAGAACTGTTAACAAGGATAAA
GAGAGAAAAGACATTTCCCTTTATGAGCTAGAGCGCTACACTACAGAAAC
AAATTCAGTTGTTGATACTATTTTAAAGGTAAAGGCTGCGATTGCCGAAG
AAGGAAAGGCAAAATTGCGTTCTGCTTTAGACCAATTAAATGCTCTTATC
GGAGAAAATCTAGACCTATCTCCATATACAGCAGCTTCTGCTCAAGCCTA
TACAGACCAGCTAGCTAAGGCTAAGGAGGTCGCAGCAGCGGGTGAGACAG
CTTATGCTCAGGAGACAGAACCGACAGCTATTACTAACAGCTTGGTTAAG
GTGTTAAATGCTAAGAAATCCCTCTCAGATGCCAAGGCAGCCTTGGTTGC
TAAATAACTCGAGCGGCCGCAT
```

SEQ ID NO: 30. IE5 Fusion Protein. Underlined amino acids indicate the sequence originating from the vector. The * indicates a scissor protease cleavage site. Note that the amino acids in bold originate from the construction work of the fusion protein and that these amino acids could be changed or even absent if another fusion strategy is used. Note that the amino acid Ile (I) in bold and italics in this position is different compared to the published sequence in www.sanger.ac.uk/Projects/S_equi/;

LEVLFQ*GPLGSDDYQRNATEAYAKEVPHQITSVWTKGVTPLTPEQFRYN

NEDVIHAPYLAHQGWYDITKAFDGKDNLLCGAATAGNMLHWWFDQNKTEI

EAYLSKHPEKQKIIFNNQELFDLKAAIDTKDSQTNSQLFNYFRDKAFPNL

SARQLGVMPDLVLDMFINGYYLNVFKTQSTDVNRPYQDKDKRGGIFDAVF

TRGDQTTLLTARHDLKNKGLNDISTIIKQELTEGRALALSHTYANVSISH

VINLWGADFNAEGNLEAIYVTDSDANASIGMKKYFVGINAHRHVAISAKK

IEGENIGAQVLGLFTLSSGKDIWQKLSPWETTTASAFENNGTGQHLNWHI

DIPQEYTVELGEPITISDLMSQITVTRKGSNGTVNDGDTFDFISNGDGSR

GIDTPGVKIWFDFYNAAGTSFLTDEMLASPTYAVPGGSYTIKAWVFYGKN

DTKKLFTFKLKNSNSNKTELRKSLEEAKLKLSQPEGTYSDESLQALQSAV

TIGKTYLNSDPDQNTVDQSVTTIDSAITSLVNLNALNEAINQATPFITDG

KEYPKEAYDGLVQKLAAAAKLQNSFGPSQGDVDKAATDLTQALTTLKTAV

AHEALDQALAKLLELYRENPNLALTSESLKELYNKAIEAAGTFYRTVNKD

KERKDISLYELERYTTETNSVVDTILKVKAAIAEEGKAKLRSALDQLNAL

IGENLDLSPYTAASAQAYTDQLAKAKEVAAAGETAYAQETEPTAITNSLV

KVLNAKKSLSDAKAALVAK

Example 7

Construction of a Clone Expressing EndoSe

A gene fragment of the endoSe gene was PCR amplified using primer pairs eq61p1 and eq61p6. After amplification and purification the fragment was digested with BamHI and XhoI and ligated into the BamHI and XhoI cleaved vector pGEX-6P-1.

SEQ ID NO: 31. The nucleotide sequence of the endoSe gene inserted in the pGEX-6P-1 vector. The BamHI and XhoI sites are indicated in bold and the vector sequences are underlined.

CTGGAAGTTCTGTTCCAGGGGCCCCTGGGATCCGAGGATAAGGTTGTGCA
AACTAGTCCATCAGTCTCTGCTATTGATGACCTACATTACCTGTCGGAAA
ACAGTAAAAAAGAATTTAAGGAGGGGTTATCAAAGGCAGGAGAAGTACCT
GAAAAGCTAAAGGATATTTTATCCAAGGCACAGCAGGCAGATAAGCAGGC
AAAGGTTCTTGCAGAAATGAAGGTTCCTGAAAAAATAGCCATGAAGCCTT
TAAAGGGGCCTCTTTATGGTGGCTATTTTAGGACTTGGCATGATAAAACA
TCAGATCCGGCTGAAAAGGATAAGGTTAATTCTATGGGAGAATTGCCTAA
GGAGGTTGACTTAGCCTTTGTTTTCCATGATTGGACCAAGGATTATAGCT
TTTTCTGGCAAGAATTGGCGACCAAGCATGTGCCAACGCTGAACAAGCAG
GGAACACGTGTGATTCGTACCATTCCATGGCGGTTCCTTGCAGGCGGTGA
TCATAGTGGTATTGCTGAAGATACGCAAAAATACCCAAATACTCCAGAGG
GAAATAAGGCCTTGGCAAAGGCTATTGTAGATGAATACGTTTATAAATAT
AATCTTGATGGTTTAGATGTTGATATTGAGCGGGATAGCATTCCAAAAGT
AAATGGAAAAGAGAGTAACGAAAATATTCAGCGCTCTATTGCTGTTTTTG
AAGAAATTGGCAAGCTTATTGGGCCAAAGGGCGCTGACAAGTCACGTTTG
TTCATTATGGATAGCACCTACATGGCTGACAAGAACCCATTGATTGAGCG
CGGTGCCCAATATATTGATTTGCTGCTTGTGCAGGTTTATGGCACTCAAG
GTGAGAAGGGAGATTGGGATCCAGTCGCTAGAAAACCTGAAAAGACAATG
GAGGAACGTTGGGAATCGTATAGCAAATACATTCGTCCTGAGCAGTACAT
GGTTGGTTTTTCTTTCTATGAGGAATATGCGGGCAGTGGTAACCTCTGGT
ATGATATTAATGAGAGGAAAGATGATCATAATCCGTTAAATTCAGAGATA
GCTGGTACTCGTGCTGAGCGTTATGCAAAATGGCAGCCTAAGACAGGTGG
TGTCAAGGGAGGGATTTTCTCTTATGCGATTGATCGCGATGGTGTAGCGC
ATCAACCTAAAAAGTCTCAGATGATGAGAAAAGAACTAACAAGGCTATA
AAGGATATAACAGATGGTATTGTCAAATCAGATTATAAGGTTTCTAAGGC
CTTGAAGAAGGTTATGGAAAATGACAAATCCTATGAGCTGATTGATCAGA
AAGATTTTCCAGACAAGGCTTTGCGAGAAGCAGTTATTGCACAGGTTGGA
AGCAGAAGAGGGGATTTAGAGCGGTTCAATGGAACCCTGCGCTTAGACAA
TCCGGATATCAAGAGTTTAGAAGGCCTGAATAAGCTTAAAAAACTAGCTA
AGCTAGAGCTAATCGGTCTATCACAAATCACAAAGCTGGATAGCTTAGTC
CTACCTGCAAATGCTAAGCCGACCAAGGATACGCTGGCCAATGTTCTTGA
AGCCTACGACAGCGCTAAGAAGGAAGAGACTAAGGCGATTCCACAGGTGG
CTCTGACCATTTCTGGTCTAACTGGCTTGAAGGAATTAAATCTTGCTGGC
TTTGATCGTGATAGCTTGGCTGGAATTGACGCAGCTAGCCTAACCTCTCT
TGAAAAGGTGGATCTCTCTAGTAATAAGCTGGACTTAGCAGCTGGTACGG
AAAATCGTCAGATTCTTGATACCATGCTGGCAACAGTGACTAAGCATGGC
GGTGTTAGCGAAAAGACGTTTGTATTTGATCATCAAAAGCCTACTGGTCT
TTATCCTGATACTTATGGCACTAAGAGCCTTCAGTTACCAGTAGCAAATG
ATACAATTGATTTGCAGGCTAAGCTTTTATTTGGAACAGTTACCAATCAG
GGCACGCTAATCAATAGCGAAGCTGACTATAAGGCTTATCAGGAGCAGGA
AATAGCAGGTCACCGTTTTGTTGATTCAAGCTATGATTACAAAGCCTTTG
CAGTGACCTACAAGGACTATAAGATCAAGGTGACTGACTCAACCTTAGGT
GTCACTGATCACAAGGACTTATCCACTAGCAAGGAGGAGACCTACAAGGT
TGAATTCTTTAGCCCTACTAATAGCACTAAGCCTGTGCATGAGGCTAAGG
TTGTCGTTGGTGCGGAAAAAACCATGATGGTTAACCTAGCAGAGGGAGCA
ACTGTGATTGGTGGTGATGCAGATCCAACAAATGCAAAAAAAGTGTTTGA
TGGTTTGCTCAATAATGATACAACAATTCTGTCAACTAGCAATAAAGCTT
CTATCATTTTTGAACTTAAAGAGCCTGGCTTAGTCAAGTATTGGCGTTTC
TTTAATGACAGCAAAATTAGTAAAGCTGACTGTATTAAGGAGGCCAAGCT
TGAAGCCTTTGTTGGCCATCTTGAAGCTGGCTCAAAGGTAAAGGATAGCT
TGGAAAAATCATCAAAATGGGTAACAGTTTCAGATTATTCAGGAGAGGAC
CAAGAGTTTAGCCAGCCGTTAAACAACATTGGTGCCAAATATTGGAGAAT
AACAGTTGATACTAAGGGAGGACGTTACAATTGGCCATCACTTCCTGAGC
TTCAAATCATTGGTTATCAATTACCGGCTGCGGATCTTGTGATGGCAATG
CTAGCTACTGCAGAGGAGCTATCTCAGCAAAAAGACAAGTTCTCTCAAGA
GCAGCTTAAGGAGCTCGAAGTCAAAATAGCTGCCTTAAAGGCTGCTTTAG
ATAGTAAGATGTTTAATGCCGATGCTATTAACGCTAGTACTGCTGATCTG
AAGGCTTATGTTGATAAGCTTTTAGCTGATAGAACTGATCAGGAAAAAGT
AGCTAAAGCAGCTAAAGTTGAGCAGCCTGTGGCTACTGACATAAAAGAAA
ATACTGAGCCAGAAAATCCAAAGACAGACTAGCTTATCCCTCGAGCGGCC
GCAT

SEQ ID NO: 32. EndoSe protein. Underlined amino acids indicate the sequence originating from the vector. The * indicates a scissor protease cleavage site. Note that the amino acid Y in bold and italics is different in this position compared to the published sequence in www.sanger.ac.uk/Projects/S_equi/;

LEVLFQ*GPLGSEDKVINTSPSVSAIDDLHYLSENSKKEFKEGLSKAGEV
PEKLIMILSKAQQADKQAKVLAEMKVPEKIAMKPLKGPLYGGYFRTWHDK
TSDPAEKDKVNSMGELPKEVDLAFVFHDWTKDYSFFWQELATKHVPTLNK
QGTRVIRTIPWRELAGGDHSGIAEDTQKYPNTPEGNKALAKAIVDEYVYK
YNLDGLDVDIERDSIPKVNGKESNENIQRSIAVFEEIGKLIGPKGADKSR
LFIMDSTYMADKNPLIERGAQYIDLLLVQVYGTQGEKGDWDPVARKPEKT

-continued

```
MEERWESYSKYIRPEQYMVGFSFYEEYAGSGNLWYDINERKDDHNPLNSE
IAGTRAERYAKWQPKTGGVKGGIFSYAIDRDGVAHQPKKVSDDEKRTNKA
IKDITDGIVKSDYKVSKALKKVMENDKSYELIDQKDFPDKALREAVIAQV
GSRRGDLERFNGTLRLDNPDIKSLEGLNKLKKLAKLELIGLSQITKLDSL
VLPANAKPTKDTLANVLEAYDSAKKEETKAIPQVALTISGLTGLKELNLA
GFDRDSLAGIDAASLTSLEKVDLSSNKLDLAAGTENRQILDTMLATVTKH
GGVSEKTFVFDHQKPTGLYPDTYGTKSLQLPVANDTIDLQAKLLFGTVTN
QGTLINSEADYKAYQEQEIAGHRFVDSSYDYKAFAVTYKDYKIKVTDSTL
GVTDHKDLSTSKEETYKVEFFSPTNSTKPVHEAKVVVGAEKTMMVNLAEG
ATVIGGDADPTNAKKVFDGLLNNDTTILSTSNKASIIFELKEPGLVKYWR
FENDSKISKADCIKEAKLEAFVGHLEAGSKVKDSLEKSSKWVTVSDYSGE
DQEFSQPLNNIGAKYWRITVDTKGGRYNWPSLPELQIIGYQLPAADLVMA
MLATAEELSQQKDKESQEQLKELEVKIAALKAALDSKMFNADAINASTAD
LKAYVDKLLADRTDQEKVAKAAKVEQPVATDIKENTEPENPKTD
```

Example 8

Construction of a Clone Expressing Fusion Protein CPCE

This gene fusion construct is made of five different *S. equi* gene fragments (cne, eq54, eq36, eq42 and eag). The gene fragment of eq54 was PCR amplified using primer pairs 54Sac and 54XbaI. After amplification and purification the fragment was digested with SacI and XbaI. The eq36-eq42 fragment was obtained by PCR using primer pairs eqc11 and ScSac with the DNA from construct CCE as template. After amplification and purification the fragment was digested with SacI and XbaI. The two cleaved DNA fragments were ligated into the construct CNEEAG previously cleaved with SacI, generating a clone harboring the gene fragments in the following order cne-eq54-eq36-eq42-eag.

SEQ ID NO: 33. Showing the nucleotide sequence of the gene fusion fragment of cne-eq54-eq36-eq42-eag inserted in the pGEX-6P-1 vector. The BamHI and XhoI sites are indicated in bold and the vector sequences are underlined.

CTGGAAGTTCTGTTCCAGGGGCCCCTGGGATCCACTAATCTTAGTGACAA

```
CATCACATCATTGACGGTTGCTTCTTCATCACTCCGAGATGGAGAGAGAA
CGACGGTAAAGGTTGCGTTTGATGACAAAAAACAGAAAATCAAGGCAGGG
GATACGATAGAGGTCACCTGGCCTACAAGTGGTAATGTCTACATTCAGGG
CTTTAATAAAACCATACCGCTTAATATTAGAGGGGTAGATGTTGGTACCT
TGGAGGTCACGCTAGACAAGGCTGTTTTCACATTCAATCAAAATATTGAA
ACAATGCATGATGTCTCTGGTTGGGGAGAGTTTGATATTACTGTTAGAAA
TGTGACACAAACCACCGCTGAAACATCAGGAACGACCACAGTAAAGGTAG
GCAATCGCACTGCTACTATCACTGTTACTAAGCCTGAGGCAGGCACTGGT
ACCAGCTCATTTTATTATAAGACTGGTGATATGCAGCCCAATGATACTGA
GCGTGTGAGATGGTTCCTGCTGATTAACAACAACAAGGAATGGGTGGCCA
ATACTGTTACAGTCGAAGACGATATTCAAGGTGGTCAAACCTTGGATATG
```

-continued

```
AGCAGCTTTGACATCACCGTATCTGGTTATCGTAACGAGCGCTTCGTTGG
GGAAAACGCTCTGACAGAGTTTCATACAACATTTCCAAATTCTGTCATTA
CGGCAACAGATAATCACATTAGTGTGCGGTTAGATCAATATGATGCCTCA
CAAAACACTGTCAACATTGCTTATAAGACAAAGATAACGGACTTTGACCA
AAAAGAATTTGCCAACAACAGTAAAATCTGGTACCAGATTTTATACAAGG
ATCAGGTATCGGGTCAAGAGTCAAACCACCAAGTAGCCAATATCAATGCT
AACGGCGGGGTTGATGGCAGTCGCTATACCAGCTTTACTGTCAAGGAGCT
CGATACAGCAAGCTATACCATCACTGTTGAGGGAGCTACAGCAGGTCACA
CCTATGAGGCTTATCAGATTTTCAAGGGTGACTTGTTTGACAGTACCCTA
TCAAACATCACATGGGGAGGTGGTGTTACACCTTTTGAATTTGATGGTTC
AAAAGACGCTGCTAAGATTGCAGAGGGATTGAAGGAAGCAAATGCAGCTG
CCTTTGCCAAGGAAGCAGGTAAGCACTTGACAGCAACCATTGCAGGAACA
GGAACACATGCAATCACCGTTAACGAGGCTGGCTACTACCTCATCAAGGA
CAAAAATGATTCTCAAACAGGCAAGCATGACGCCTACACCTCATTTGTCC
TGAAGGTTGTTAAAAACACCAGCTTCAAACCAAAATCTGCTATCCCAACA
GTCCTTAAAAAGGTCAAGGACCGTAATGACAAGACAGGTCTTGAGACAGG
CTGGCAAGATTCAGCTGACTATGACAAAAATGACAAGGTGCCATTCCAGC
TAACCGCAACCCTACCGTCAAATTACGATGCCTTTCAAGAATACTACCTT
GAATTTGTAGATACCTTATCAAAAGGGCTAAGCTACAACAAAGACGCCAA
GGTCTATGTGGTTAATGGAGATACTCGTCAAGATATTACTAATTCATTTA
CAGTTAGTGAAGATGGTTCATCTTTTAAAATCAATAACCTAAAGGCTGTT
CAGGGAGTAACAATAACAGCTACCAGTAAGATCGTTGTCGAATACACTGC
TACCCTCAATGACCAAGCGGCCATCGGCAAAAAAGGAAATCCAAACGAAG
TTGCTTTGAAATACTCAAACGATCCAAACGCTCTTGGAAAAGGAGAGGAG
TCTCCAAAAGGGGAGACACCAAAAGACAAGGTTATCGTTTTCACCTATAA
AACTTCTAGATTATCTGGTCCGCCAGGATACCCACTTACTCGTGATTTCT
CCCGTAACTTCCTAGAAGAAAATACTGCAAAATATTTAGATCAATTAAGA
GAACATCTACAGCACAGATTTAGTGAACTTGAGAGCTTAACAAGAAAATT
AGAGAAAGAAGGCGGTACCCGAGGTCCACTGCAGGACCAGCCAGCAGCAC
TAAAATATCCAGAACCTAGAGACTATTTTCTTCATACTCGTGAAGGTGAT
GTTATTTATGATGAGGATATAAAAAGATATTTTGAGGATTTAGAAGCCTA
TTTAACAGCTAGACTTGGTGGGATTGATAAAAAAGTAGAAGAAGCTGCCC
AAAAGCCAGAGCTCTTAGACGCAGCAACAGTGTTAGAGCCTACAACAGCC
TTCATTAGAGAAGCTGTTAGGGAAATCAATCAGCTGAGTGATGACTACGC
TGACAATCAAGAGCTTCAGGCTGTTCTTGCTAATGCTGGAGTTGAGGCAC
TTGCTGCAGATACTGTTGATCAGGCTAAAGCAGCTCTTGACAAAGCAAAG
GCAGCTGTTGCTGGTGTTCAGCTTGATGAAGCAAGACGTGAGGCTTACAG
AACAATCAATGCCTTAAGTGATCAGCACAAAAGCGATCAAAAGGTTCAGC
TAGCTCTAGTTGCTGCAGCAGCTAAGGTGGCAGATGCTGCTTCAGTTGAT
CAAGTGAATGCAGCCATTAATGATGCTCATACAGCTATTGCGGACATTAC
```

```
-continued
AGGAGCAGCCTTGTTGGAGGCTAAAGAAGCTGCTATCAATGAACTAAAGC

AGTATGGCATTAGTGATTACTATGTGACCTTAATCAACAAAGCCAAATAA

CTCGAGCGGCCGCAT
```

SEQ ID NO: 34. CPCE Fusion Protein. Underlined amino acids indicate the sequence originating from the vector. The * indicates a scissor protease cleavage site. Note that the amino acids in bold originate from the construction work of the fusion protein and that these amino acids could be changed or even absent if another fusion strategy is used.

```
LEVLFQ*GPLGSTNLSDNITSLTVASSSLRDGERTTVKVAFDDKKQKIKA

GDTIEVTWPTSGNVYIQGFNKTIPLNIRGVDVGTLEVTLDKAVFTFNQNI

ETMHDVSGWGEFDITVRNVTQTTAETSGTTTVKVGNRTATITVTKPEAGT

GTSSFYYKTGDMQPNDTERVRWFLLINNNKEWVANTVTVEDDIQGGQTLD

MSSFDITVSGYRNERFVGENALTEFHTTFPNSVITATDNHISVRLDQYDA

SQNTVNIAYKTKITDFDQKEFANNSKIWYQILYKDQVSGQESNHQVANIN

ANGGVDGSRYTSFTVKELDTASYTITVEGATAGHTYEAYQIFKGDLFDST

LSNITWGGGVTPFEFDGSKDAAKIAEGLKEANAAAFAKEAGKHLTATIAG

TGTHAITVNEAGYYLIKDKNDSQTGKHDAYTSFVLKVVKNTSFKPKSAIP

TVLKKVKDRNDKTGLETGWQDSADYDKNDKVPFQLTATLPSNYDAFQEYY

LEFVDTLSKGLSYNKDAKVYVVNGDTRQDITNSFTVSEDGSSFKINNLKA

VQGVTITATSKIVVEYTATLNDQAAIGKKGNPNEVALKYSNDPNALGKGE

ESPKGETPKDKVIVFTYKTSRLSGPPGYPLTRDFSRNFLEENTAKYLDQL

REHLQHRFSELESLTRKLEKEGGTRGPLQDQPAALKYPEPRDYFLHTREG

DVIYDEDIKRYFEDLEAYLTARLGGIDKKVEEAAQKPELLDAATVLEPTT

AFTREAVREINQLSDDYADNQELQAVLANAGVEALAADTVDQAKAALDKA

KAAVAGVQLDEARREAYRTINALSDQHKSDQKVQLALVAAAAKVADAASV

DQVNAAINDAHTAIADITGAALLEAKEAAINELKQYGISDYYVTLINKAK
```

Example 9

Purification of Recombinant Proteins

The pGEX-6P-1 vector used is a part of an *E. coli* expression and purification system called GST-glutathione affinity system (GE Healthcare, Uppsala, Sweden). Briefly, following the manufacturer's instructions the clones encoding recombinant proteins were grown at 37° C. in Luria Bertani Broth medium supplemented with ampicillin (final conc. 50 µg/ml). At an optical density (OD$_{600}$)~0.6, the growth medium was supplemented with IPTG (final conc. 0.2mM) and the growth temperature shifted to 15° C. After incubation over night the *E. coli* cells were harvested and resuspended in a PBS phosphate-buffered saline [137 mM NaCl, 2.7 mM KCl, 10 mM Na$_2$HPO$_4$, 1.4 mM KH$_2$PO$_4$ (pH 7.4)] supplemented with TWEEN™ 20 (polysorbate 20), final conc. 0.1% (v/v) (PBST) and lysozyme was added (final conc. 50 µg/ml) whereupon the cells were lysed by freezing and thawing. After centrifugation, the supernatant was sterile filtrated and batch purified with Glutathione SEPHAROSE™ (crosslinked agarose) beads. After extensive washing using PBST the fusion protein was treated with scissor protease to release the recombinant proteins. The eluted samples containing the antigens were dialysed against PBS and concentrated. Finally, the amounts of antigens obtained were determined using spectrophotometer and the quality analyzed by SDS-PAGE (performed under reducing conditions) whereupon the gels were coomassie brilliant blue stained. The proteins were stored finally at −20° C. It should be noted that each protein produced in this system (SEQ ID NOS: 22, 24, 26, 28, 30, 32 and 34) contains five additional N-terminal amino acids, Gly-Pro-Leu-Gly-Ser, which are derived from the vector. The C-terminal end of each protein is as stated since a stop codon was added in the primer sequence.

Another *E. coli* expression and purification system used was the IMPACT system from New England Bio labs. The use of this system to produce *S. equi* recombinant proteins has previously been described (e.g. Ref. 14). It should be noted that each protein produced in this system (SEQ ID NOS: 38 and 42) contains five additional amino acids, one Met in the N-terminal part and four Leu-Glu-Pro-Gly at the C-terminal which are derived from the vector.

Example 10

Formulation of Strangvacc Vaccines for Horse Immunizations

The recombinant proteins described in the examples were after purification (Example 9) mixed in the following combinations.

Strangvacc 1.

This combination of seven recombinant proteins (earlier called Septavacc) consists of proteins (fragments of) EAG, CNE, SclC, IdeE, IdeE2, SEQ0256 (Eq5), SEQ0402 (Eq8) and has previously been described in WO 2009/075646 (A1) and Refs. 13 and 14.

Strangvacc 2.

This combination consists of four recombinant proteins IdeE2, IdeE, Eq85 and CCE of which two are fusion proteins (Eq85 and CCE).

Strangvacc 3/4.

This combination consists of three recombinant proteins IdeE, Eq85 and CCE of which two are fusion proteins (Eq85 and CCE).

Strangvacc 5.

This combination consists of three recombinant proteins CNEEAG, IE5 and EndoSe of which two are fusion proteins (CNEEAG and IE5).

Strangvacc 7.

This combination consists of two recombinant fusion proteins CPCE and IE5.

Strangvacc 8.

This combination consists of three recombinant proteins CPCE, IE5 and EndoSe of which two are fusion proteins (CPCE and IE5).

Each of the Strangvacc vaccines (1-8) was briefly formulated as follows:

For subcutaneous immunization each dose contained 75 µg of each protein mixed with 375 µg/dose of the adjuvant Matrix C. (Except for Strangvacc 1 where each dose contained 50 µg of each protein). Dose volume was 2 ml which was subcutaneously injected 1 ml+1 ml close to the retropharyngeal lymph nodes on each side.

For intranasal immunization each dose contained 225 µg of each protein mixed with 500 µg/dose of the adjuvant Matrix Q. (Except for Strangvacc 1 where each dose contained 150 μg of each protein). Dose volume was 4 ml which was intranasal injected 2 ml+2 ml in each nostril.

For intramuscular immunization each dose contained 300 μg of each protein mixed with 375 μg/dose of the adjuvant Matrix C. Dose volume 2 ml that was injected at one location intramuscular.

To adjust the volumes in resp. Strangvacc preparation PBS was used. In the placebo samples the recombinant proteins were omitted. Matrix C and Q was obtained from Isconova AB, Uppsala, Sweden.

Horses were vaccinated three times. Time between first and second vaccination was seven weeks. The time between second and third vaccination was two weeks and horses were challenged two weeks after the last vaccination.

Example 11

Immunization and Challenge Studies in Horses

Study I. This vaccination and challenge study was performed at Animal Health Trust, Lanwades Park, Kentford, Newmarket, Suffolk, CB8 7UU, UK sponsored by Intervacc AB, Sweden (study identification B009/001). Study II (study identification B009/002) was also performed at the same location. The objective of these studies were to determine the level of protection conferred on vaccination with variants of Intervacc's new multi-component subunit vaccine following intranasal challenge with wild type *S. equi* strain 4047 in Welsh Mountain ponies.

Briefly, all procedures for immunisation, experimental infection and clinical assessment of the horses were as described in PLoS Path, Guss et al (2009), Ref. 14, and WO 2009/075646 A1. However, study II was extended to also include a separate group of horses (group 6) that were only vaccinated intramuscularly (three vaccinations). Briefly, in the vaccination and challenge studies several parameters were monitored such as clinical symptoms, rectal temperature, injection site observations, and swelling of lymph nodes etc. The number of *S. equi* and *S. zooepidemicus* bacteria were also monitored. Furthermore, blood samples were also taken and used to determine e.g. neutrophils and fibrinogen levels and antibody response against antigens present in the respective vaccine. After completion of the vaccination/challenges studies the horses were euthanized and post mortem (PM) examinations were performed.

TABLE 3

Vaccination groups. IN means intranasal immunization. SC means subcutan immunization. Matrix is an adjuvant of Isconova AB, Uppsala, Sweden.

| Group | Vaccine | Pony Chip ID's | Route | PM |
|---|---|---|---|---|
| Study I | | | | |
| 1 | Strangvacc 2 + Matrix | 2691, 2695, 2703, 2711, 2717, 2811 | IN + SC | 17 |
| 2 | Strangvacc 3/4 + Matrix | 2849, 2900, 2901, 2930, 3028, 3060 | IN + SC | 21 |
| 3 | Placebo + adjuvants | 3156, 3250, 3693, 3736, 3844, 9624 | IN + SC | 48 |
| Study II | | | | |
| 1 | Strangvac 3/4 + Matrix | 0278, 0594, 0481, 0504, 1529 | IN + SC | 2 |
| 2 | Strangvacc 5 + Matrix | 1567, 2226, 2259, 2277, 2417, 2749 | IN + SC | 21 |
| 3 | Strangvacc 7 + Matrix | 2227, 2633, 2775, 3305, 3329, 3611 | IN + SC | 18 |

TABLE 3-continued

Vaccination groups. IN means intranasal immunization. SC means subcutan immunization. Matrix is an adjuvant of Isconova AB, Uppsala, Sweden.

| Group | Vaccine | Pony Chip ID's | Route | PM |
|---|---|---|---|---|
| 4 | Strangvacc 8 + Matrix | 2720, 3062, 3680, 3773, 3942, 3954 | IN + SC | 26 |
| 5 | Placebo + Matrix | 3839, 9893, 4069, 9170, 9408 | IN + SC | 38 |
| 6 | Strangvacc 8 + Matrix | 3596, 3730, 3762, 2799, 2991, 9240, 9807 | Intra-muscular | 28 |

PM = Mean value from pathology score as taken at post mortem examination.

Example 12

Welsh Mountain Ponies were vaccinated with Strangvacc 2 (n=6), Strangvacc 3/4 (n=6) and placebo (n=6) in Study I. In Study II ponies were vaccinated with Strangvacc 3/4 (n=5), Strangvacc 5 (n=6), Strangvacc 7 (n=6), Strangvacc 8 (n=6) and placebo (n=5). Ponies given placebo serve as controls and were given adjuvant only. Immunisations were done at three occasions intranasally and subcutaneously on both sides. All ponies were experimentally infected with *S. equi* to cause strangles. The ponies were subjected to clinical examinations daily and rectal temperatures were monitored. Pyrexia is a typical sign of strangles and correlates very well with inflammatory parameters, such as elevated fibrinogen level and neutrophil counts in blood. All procedures for immunisation, experimental infection and clinical assessment of the horses were as described in PLoS Path, Guss et al (2009).

FIG. 1 (FIGS. 1A-C) includes 8 panels, each showing the temperature of individual ponies for each group vaccinated as indicated on top of each panel. It is clear from the graphs that different formulations result in different levels of protection. As an example, vaccination with Strangvacc 3/4 results in only one out of eleven ponies (Studies I and II combined) with pathological pyrexia, defined as temperature exceeding 39° C. Strangvacc 8, on the other hand, although protective, results in 3-4 out of six ponies with pyrexia.

Example 13

Ponies vaccinated as described for Example 12 above were subjected to post mortem analysis at the end point of the experiments. The endpoint is defined as pyrexia for 3 days, obvious clinical signs of infection with suffering or at the end of study (day 21 in study I or day 25 in Study II). A scoring system was used for various post mortem observations as described in PLoS Path, Guss et al (2009), Ref 14. The added score is shown in FIG. 2 where each dot represents an individual pony. Of the eleven ponies vaccinated with Strangvacc 3/4 only three displayed a pathological high score. The highest score (46) is the same individual as the one with pyrexia. Strangvacc 8 resulted in two ponies fully protected and one intermediate, based on the post mortem scoring. Using a Mann Whitney statistical analysis of the groups in comparison with the combined placebo groups (n=11), the following p-values were obtained: Strangvacc 2, 0.0019; Strangvacc 3/4, 0.00027; Strangvacc 5, 0.0048; Strangvacc 7, 0.00064; Strangvacc 8, 0.078. A good correlation was found between parameters such as time to pyrexia and post mortem score; short time to pyrexia was found in ponies with high post mortem score. As obvious from the graph, different combinations of fusion proteins in the vaccines result in different level of protection.

Example 14

Antibody responses in vaccinated ponies were determined as described in PLoS Path, Guss et al (2009), Ref. 14. Briefly, a conventional ELISA test was used where serum samples were diluted in two-fold series. The log values of the dilution required to give an absorbance value of 1.0 were determined for each sample. Sera were analysed from ponies immunised in a previous study where a vaccine, Septavacc (also called Strangvacc 1) was used. Strangvacc 1 contains seven recombinant proteins as single proteins. Sera were also analysed from ponies vaccinated with various fusion proteins.

All ponies vaccinated with any of the Strangvacc vaccines responded immunologically. This is the case both for Strangvacc 1, where antigens are single antigens, and for the other Strangvacc vaccines with fusion proteins.

In no case did a fusion protein result in an encompassed protein becoming non-immunogenic, due to unfavourable folding or exposure to the immune system.

Figure 3:
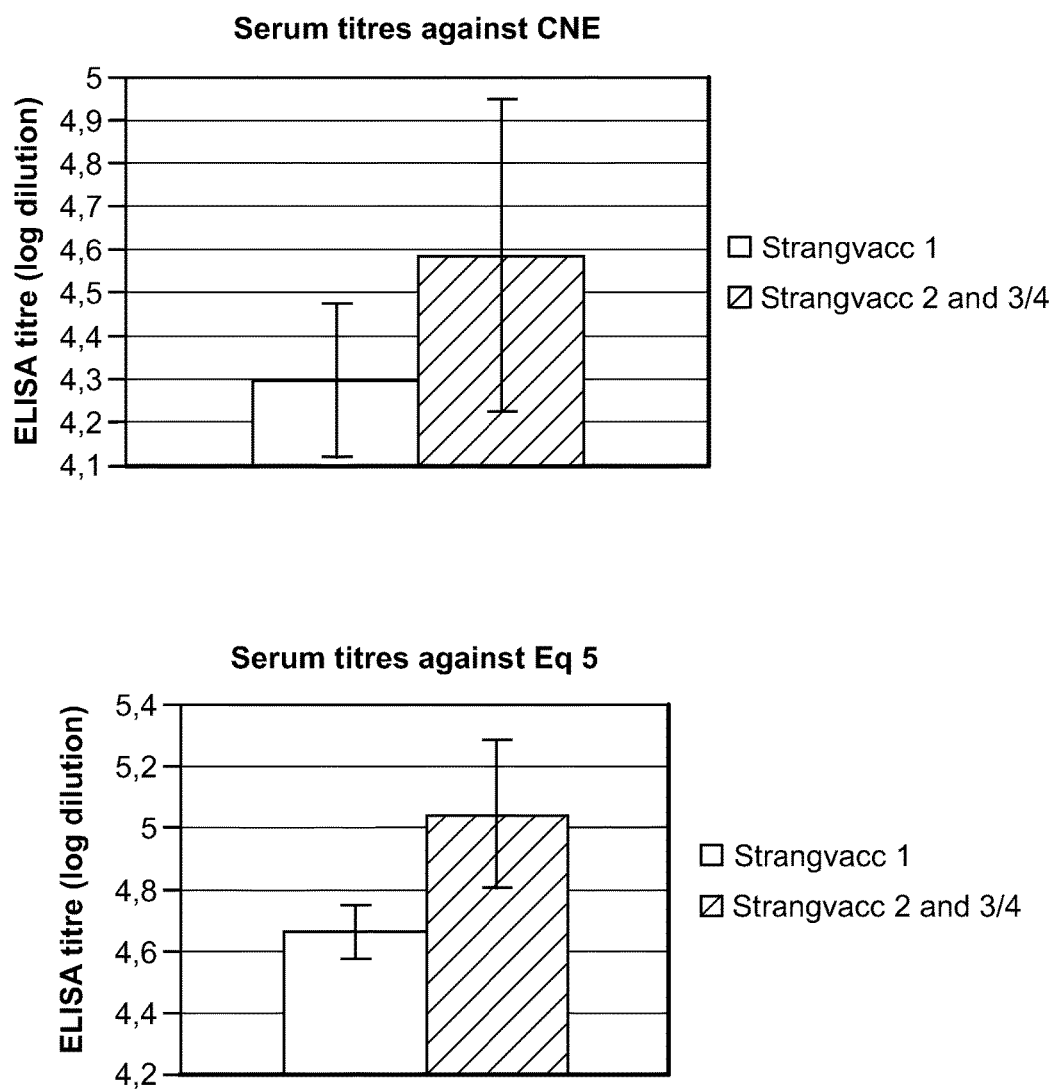
FIG. 3 is diagrams showing antibody levels in ponies vaccinated with Strangvacc I (containing single antigens) or Strangvacc 2 and 3/4 (data combined together)(containing fusion proteins). Top diagram (panel) shows antibodies against CNE, and bottom diagram (panel) shows antibodies against Eq5 (SEQ0256).

FIG. 3 shows instead that immunogenicity are in some cases significantly enhanced by using fusion proteins. Top panel in FIG. 3 shows that antibodies in ponies vaccinated with Strangvacc 2 and Strangvacc 3/4 have significantly (p=0.04) better anti CNE antibodies than ponies vaccinated with Strangvacc 1. CNE is in Strangvacc 2 and 3/4 included in the same fusion as EAG. In Strangvacc 1, CNE is included as a single protein. Similarly, bottom panel in FIG. 3 shows that antibodies against Eq5 (=SEQ0256) are significantly higher (p 0.0008) in ponies vaccinated with fusion proteins than with Eq5 as a single protein.

Example 15

Intramuscular Vaccination Using Strangvacc 8

The intramuscular vaccination using Strangvacc 8 (group 6 in study II) resulted in a protection level similar to group 4 in study II.

Example 16

Construction of Clones Expressing Eq54 and Eq27 Protein Fragments to be Used as Recombinant Antigens in Vaccination of Mice Against *S. equi* Infection A gene fragment of the eq54 gene was PCR amplified using primer pairs Eq54F and Eq54R. After amplification and purification the fragment was digested with NcoI and XhoI and ligated into the NcoI and XhoI cleaved vectorpTYB4 obtained from New England Biolabs Inc., USA (NEB).

TABLE 4

Primers used to clone eq54 gene fragment

SEQ ID 35. Eq54F 5'-gcatccatggatacagcaagctatacc a-3'

SEQ ID 36. Eq54R 3'-caattattttttcccagataggagctc agct-5'

TABLE 4 -continued

Primers used to clone eq54 gene fragment

SEQ ID NO: 37. The nucleotide sequence of the eq54 gene inserted in the pTYB4 vector. The NcoI and XhoI sites are indicated in bold and the vector sequences are underlined.

CCATGGATACAGCAAGCTATACCATCACTGTTGAGGGAGCTACAGCAGGT

CACACCTATGAGGCTTATCAGATTTTCAAGGGTGACTTGTTTGACAGTAC

CCTATCAAACATCACATGGGGAGGTGGTGTTACACCTTTTGAATTTGATG

GTTCAAAAGACGCTGCTAAGATTGCAGAGGGATTGAAGGAAGCAAATGCA

GCTGCCTTTGCCAAGGAAGCAGGTAAGCACTTGACAGCAACCATTGCAGG

AACAGGAACACATGCAATCACCGTTAACGAGGCTGGCTACTACCTCATCA

AGGACAAAAATGATTCTCAAACAGGCAAGCATGACGCCTACACCTCATTT

GTCCTGAAGGTTGTTAAAAACACCAGCTTCAAACCAAAATCTGCTATCCC

AACAGTCCTTAAAAAGGTCAAGGACCGTAATGACAAGACAGGTCTTGAGA

CAGGCTGGCAAGATTCAGCTGACTATGACAAAAATGACAAGGTGCCATTC

CAGCTAACCGCAACCCTACCGTCAAATTACGATGCCTTTCAAGAATACTA

CCTTGAATTTGTAGATACCTTATCAAAAGGGCTAAGCTACAACAAAGACG

CCAAGGTCTATGTGGTTAATGGAGATACTCGTCAAGATATTACTAATTCA

TTTACAGTTAGTGAAGATGGTTCATCTTTTAAAATCAATAACCTAAAGGC

TGTTCAGGGAGTAACAATAACAGCTACCAGTAAGATCGTTGTCGAATACA

CTGCTACCCTCAATGACCAAGCGGCCATCGGCAAAAAAGGAAATCCAAAC

GAAGTTGCTTTGAAATACTCAAACGATCCAAACGCTCTTGGAAAAGGAGA

GGAGTCTCCAAAAGGGGAGACACCAAAAGACAAGGTTATCGTTTTCACCT

ATAAAACTATCATCAATAAGGTTGATCAAGATCAAAAAGCCCTAAAAGGT

GCAGGCTTTACCCTTTATAAGCTGGTCAAAGGTGATAATGGCGAGGAAAA

ATATCAAATAGTCCAAGAAATTAAAGCAGGGGATACAACTAGCTTTGAGT

TTGTTGGACTTGACGCTGGTGATTACAAGCTCAGCGAAACAACAACACCT

GGCGGTTACAACACTATTGCAGATGTCATGTTCAGCATTGTAGCGCAGCA

TGAAACCGAGTCAGACGATCCTCAGTTGACTAGCCTAACCGTTGACAAAG

CAACTGGCTTCACTGCTGATACAGAAGCTGGTACCGTATCCGCAACTATT

GTTAATAAAAGGTCTATCCTCGAGCCCGGGTGC

SEQ ID NO: 38. Eq54 protein expressed using the IMPACT™-system (NEB). Note that N-terminal amino acid Met and the four C-terminal amino acids Leu-Glu-Pro-Gly originate from the vector.

MDTASYTITVEGATAGHTYEAYQIFKGDLFDSTLSNITWGGGVTPFEFDG

SKDAAKIAEGLKEANAAAFAKEAGKHLTATIAGTGTHAITVNEAGYYLIK

DKNDSQTGKHDAYTSFVLKVVKNTSFKPKSAIPTVLKKVKDRNDKTGLET

GWQDSADYDKNDKVPFQLTATLPSNYDAFQEYYLEEVDTLSKGLSYNKDA

KVYVVNGDTRQDITNSFTVSEDGSSFKINNLKAVQGVTITATSKIVVEYT

ATLNDQAAIGKKGNPNEVALKYSNDPNALGKGEESPKGETPKDKVIVFTY

KTIINKVDQDQKALKGAGFTLYKLVKGDNGEEKYQIVQEIKAGDTTSFEF

-continued

VGLDAGDYKLSETTTPGGYNTIADVMFSIVAQHETESDDPQLTSLTVDKA

TGFTADTEAGTVSATIVNKRSILEPG

The IMPACT-system was also used to clone and express a fragment of the Eq27 protein. A gene fragment of the eq27 gene was PCR amplified using primer pairs Eqp271 and Eqp272. After amplification and purification the fragment was digested with NcoI and XhoI and ligated into the NcoI and XhoI cleaved vectorpTYB4 obtained from New England Biolabs Inc., USA (NEB)

TABLE 5

Primers(5'-3') used to clone eq27 gene fragment.

SEQ ID NO: 39. Eqp271: gcagccatggagagtctgacgagt gttga

SEQ ID NO: 40. Eqp272: TCACCTCGAGTCCTAGCTCACCGT

CATAAGC

SEQ ID NO: 41. The nucleotide sequence of the eq27 gene inserted in the pTYB4 vector. The NcoI and XhoI sites are indicated in bold and the vector sequences are underlined.
CCATGGAGAGTCTGACGAGTGTTGAGCCTGCTGATGGTGCGGTCATGGT

CAAGTCAGAGGCTGCTGACCAAGGCTCAAATGAGCTACCAGAAGCTACT

GACATTAGTGATATTGCTGGTATTTCTGATGTGACTAAGGTGTCAGCTG

CTGTCAATGCTGATACTGTCAAGGAAGTTCAGCCAGTAGCTGTACCTCT

TGTAGAGGATCAGGCGCATGAGGAAACTACAGACCAGTCTCAGCCTTCA

TCATCGATAGTGTCTGTTACGACAGACAGCTCTCTAGAGACACCAGAAG

CTACAAGCTCAGAGGAGCCGATAGCGGAGCAGACCTTGCGGCTGCATTT

CAAGACCCTGCCAGCTCAAGACCTATCCTCGCTTGGTCTTTGGGTGTGG

GACGATGTTGAGACACCATCTGATCAGCTGGGAGGCTGGCCGACTGGGG

CTACCAATTTTAGTCTAGCGAAGACAGATGACTATGGCTATTACATGGA

CGTTAAGCTTTCAGCCAATCAAGCCAATAAGGTTAGCTTTTTGATCAAT

AACACTAAGGGAGACAATCTGACGGGCGATCGAACCATAGACCTTCTCA

GCCCTAAGATGAATGAGGTCTGGATTGATGGCCAGGAGCTGTCTTACTA

TCGGCCGCTGGCTCAGGGCTATATCCGTATCAATTATTATCGCAGTGAT

GGCCATTATGACAACAAATCGCTCTGGCTTTGGGGAAGTGCTGATGCGT

CAATGACTAGTCAGCAGGGCGCTTGGCCAGATGGTATTGATTTTAAGCA

GGTCGGTCGATATGGTGCTTATATAGATGTCAAGCTAGCTGATACCAAT

GAGCTAGGCTTTCTCTTGCTAGATGAGCGTCAGACAGGTGACGCTGTTA

AAATTCAGCCCAATGATTATATTTTTAAAGATTTAAAGAATCACACCCA

AATTTTCTTGAAAGACGAGGATCCAACCATTTATACGAACCCTTATTTT

GTTAATACAGTTAGATTAATCGGTGCTCAGCAGGTCAGCCCAAGCAGTA

TTGAGGCGAGCTTTACGACTCTAGCAGATGTGGATAAGGAAAGCCTTTT

AAAAGAATTAAAAATCAGCACTGACAGTAAGGAAGCAGTTGCTATTACT

GATATCACCTTAGATGAAAAGACTCATAAGGCTGTCATCACAGGTGATT

TTACTCAAGCAGTGGCCACTTATACGGTGACCTTTCATCATGAGAGCTT

TABLE 5 -continued

Primers(5'-3') used to clone eq27 gene fragment.

CCAGGCTAGGCCAAATTGGCAATACAAGGATAGCCTGTATGCTTATGAC

GGTGAGCTAGGACTCGAGCCCGGGTGC

SEQ ID NO: 42. Eq27 protein fragment expressed using the IMPACT™-system (NEB). Note that N-terminal amino acid Met and the four C-terminal amino acids Leu-Glu-Pro-Gly originate from the vector.

MESLTSVEPADGAVMVKSEAADQGSNELPEATDISDIAGISDVTKVSAAV

NADTVKEVQPVAVPLVEDQAHEETTDQSQPSSSIVSVTTDSSLETFEATS

SEEPIAEQTLRLHFKTLPAQDLSSLGLWVWDDVETPSDQLGGWPTGATNF

SLAKTDDYGYYMDVKLSANQANKVSFLINNTKGDNLTGDRTIDLLSPKMN

EVWIDGQELSYYRPLAQGYIRINYYRSDGHYDNKSLWLWGSADASMTSQQ

GAWPDGIDFKQVGRYGAYIDVKLADTNELGFLLLDERQTGDAVKIQPNDY

IFKDLKNHTQIFLKDEDPTIYTNPYFVNTVRLIGAQQVSPSSTEASFTTL

ADVDKESLLKELKISTDSKEAVAITDITLDEKTHKAVITGDFSQAVATYT

VTFHHESFQARPNWQYKDSLYAYDGELGLEPG

Intranasal Vaccination with Eq 54 and Eq27 Followed by Challenge with *Streptococcus equi*

Example 17

Immunisation of Mice with Eq54 and Eq27

Mice (NMRI) weighting approximately 23-25 g were kept in cages of five animals in each. The mice were immunised intranasally with 12 micrograms of each antigen and 10 microgram of Abisco 300 (Isconova AB, Sweden). Ten animals were immunised with Eq54, 10 animals were immunised with Eq27 and 10 were given Abisco 300 adjuvant only to serve as a negative control. Immunisations were given on days 0, 31 and 45.

Example 18

Experimental Infection with *Streptococcus equi*

Experimental infection was given on day 52 (7 days after last time of immunisation). *S. equi* strain 1866 from a clinical case of strangles was used. The strain was first passed through an animal by inoculating ca $10^6$ CFU into the nostrils of an anaesthetized mouse. Bacteria were recovered after 7 days from the nose of the mouse and grown on BG plates (agar plates containing 5% sheep blood 0.01% *gentiana* violet) at 37° C. in 5% $CO_2$. A single colony was grown on BG plates overnight at 37° C. and resuspended in Todd Hewitt Broth (Oxoid, Basingstoke, Hampshire, United Kingdom) (THB) with 1% yeast extract (THY). The bacteria were kept at −80° C. in vials and a new vial was used for each experiment. To infect mice, bacteria were grown on BG plates at 37° C. in 5% $CO_2$ overnight, followed by inoculation into THB supplemented with 1% Yeast extract (THY) and grown without shaking over night. The culture was then diluted 10 times into THY and 10% horse serum (Sigma) and grown for 4 hours at 37° C. in 5% $CO_2$. The culture was centrifuged and resuspended in THB. A dose containing $1\times10^6$ CFU in 10 µl was used for all *S. equi* infections of mice. The animals were followed daily. Bacterial nasal growth was scored on a four-graded scale from 0 to +++ by gently pressing the nose of the animal onto a BG plate in a reproducible manner. The nasal sample was then spread out onto the entire surface of the plate. One + means 5-100 colonies; two + means more than 100 and three + means confluent growth. The weight was determined every day and the percentage of weight-loss was calculated.

Example 19

Experimental Results of Vaccination with Eq54 or Eq27

Three groups of mice (n=3×10) were immunised with 1) Eq54 2) Eq27 and 3) non-immunised group where the antigen was replaced with PBS, but still containing the adjuvant.

Figure 4A:
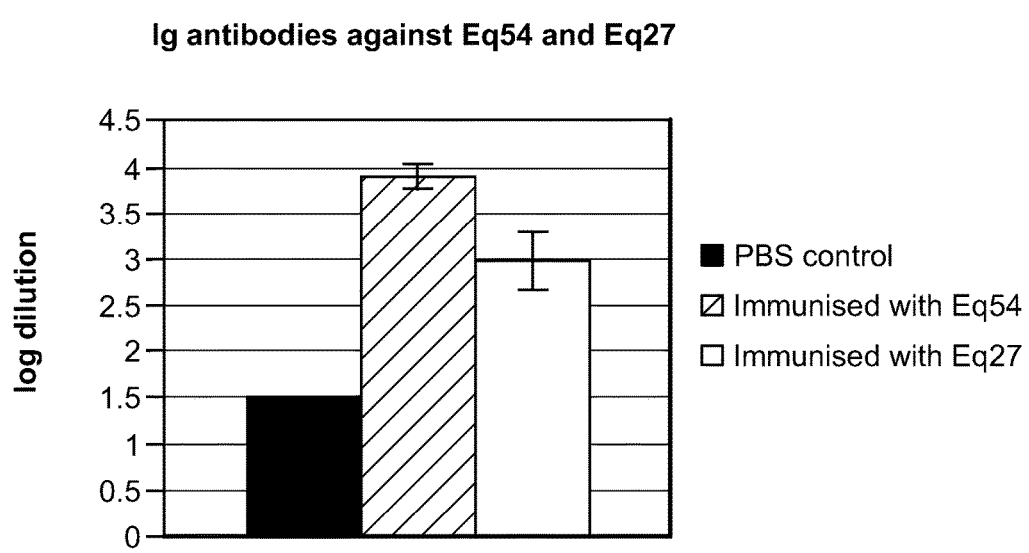
FIG. 4A is a diagram showing antibody titer against Eq54 (n=10) and Eq27. IgG titers in sera from mice immunized with Eq54 or Eq27, or left non-vaccinated are shown. Mean values and standard errors of log values of dilutions required to get an absorbance of 1.5 in ELISA are shown. Values from non-vaccinated mice are included.
Figure 4B:
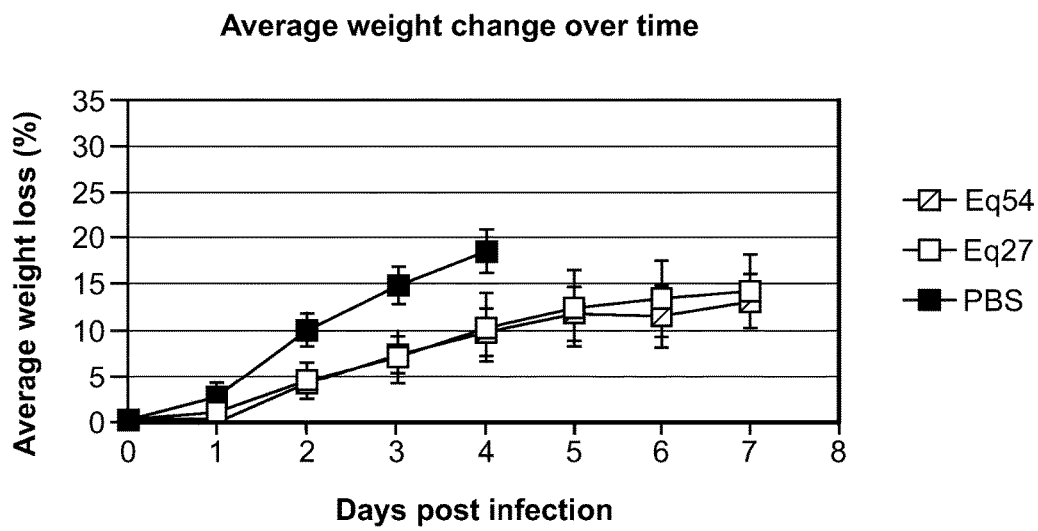
FIG. 4B is a diagram showing weight loss of infected mice. The average weight loss over time of mice infected with *S. equi* subsp. *equi* is shown. Mice (n=3×10) had previously been vaccinated with antigens as indicated. Mean values and standard errors are shown.

A typical sign of infection in mice infected with *S. equi* subsp. *equi* is the loss of weight. The percentage weight loss over time was thus determined. FIG. 4B shows that animals vaccinated with Eq54 or Eq27 were protected from infection, reflected by a milder loss of weight compared with control animals. Animals that lost more than 20% weight were killed. It can be seen in FIG. 4B that non-vaccinated animals lost more weight than the vaccinated animals. On day 2 to 4, $p<0.05$ for Eq54 and for Eq27 compared with controls.

Figure 4C:
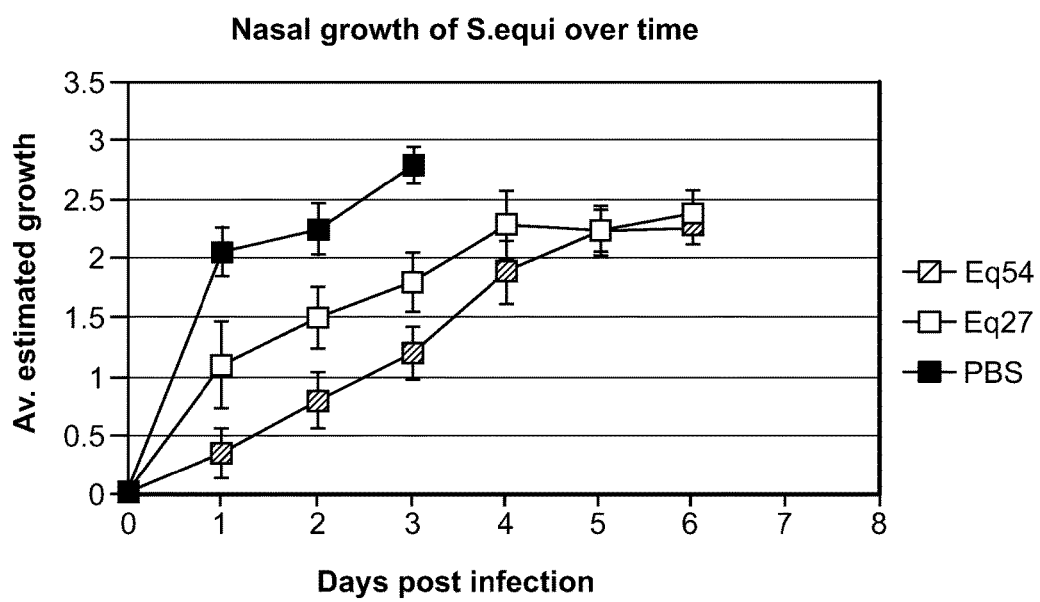
FIG. 4C is a diagram showing nasal colonisation of infected mice. The nasal growth of *S. equi* subsp. *equi* over time of mice infected with *S. equi* subsp. *equi* is shown. Mice (n=3×10) had previously been vaccinated with antigens as indicated. Mean values and standard errors are shown.

Another sign of persistent infection of mice with *S. equi* subsp. *equi* is the colonisation of bacteria in the upper respiratory airways. Nasal growth of *S. equi* was therefore determined daily on a four graded scale. FIG. 4C shows that after 2 to 3 days, the non-vaccinated control animals were heavily colonized with bacteria. Mice vaccinated with Eq54 or Eq27 were significantly ($p<0.05$) less colonized compared with the control group on days 2 and 3.

Example 20

Determination of Antibody Levels in Immunized Mice

Mice were immunized as described above. Serum samples were collected 5 days after last vaccination. Standard Enzyme Linked Immuno Sorbent Assay (ELISA) was used to determine levels of IgG specifically directed against Eq54 and Eq27. Briefly, microliter plates were coated with 100 µl over night at room temperature with either protein at 9 µg/ml in Phosphate Buffered Saline (PBS). Bovine Serum Albumin, 100 µl at 2%, was added (1 hour at 37° C.). The plates were washed with PBS with 0.05% TWEEN™ (polysorbate 20) (PBST). Serum samples were added at serial dilutions, starting at a 40-fold dilution (1 hour at 37° C.) followed by washing. The specific binding of IgG to the antigens was monitored by adding anti mouse IgG antibodies raised in rabbit conjugated with Horse Radish Peroxidase (Sigma Chemical Co, Mo, USA); 100 µl per well at 1000-fold dilution. After washing in PBST, binding of the conjugate was measured by adding OPD substrate according to the instructions provided by the manufacturer (Dako, Glostrup, Denmark). The coloration was determined at 492 nm in a standard ELISA spectrophotometer. The obtained absorbance values were plotted as a function of serum dilution. For each sample, the 10 log values of the dilution required to bring down the absorbance value to 1.5 were determined. I.e., if a sample requires a 2000 fold dilution to give an absorbance of 1.5, a value of 3.30 is assigned to that sample. FIG. 4A shows antibody titers against Eq54 and Eq27 in mice immunized with these antigens.

REFERENCES

1.) Albert, H., Collin, M., Dudziak, D., Ravetch, J. and Nimmerjahn, F. (2008). PNAS 105: 15005-15009.
2.) Allhorn M, and Collin M. Ann N Y Acad Sci. 2009 September; 1173:664-9.
3.) Allhorn, M, Olin, A. I. Nimmerjahn, F. and Collin, M. PLoS ONE (www.plosone.org) January 2008. Issue 1. e1413. Open access.
4.) Allhorn, M., Olsen, A and Collin, M. BMC Microbiology 2008 8:3. (www.biomedcentral.com/1471-2180/8/3) Open access.
5.) Barnham, M., A. Ljunggren, and M. McIntyre. 1987. Epidem. Inf. 98: 183-190.
6.) Bisno A L, Brito M O, Collins C M. (2003) Lancet Infect Dis. Apr.; 3(4):191-200. Review.
7.) Chhatwal G S, McMillan D J. (2005) Trends Mol Med. Apr.; 11(4):152-5. Review.
8.) Collin, M. and Olsén, A. (2001). EMBO J 20:3046-3055.
9.) Coffin M, Olsén A. (2003) Infect Immun. June; 71(6): 2983-92. Review.
10.) Fernandez, E. et al. 2004. Int. J. Syst. Evol. Microbiol. 54: 2291-2296.
11.) Flock, M., Jacobsson, K., Frykberg, L., Hirst, T., R., Franklin, A., Guss, B. and Flock, J.-I. (2004) Infect Immun 72:3228-3236.
12.) Flock M, Karlström Å, Lannergård J, Guss B, Flock J.-I. (2006) Vaccine. May 8; 24(19):4144-51.
13.) Guss, B., Flock, M., Frykberg, L., Waller, A., Robinson, C., Smith, K. and Flock, J.-I.: Available from Nature Precedings <http://hdl.handle.net/10101/npre.2009.2985.1> (2009) Posted 26 Mar. 2009.
14.) Guss B, Flock M, Frykberg L, Waller AS, Robinson C, et al. (2009) PLoS Pathog 5(9): e1000584. doi:10.1371/journal.ppat.1000. Sep. 18, 2009.
15.) Holden M T, Heather Z, Paillot R, Steward K F, Webb K, et al. (2009) PLoS Pathog 5: e1000346.
16.) Hutting, G. et at 2009 FEMS Microbiol Lett. 298:44-50.
17.) Jacobs, A. A, Goovaerts, D., Nuijten, P. J., Theelen, R. P., Hartford, O. M., et al. (2000) Vet Rec 147: 563-567.
18.) Jacobsson, K., Jonsson, H., Lindmark, H., Guss, B., Lindberg, M., and Frykberg. L. (1997) *Microbiol Res*. 152:1-8.
19.) Janulczyk, R. and Rasmussen, M. (2001) Infect Immun 4019-4026.
20.) Jonsson, H., Lindmark, H., and Guss. B. (1995) *Infect Immun* 63:2968-2975.
21.) Karlstróm, Å. et al (2004) Vet Microbiol. December 9; 104(3-4):179-88.
22.) Karlstróm, Å. et al (2006) Vet Microbiol. Apr. 16; 114(1-2):72-81.
23.) Kemp-Symonds J, Kemble T, Waller A (2007) Equine Vet J 39: 284-286.
24.) Lannergård, J. (2006) Potentially virulence-related extracellular proteins of *Streptococcus equi*. (Doctoral thesis) Acta Universitatis Agriculturae Sueciae, Agraria 2006:80. ISBN 91-576-7129-X.
25.) Lannergård, J., Frykberg, L. and Guss B. (2003) FEMS Microbiol. Lett. 222:69-74.
26.) Lannergård, J. and Guss, B. (2006) FEMS Microbiol Lett 262: 230-235.

27.) Lindmark, H. (1999) Characterization of adhesive extracellular proteins from *Streptococcus equi*. (Doctoral thesis) Acta Universitatis Agriculturae Sueciae, Agraria 139. ISBN 91-576-5488-3.
28.) Lindmark, H., and Guss, B. (1999) Infect. Immun. 67: 2383-2388.
29.) Lindmark, H., Jacobsson, K., Frykberg, L., and Guss, B. (1996) Infect Immun 64:3993-3999.
30.) Lindmark, H., Jonsson, P., Olsson-Engvall, E., and Guss, B. (1999) Res Vet Sci. 66:93-99.
31.) Lindmark, H., Nilsson, M., and Guss, B. (2001) Infect immun 69: 3159-3163.
32.) Morein, B. and Lövgren Bengtsson. K. (1998) Immunology and Cellbiology 76:295-299.
33.) Nakata, M. et al (2009) Infect Immun 77:32-44.
34.) Nandakumar, K. S., Collin, M. Olsén, M. et al. 2007. Eur.J. Immunol. 37:2973-2982.
35.) Newton R, Waller A, King, A (2005) Investigation of suspected adverse reactions following strangles vaccination in horses. Vet Rec 156: 291-292.
36.) Rasmussen, M. et al (1999) J Biol Chem 274: 15336-15344.
37.) Schneewind, O., Fowler, A. and Faull, K. F. (1995) Structure of the cell wall anchor of surface proteins in *Staphylococcus aureus*. Science 268:103-106.
38.) Sutcliffe I C, Harrington D J. (2002) Microbiology. Jul.; 148(Pt 7):2065-77.
39.) Sweeney et al (2005) J Vet Int Med 19:123-134.
40.) Timoney J F. (2004) Vet Res. 35:397-409.
41.) Timoney J F, Kumar P (2008) Early pathogenesis of equine *Streptococcus equi* in fection (strangles). Equine Vet J 40: 637-642.
42.) Timoney J F, Qin A, Muthupalani S, Artiushin S (2007) Vaccine potential of novel surface exposed and secreted proteins of *Streptococcus equi*. Vaccine 25: 5583-5590.
43.) Turner C E, et al. (2009) Vaccine. August 6; 27(36): 4923-9. Epub 2009 Jun. 27.
44.) Walker, J. A. and Timoney, J. F. (2002) Vet Microbiol 89:311-321.
45.) Waller, A., Flock, M., Smith, K., Robinson, C., Mitchell, Z., Karlström, Å., Lannergård, J., Bergman, R., Guss, B. and Flock, J.-I. (2007) Vaccine 25: 3629-3635.

The invention claimed is:

1. A method for the production of an antiserum, which method comprises administering an antigenic composition to a non-human mammal host to produce antibodies in said host and recovering antiserum containing said antibodies produced in said host, wherein said antigenic composition comprises a plurality of antigenic components derived from antigens of *Streptococcus equi* subsp. *equi* or subsp. *zooepidemicus*, the antigenic components comprising:

(i) a first fusion polypeptide comprising at least part of a protein designated EAG and at least a part of protein designated CNE , the first fusion polypeptide comprising an amino acid sequence selected from the amino acid sequence as shown in SEQ ID NO: 24 starting from amino acid 12, the amino acid sequence as shown in SEQ ID NO: 28 starting from amino acid 12 and, the amino acid sequence as shown in SEQ ID NO: 34 starting from amino acid 12; and

89

(ii) at least one additional polypeptide selected from
(a) a second fusion polypeptide comprising at least part of a protein designated Eq5 and at least a part of a protein designated Eq8,
(b) a third fusion polypeptide comprising at least part of a protein designated IdeE and at least a part of a protein designated Eq5,
(c) at least part of a protein designated IdeE,
(d) at least part of a protein designated IdeE2,
(e) at least part of a protein designated Eq27,
(f) at least part of a protein designated Eq54,
(g) at least part of a protein of a protein family designated Scl.
wherein each said at least part of said proteins comprises at least one antigenic epitope, and wherein said antigenic composition further comprises at least part of the protein designated EndoSe or EndoSz.

2. A method for the production of an antiserum, which method comprises administering an antigenic composition to a non-human mammal host to produce antibodies in said host and recovering antiserum containing said antibodies produced in said host,
wherein said antigenic composition comprises a plurality of antigenic components derived from antigens of *Streptococcus equi* subsp. *equi* or subsp. *zooepidemicus*, the antigenic components comprising:
(i) a first fusion polypeptide comprising at least part of a protein designated EAG and at least a part of protein designated CNE; and
(ii) a second fusion polypeptide comprising at least part of a protein designated Eq5, at least a part of a protein designated Eq8 which second fusion polypeptide has the amino acid sequence as shown in SEQ ID NO: 22, starting from amino acid 12; and, optionally,
(iii) at least one additional polypeptide selected from
(a) a third fusion polypeptide comprising at least part of a protein designated IdeE and at least a part of a protein designated Eq5,
(b) at least a part of a protein designated EndoSe or a protein designated EndoSz,
(c) at least part of a protein designated IdeE,
(d) at least part of a protein designated IdeE2,
(e) at least part of a protein designated Eq27,
(f) at least part of a protein designated Eq54,
(g) at least part of a protein of a protein family designated Scl.
wherein each said at least part of said proteins comprises at least one antigenic epitope.

3. A method for the production of an antiserum, which method comprises administering an antigenic composition to a non-human mammal host to produce antibodies in said host and recovering antiserum containing said antibodies produced in said host,
wherein said antigenic composition comprises a plurality of antigenic components derived from antigens of *Streptococcus equi* subsp. *equi* or subsp. *zooepidemicus*, the antigenic components comprising:
(i) a first fusion polypeptide comprising at least part of a protein designated EAG and at least a part of protein designated CNE; and
(ii) a third fusion polypeptide comprising at least part of a protein designated IdeE, at least a part of a protein designated Eq5 which third fusion polypeptide has the amino acid sequence as shown in SEQ ID NO: 30, starting at amino acid 12; and, optionally,

90

(iii) at least one additional polypeptide selected from
(a) a second fusion polypeptide comprising at least part of a protein designated Eq5 and at least a part of a protein designated Eq8,
(b) at least a part of a protein designated EndoSe or a protein designated EndoSz,
(c) at least part of a protein designated IdeE,
(d) at least part of a protein designated IdeE2,
(e) at least part of a protein designated Eq27,
(f) at least part of a protein designated Eq54,
(g) at least part of a protein of a protein family designated Scl.
wherein each said at least part of said proteins comprises at least one antigenic epitope.

4. The method for the production of an antiserum according to claims 1 or 3, wherein the second fusion polypeptide comprises the amino acid sequence as shown in SEQ ID NO: 22, starting from amino acid 12.

5. The method for the production of an antiserum according to claims 1 or 2, wherein the third fusion polypeptide comprises the amino acid sequence as shown in SEQ ID NO: 30, starting from amino acid 12.

6. The method for the production of an antiserum according to claims 1, 2 or 3, wherein said antigenic composition comprises (i) a fusion polypeptide comprising the amino acid sequence as shown in SEQ ID NO: 22 starting from amino acid 12, (ii) a fusion polypeptide comprising the amino acid sequence as shown in SEQ ID NO: 24 starting from amino acid 12, and (iii) a polypeptide comprising the amino acid sequence as shown in SEQ ID NO: 26 starting from amino acid 12.

7. The method for the production of an antiserum according to claims 1, 2 or 3, wherein said antigenic composition comprises (i) a fusion polypeptide comprising the amino acid sequence as shown in SEQ ID NO: 28 starting from amino acid 12, (ii) a fusion polypeptide comprising the amino acid sequence as shown in SEQ ID NO: 30 starting from amino acid 12, and (iii) a polypeptide comprising the amino acid sequence as shown in SEQ ID NO: 32 starting from amino acid 12.

8. The method for the production of an antiserum according to claims 1, 2 or 3, wherein said antigenic composition comprises (i) a fusion polypeptide comprising the amino acid sequence as shown in SEQ ID NO: 34 starting from amino acid 12, (ii) a fusion polypeptide comprising the amino acid sequence as shown in SEQ ID NO: 30 starting from amino acid 12, and (iii) a polypeptide comprising the amino acid sequence as shown in SEQ ID NO: 32 starting from amino acid 12.

9. The method for the production of an antiserum according to claims 1, 2 or 3, wherein said antigenic composition comprises (i) a fusion polypeptide comprising the amino acid sequence as shown in SEQ ID NO: 34 starting from amino acid 12, and (ii) a fusion polypeptide comprising the amino acid sequence as shown in SEQ ID NO: 30 starting from amino acid 12.

10. The method for the production of an antiserum according to claims 1, 2 or 3 wherein said antigenic composition comprises at least one an antigenic fusion polypeptide comprising the amino acid sequence as shown in SEQ ID NO: 22, starting from amino acid 12; an antigenic fusion polypeptide comprising the amino acid sequence as shown in SEQ ID NO: 24, starting from amino acid 12; an antigenic fusion polypeptide comprising the amino acid sequence as shown in SEQ ID NO: 28, starting from amino acid 12; an antigenic fusion polypeptide comprising the amino acid sequence as shown in SEQ ID NO: 30, starting from amino acid 12; an antigenic fusion polypeptide comprising the amino acid sequence as shown in SEQ ID NO: 34, starting from amino acid 12.

11. A method of prophylactic or therapeutic treatment of *Streptococcus equi* infection in a mammal, comprising administering to said mammal an immunologically effective amount of a vaccine composition, which comprises an antigenic composition comprising a plurality of antigenic components derived from antigens of *Streptococcus equi* subsp. *equi* or subsp. *zooepidemicus*, the antigenic components comprising:
(i) a first fusion polypeptide comprising at least part of a protein designated EAG and at least a part of protein designated CNE, the first fusion polypeptide comprising an amino acid sequence selected from the amino acid sequence as shown in SEQ ID NO: 24 starting from amino acid 12, the amino acid sequence as shown in SEQ ID NO: 28 starting from amino acid 12 and, the amino acid sequence as shown in SEQ ID NO: 34 starting from amino acid 12; and
(ii) at least one additional polypeptide selected from
(a) a second fusion polypeptide comprising at least part of a protein designated Eq5 and at least a part of a protein designated Eq8,
(b) a third fusion polypeptide comprising at least part of a protein designated IdeE and at least a part of a protein designated Eq5,
(c) at least a part of a protein designated EndoSe or a protein designated EndoSz,
(d) at least part of a protein designated IdeE,
(e) at least part of a protein designated IdeE2,
(f) at least part of a protein designated Eq27,
(g) at least part of a protein designated Eq54,
(h) at least part of a protein of a protein family designated Scl.
wherein each said at least part of said proteins comprises at least one antigenic epitope; and a pharmaceutically acceptable carrier.

12. A method of prophylactic or therapeutic treatment of *Streptococcus equi* infection in a mammal, comprising administering to said mammal an immunologically effective amount of a vaccine composition, which comprises an antigenic composition comprising a plurality of antigenic components derived from antigens of *Streptococcus equi* subsp. *equi* or subsp. *zooepidemicus*, the antigenic components comprising:
(i) a first fusion polypeptide comprising at least part of a protein designated EAG and at least a part of protein designated CNE; and
(ii) a second fusion polypeptide comprising at least part of a protein designated Eq5 at least a part of a protein designated Eq8 which second fusion polypeptide has the amino acid sequence as shown in SEQ ID NO: 22, starting from amino acid 12; and, optionally,
(iii) at least one additional polypeptide selected from
(a) a third fusion polypeptide comprising at least part of a protein designated IdeE and at least a part of a protein designated Eq5,
(b) at least a part of a protein designated EndoSe or a protein designated EndoSz,
(c) at least part of a protein designated IdeE,
(d) at least part of a protein designated IdeE2,
(e) at least part of a protein designated Eq27,
(f) at least part of a protein designated Eq54,
(g) at least part of a protein of a protein family designated Scl.
wherein each said at least part of said proteins comprises at least one antigenic epitope;
and a pharmaceutically acceptable carrier.

13. A method of prophylactic or therapeutic treatment of *Streptococcus equi* infection in a mammal, comprising administering to said mammal an immunologically effective amount of a vaccine composition, which comprises an antigenic composition comprising a plurality of antigenic components derived from antigens of *Streptococcus equi* subsp. *equi* or subsp. *zooepidemicus*, the antigenic components comprising:
(i) a first fusion polypeptide comprising at least part of a protein designated EAG and at least a part of protein designated CNE; and
(ii) a third fusion polypeptide comprising at least part of a protein designated IdeE, at least a part of a protein designated Eq5 which third fusion polypeptide has the amino acid sequence as shown in SEQ ID NO: 30, starting from amino acid 12; and, optionally,
(iii) at least one additional polypeptide selected from
(a) a second fusion polypeptide comprising at least part of a protein designated Eq5 and at least a part of a protein designated Eq8,
(b) at least a part of a protein designated EndoSe or a protein designated EndoSz,
(c) at least part of a protein designated IdeE,
(d) at least part of a protein designated IdeE2,
(e) at least part of a protein designated Eq27,
(f) at least part of a protein designated Eq54,
(g) at least part of a protein of a protein family designated Scl.
wherein each said at least part of said proteins comprises at least one antigenic epitope; and a pharmaceutically acceptable carrier.

14. The method of prophylactic or therapeutic treatment according to claims 11, 12 or 13, wherein said at least one additional polypeptide comprises the second fusion polypeptide in claim 1, and at least part of the protein designated IdeE.

15. The method of prophylactic or therapeutic treatment according to claims 11 or 13, wherein the second fusion polypeptide comprises the amino acid sequence as shown in SEQ ID NO: 22, starting from amino acid 12.

16. The method of prophylactic or therapeutic treatment according to claims 11, or 12, wherein the third fusion polypeptide comprises the amino acid sequence as shown in SEQ ID NO: 30, starting from amino acid 12.

17. The method of prophylactic or therapeutic treatment according to claims 11, 12 or 13, wherein said antigenic composition comprises (i) a fusion polypeptide comprising the amino acid sequence as shown in SEQ ID NO: 22 starting from amino acid 12, (ii) a fusion polypeptide comprising the amino acid sequence as shown in SEQ ID NO: 24 starting from amino acid 12, and (iii) a polypeptide comprising the amino acid sequence as shown in SEQ ID NO: 26 starting from amino acid 12.

18. The method of prophylactic or therapeutic treatment according to claims 11, 12 or 13, wherein said antigenic composition comprises (i) a fusion polypeptide comprising the amino acid sequence as shown in SEQ ID NO: 28 starting from amino acid 12, (ii) a fusion polypeptide comprising the amino acid sequence as shown in SEQ ID NO: 30 starting from amino acid 12, and (iii) a polypeptide comprising the amino acid sequence as shown in SEQ ID NO: 32 starting from amino acid 12.

19. The method of prophylactic or therapeutic treatment according to claims 11, 12 or 13, wherein said antigenic composition comprises (i) a fusion polypeptide comprising the amino acid sequence as shown in SEQ ID NO: 34 starting from amino acid 12, (ii) a fusion polypeptide comprising the amino acid sequence as shown in SEQ ID NO: 30 starting from amino acid 12, and (iii) a polypeptide comprising the amino acid sequence as shown in SEQ ID NO: 32 starting from amino acid 12.

20. The method of prophylactic or therapeutic treatment according to claims 11, 12 or 13, wherein said antigenic composition comprises (i) a fusion polypeptide comprising the amino acid sequence as shown in SEQ ID NO: 34 starting from amino acid 12, and (ii) a fusion polypeptide comprising the amino acid sequence as shown in SEQ ID NO: 30 starting from amino acid 12.

21. The method of prophylactic or therapeutic treatment according to claims 11, 12 or 13, wherein said antigenic composition comprises at least one an antigenic fusion polypeptide comprising the amino acid sequence as shown in SEQ ID NO: 22, starting from amino acid 12; an antigenic fusion polypeptide comprising the amino acid sequence as shown in SEQ ID NO: 24, starting from amino acid 12; an antigenic fusion polypeptide comprising the amino acid sequence as shown in SEQ ID NO: 28, starting from amino acid 12; an antigenic fusion polypeptide comprising the amino acid sequence as shown in SEQ ID NO: 30, starting from amino acid 12; an antigenic fusion polypeptide comprising the amino acid sequence as shown in SEQ ID NO: 34, starting from amino acid 12.

22. A method of protecting horses against *Streptococcus equi* infection, which comprises inoculating a horse subcutaneously, intradermally, intramuscularly or intranasally with a vaccine composition of claims 11, 12 or 13, to induce an immune response against *Streptococcus equi* in said horse.

23. The method of claim 22, wherein an immune response in the form of IgG and/or IgA and/or IgM antibodies in serum and/or the nasopharyngeal mucus is induced in said horse.

24. The method of claims 11, 12 or 13, wherein said mammal is a horse.

* * * * *

SEQUENCE LISTING

```
<160> NUMBER OF SEQ ID NOS: 42

<210> SEQ ID NO 1
<211> LENGTH: 33
<212> TYPE: DNA
<213> ORGANISM: Artificial Sequence
<220> FEATURE:
<223> OTHER INFORMATION: PCR primer

<400> SEQUENCE: 1
ggttggatcc actaatctta gtgacaacat cac                                     33

<210> SEQ ID NO 2
<211> LENGTH: 32
<212> TYPE: DNA
<213> ORGANISM: Artificial Sequence
<220> FEATURE:
<223> OTHER INFORMATION: PCR primer

<400> SEQUENCE: 2
tccagagctc cttgacagta aagctggtat ag                                      32

<210> SEQ ID NO 3
<211> LENGTH: 28
<212> TYPE: DNA
<213> ORGANISM: Artificial Sequence
<220> FEATURE:
<223> OTHER INFORMATION: PCR primer

<400> SEQUENCE: 3
agtggagctc ttagacgcag caacagtg                                           28

<210> SEQ ID NO 4
<211> LENGTH: 35
<212> TYPE: DNA
<213> ORGANISM: Artificial Sequence
<220> FEATURE:
<223> OTHER INFORMATION: PCR primer

<400> SEQUENCE: 4
caccctcgag ttatttggct ttgttgatta aggtc                                   35

<210> SEQ ID NO 5
```

```
<211> LENGTH: 29
<212> TYPE: DNA
<213> ORGANISM: Artificial Sequence
<220> FEATURE:
<223> OTHER INFORMATION: PCR primer

<400> SEQUENCE: 5
cgtagagctc tcggaaccca atccatatc                                             29

<210> SEQ ID NO 6
<211> LENGTH: 29
<212> TYPE: DNA
<213> ORGANISM: Artificial Sequence
<220> FEATURE:
<223> OTHER INFORMATION: PCR primer

<400> SEQUENCE: 6
gaggtctaga aggaccttgt ttgccattt                                             29

<210> SEQ ID NO 7
<211> LENGTH: 28
<212> TYPE: DNA
<213> ORGANISM: Artificial Sequence
<220> FEATURE:
<223> OTHER INFORMATION: PCR primer

<400> SEQUENCE: 7
agcatctaga ttatctggtc cgccagga                                              28

<210> SEQ ID NO 8
<211> LENGTH: 30
<212> TYPE: DNA
<213> ORGANISM: Artificial Sequence
<220> FEATURE:
<223> OTHER INFORMATION: PCR primer

<400> SEQUENCE: 8
gaggctgcag tggacctcgg gtaccgcctt                                            30

<210> SEQ ID NO 9
<211> LENGTH: 29
<212> TYPE: DNA
<213> ORGANISM: Artificial Sequence
<220> FEATURE:
<223> OTHER INFORMATION: PCR primer

<400> SEQUENCE: 9
agtactgcag gaccagccag cagcactaa                                             29

<210> SEQ ID NO 10
<211> LENGTH: 31
<212> TYPE: DNA
<213> ORGANISM: Artificial Sequence
<220> FEATURE:
<223> OTHER INFORMATION: PCR primer

<400> SEQUENCE: 10
tgcagagctc tggcttttgg gcagcttctt c                                          31

<210> SEQ ID NO 11
<211> LENGTH: 29
<212> TYPE: DNA
<213> ORGANISM: Artificial Sequence
<220> FEATURE:
<223> OTHER INFORMATION: PCR primer

<400> SEQUENCE: 11
```

```
catgggatcc gcgactaccc tagcaggac                                    29
```

<210> SEQ ID NO 12
<211> LENGTH: 31
<212> TYPE: DNA
<213> ORGANISM: Artificial Sequence
<220> FEATURE:
<223> OTHER INFORMATION: PCR primer

<400> SEQUENCE: 12

```
ctagccatgg gtgcttaagc ttttcaatct g                                 31
```

<210> SEQ ID NO 13
<211> LENGTH: 30
<212> TYPE: DNA
<213> ORGANISM: Artificial Sequence
<220> FEATURE:
<223> OTHER INFORMATION: PCR primer

<400> SEQUENCE: 13

```
agtaccatgg gaaacgacta ctgctagtgc                                   30
```

<210> SEQ ID NO 14
<211> LENGTH: 31
<212> TYPE: DNA
<213> ORGANISM: Artificial Sequence
<220> FEATURE:
<223> OTHER INFORMATION: PCR primer

<400> SEQUENCE: 14

```
ctggctcgag ttatttagca accaaggctg c                                 31
```

<210> SEQ ID NO 15
<211> LENGTH: 33
<212> TYPE: DNA
<213> ORGANISM: Artificial Sequence
<220> FEATURE:
<223> OTHER INFORMATION: PCR primer

<400> SEQUENCE: 15

```
tactggatcc gacgattacc aaaggaatgc tac                               33
```

<210> SEQ ID NO 16
<211> LENGTH: 32
<212> TYPE: DNA
<213> ORGANISM: Artificial Sequence
<220> FEATURE:
<223> OTHER INFORMATION: PCR primer

<400> SEQUENCE: 16

```
tgatctcgag ttagctcagt ttctgccata tg                                32
```

<210> SEQ ID NO 17
<211> LENGTH: 32
<212> TYPE: DNA
<213> ORGANISM: Artificial Sequence
<220> FEATURE:
<223> OTHER INFORMATION: PCR primer

<400> SEQUENCE: 17

```
gtcggatccg aggataaggt tgtgcaaact ag                                32
```

<210> SEQ ID NO 18
<211> LENGTH: 32
<212> TYPE: DNA

<210> SEQ ID NO 18
<211> LENGTH: 32
<212> TYPE: DNA
<213> ORGANISM: Artificial Sequence
<220> FEATURE:
<223> OTHER INFORMATION: PCR primer

<400> SEQUENCE: 18
gcctctcgag ggataagcta gtctgtcttt gg                          32

<210> SEQ ID NO 19
<211> LENGTH: 33
<212> TYPE: DNA
<213> ORGANISM: Artificial Sequence
<220> FEATURE:
<223> OTHER INFORMATION: PCR primer

<400> SEQUENCE: 19
ggcagagctc gatacagcaa gctataccat cac                         33

<210> SEQ ID NO 20
<211> LENGTH: 35
<212> TYPE: DNA
<213> ORGANISM: Artificial Sequence
<220> FEATURE:
<223> OTHER INFORMATION: PCR primer

<400> SEQUENCE: 20
tatttctaga agttttatag gtgaaaacga taacc                       35

<210> SEQ ID NO 21
<211> LENGTH: 1961
<212> TYPE: DNA
<213> ORGANISM: Artificial Sequence
<220> FEATURE:
<223> OTHER INFORMATION: Recombinant gene fusion fragment

<400> SEQUENCE: 21
tctgttccag gggcccctgg gatccgcgac taccctagca ggacaaacag aagtacgggc    60
tgataatatc ttacgcttag atatgacaga taaagaagca gttgaaaaat tcgctaacga   120
gcttaaaaat gaagtccata aaaactatcg tggtagtaat acttggcaaa agcttaccct   180
tatacttaat ggttatcaaa accttagaga acaaatagag accgagctaa aaatagtga    240 acaaaaagta aagagcttaa tgataaggt taatagtgaa actcaaggaa acaagagtt    300 acagaatcag cttgagaaag aaaagaagaa gttagaaaca ctaaaaaaag agcttgaagc   360
tgagaaggct aaaggaactg agaaacaga gaagcttcaa aaggaaattg aagcaaaaaa    420
tgcaatgatt tctgacctac aaaaacagct gaggaaact aagcaaaggg ttcaagagtt     480
tgaagctgaa gtaggtaaat taatggccga aaaggcagac ctacaaacaa aattaaatga    540
acaagagcag cttaacgcta agcttcaaaa agaaattgaa gacttaaagg ctcagattga    600
aaagcttaag cacccatggg aaacgactac tgctagtgca tttgaaaata atgggacagg    660
tcaacatctg aactggcaca tagatattcc acaagaatat acagttgaat taggagaacc    720
aattactatc tcagatctta tgagtcaaat tacggttact cgtaaaggta gtaatgggac    780
tgttaatgat ggagatactt ttgactttat ttcgaatgga gatggttcaa gaggaattga    840 taccccctgga gtaaaaatat ggtttgactt ttacaatgct gcgggtactt ccttttaac    900 tgatgaaatg ttagcttcgc ctacatatgc tgtaccgggg ggatcttata ctattaaagc    960
ttgggtattc tatgggaaaa atgataccaa aaagctcttc acatttaaac taaaaaattc   1020
caacagcaat aaaactgagt taaggaagtc gttagaggag gctaagctaa aactcagcca   1080
gcctgaagga acgtattctg atgaatcact gcaagccttg caatcagcgg ttactattgg   1140

```
taagacctat ttaaacagtg accctgatca aaatacagta gatcaatctg ttactactat   1200
tgattccgct attactagtc ttgttaatct taatgcttta aatgaagcta ttaatcaagc   1260
tacacctttt ataacagatg gcaaagagta tcctaaagaa gcgtatgacg gtcttgtgca   1320
aaagcttgca gcggcagcta agcttcaaaa ttcatttggt ccttcacaag agatgttga    1380 taaggctgcg actgatttaa cgcaagctct tacgacgctt aagactgctg tagcgcatga   1440
agccttagat caagccttgg ctaagctgtt agagctttac cgagaaaatc caaatcttgc   1500
tttgacatca gagtctttga aggaattgta caataaggcc attgaagcag caggtacctt   1560
ctatagaact gttaacaagg ataaagagag aaaagacatt tccctttatg agctagagcg   1620
ctacactaca gaaacaaatt cagttgttga tactatttta aaggtaaagg ctgcgattgc   1680
cgaagaagga aaggcaaaat tgcgttctgc tttagaccaa ttaaatgctc ttatcggaga   1740
aaatctagac ctatctccat atacagcagc ttctgctcaa gcctatacag accagctagc   1800
taaggctaag gaggtcgcag cagcgggtga gacagcttat gctcaggaga cagaaccgac   1860
agctattact aacagcttgg ttaaggtgtt aaatgctaag aaatccctct cagatgccaa   1920
ggcagccttg gttgctaaat aactcgagcg gccgcatcgt g                       1961
```

<210> SEQ ID NO 22
<211> LENGTH: 649
<212> TYPE: PRT
<213> ORGANISM: Artificial Sequence
<220> FEATURE:
<223> OTHER INFORMATION: Recombinant fusion protein

<400> SEQUENCE: 22

```
Leu Glu Val Leu Phe Gln Gly Pro Leu Gly Ser Ala Thr Thr Leu Ala
1               5                   10                  15

Gly Gln Thr Glu Val Arg Ala Asp Asn Ile Leu Arg Leu Asp Met Thr
            20                  25                  30

Asp Lys Glu Ala Val Glu Lys Phe Ala Asn Glu Leu Lys Asn Glu Val
        35                  40                  45

His Lys Asn Tyr Arg Gly Ser Asn Thr Trp Gln Lys Leu Thr Leu Ile
    50                  55                  60

Leu Asn Gly Tyr Gln Asn Leu Arg Glu Gln Ile Glu Thr Glu Leu Lys
65                  70                  75                  80

Asn Ser Glu Gln Lys Val Lys Glu Leu Asn Asp Lys Val Asn Ser Glu
                85                  90                  95

Thr Gln Gly Lys Gln Glu Leu Gln Asn Gln Leu Glu Lys Glu Lys Glu
            100                 105                 110

Glu Leu Glu Thr Leu Lys Lys Glu Leu Glu Ala Glu Lys Ala Lys Gly
        115                 120                 125

Thr Gly Glu Thr Glu Lys Leu Gln Lys Glu Ile Glu Ala Lys Asn Ala
    130                 135                 140

Met Ile Ser Asp Leu Gln Lys Gln Leu Glu Glu Thr Lys Gln Arg Val
145                 150                 155                 160

Gln Glu Phe Glu Ala Glu Val Gly Lys Leu Met Ala Glu Lys Ala Asp
                165                 170                 175

Leu Gln Thr Lys Leu Asn Glu Gln Gln Leu Asn Ala Lys Leu Gln
            180                 185                 190

Lys Glu Ile Glu Asp Leu Lys Ala Gln Ile Glu Lys Leu Lys His Pro
        195                 200                 205

Trp Glu Thr Thr Thr Ala Ser Ala Phe Glu Asn Asn Gly Thr Gly Gln
```

-continued

```
                210                 215                 220
His Leu Asn Trp His Ile Asp Ile Pro Gln Glu Tyr Thr Val Glu Leu
225                 230                 235                 240

Gly Glu Pro Ile Thr Ile Ser Asp Leu Met Ser Gln Ile Thr Val Thr
                245                 250                 255

Arg Lys Gly Ser Asn Gly Thr Val Asn Asp Gly Asp Thr Phe Asp Phe
                260                 265                 270

Ile Ser Asn Gly Asp Gly Ser Arg Gly Ile Asp Thr Pro Gly Val Lys
                275                 280                 285

Ile Trp Phe Asp Phe Tyr Asn Ala Ala Gly Thr Ser Phe Leu Thr Asp
                290                 295                 300

Glu Met Leu Ala Ser Pro Thr Tyr Ala Val Pro Gly Gly Ser Tyr Thr
305                 310                 315                 320

Ile Lys Ala Trp Val Phe Tyr Gly Lys Asn Asp Thr Lys Lys Leu Phe
                325                 330                 335

Thr Phe Lys Leu Lys Asn Ser Asn Ser Asn Lys Thr Glu Leu Arg Lys
                340                 345                 350

Ser Leu Glu Glu Ala Lys Leu Lys Leu Ser Gln Pro Glu Gly Thr Tyr
                355                 360                 365

Ser Asp Glu Ser Leu Gln Ala Leu Gln Ser Ala Val Thr Ile Gly Lys
                370                 375                 380

Thr Tyr Leu Asn Ser Asp Pro Asp Gln Asn Thr Val Asp Gln Ser Val
385                 390                 395                 400

Thr Thr Ile Asp Ser Ala Ile Thr Ser Leu Val Asn Leu Asn Ala Leu
                405                 410                 415

Asn Glu Ala Ile Asn Gln Ala Thr Pro Phe Ile Thr Asp Gly Lys Glu
                420                 425                 430

Tyr Pro Lys Glu Ala Tyr Asp Gly Leu Val Gln Lys Leu Ala Ala Ala
                435                 440                 445

Ala Lys Leu Gln Asn Ser Phe Gly Pro Ser Gln Gly Asp Val Asp Lys
                450                 455                 460

Ala Ala Thr Asp Leu Thr Gln Ala Leu Thr Thr Leu Lys Thr Ala Val
465                 470                 475                 480

Ala His Glu Ala Leu Asp Gln Ala Leu Ala Lys Leu Leu Glu Leu Tyr
                485                 490                 495

Arg Glu Asn Pro Asn Leu Ala Leu Thr Ser Glu Ser Leu Lys Glu Leu
                500                 505                 510

Tyr Asn Lys Ala Ile Glu Ala Ala Gly Thr Phe Tyr Arg Thr Val Asn
                515                 520                 525

Lys Asp Lys Glu Arg Lys Asp Ile Ser Leu Tyr Glu Leu Glu Arg Tyr
                530                 535                 540

Thr Thr Glu Thr Asn Ser Val Val Asp Thr Ile Leu Lys Val Lys Ala
545                 550                 555                 560

Ala Ile Ala Glu Glu Gly Lys Ala Lys Leu Arg Ser Ala Leu Asp Gln
                565                 570                 575

Leu Asn Ala Leu Ile Gly Glu Asn Leu Asp Leu Ser Pro Tyr Thr Ala
                580                 585                 590

Ala Ser Ala Gln Ala Tyr Thr Asp Gln Leu Ala Lys Ala Lys Glu Val
                595                 600                 605

Ala Ala Ala Gly Glu Thr Ala Tyr Ala Gln Glu Thr Glu Pro Thr Ala
                610                 615                 620

Ile Thr Asn Ser Leu Val Lys Val Leu Asn Ala Lys Lys Ser Leu Ser
625                 630                 635                 640
```

Asp Ala Lys Ala Ala Leu Val Ala Lys
            645

<210> SEQ ID NO 23
<211> LENGTH: 1962
<212> TYPE: DNA
<213> ORGANISM: Artificial Sequence
<220> FEATURE:
<223> OTHER INFORMATION: Recombinant gene fusion fragment

<400> SEQUENCE: 23

| | |
|---|---:|
| ctggaagttc tgttccaggg gcccctggga tccactaatc ttagtgacaa catcacatca | 60 |
| ttgacggttg cttcttcatc actccgagat ggagagagaa cgacggtaaa ggttgcgttt | 120 |
| gatgacaaaa aacagaaaat caaggcaggg gatacgatag aggtcacctg gcctacaagt | 180 |
| ggtaatgtct acattcaggg ctttaataaa accataccgc ttaatattag aggggtagat | 240 |
| gttggtacct tggaggtcac gctagacaag gctgttttca cattcaatca aaatattgaa | 300 |
| acaatgcatg atgtctctgg ttggggagag tttgatatta ctgttagaaa tgtgacacaa | 360 |
| accaccgctg aaacatcagg aacgaccaca gtaaaggtag caatcgcac tgctactatc | 420 |
| actgttacta agcctgaggc aggcactggt accagctcat tttattataa gactggtgat | 480 |
| atgcagccca tgatactga gcgtgtgaga tggttcctgc tgattaacaa caacaaggaa | 540 |
| tgggtggcca atactgttac agtcgaagac gatattcaag gtggtcaaac cttggatatg | 600 |
| agcagctttg acatcaccgt atctggttat cgtaacgagc gcttcgttgg ggaaaacgct | 660 |
| ctgacagagt ttcatacaac atttccaaat tctgtcatta cggcaacaga taatcacatt | 720 |
| agtgtgcggt tagatcaata tgatgcctca caaaacactg tcaacattgc ttataagaca | 780 |
| aagataacgg actttgacca aaagaatttt gccaacaaca gtaaaatctg gtaccagatt | 840 |
| ttatacaagg atcaggtatc gggtcaagag tcaaaccacc aagtagccaa tatcaatgct | 900 |
| aacggcgggg ttgatggcag tcgctatacc agctttactg tcaaggagct ctcggaaccc | 960 |
| aatccatatc agatgtgag gcgtttcctt gatgagaagt acgatggaga tgtggataaa | 1020 |
| ttatctaaac aacttcaagg ttattttggt agtttaagag agtatataga gtttgaactt | 1080 |
| aaaaatggca acaaggtcc ttctagatta tctggtccgc caggatacc acttactcgt | 1140 |
| gatttctccc gtaacttcct agaagaaaat actgcaaaat attagatca attaagagaa | 1200 |
| catctacagc acagatttag tgaacttgag agcttaacaa gaaaattaga gaagaaggc | 1260 |
| ggtacccgag gtccactgca ggaccagcca gcagcactaa aatatccaga acctagagac | 1320 |
| tattttcttc atactcgtga aggtgatgtt atttatgatg aggatataaa aagatatttt | 1380 |
| gaggatttag aagcctattt aacagctaga cttggtggga ttgataaaaa agtagaagaa | 1440 |
| gctgcccaaa agccagagct cttagacgca gcaacagtgt tagagcctac aacagccttc | 1500 |
| attagagaag ctgttaggga aatcaatcag ctgagtgatg actacgctga caatcaagag | 1560 |
| cttcaggctg ttcttgctaa tgctggagtt gaggcacttg ctgcagatac tgttgatcag | 1620 |
| gctaaagcag ctcttgacaa agcaaaggca gctgttgctg gtgttcagct tgatgaagca | 1680 |
| agacgtgagg cttacagaac aatcaatgcc ttaagtgatc agcacaaaag cgatcaaaag | 1740 |
| gttcagctag ctctagttgc tgcagcagct aaggtggcag atgctgcttc agttgatcaa | 1800 |
| gtgaatgcag ccattaatga tgctcataca gctattgcgg acattacagg agcagccttg | 1860 |
| ttggaggcta aagaagctgc tatcaatgaa ctaaagcagt atggcattag tgattactat | 1920 |
| gtgaccttaa tcaacaaagc caaataactc gagcggccgc at | 1962 |

```
<210> SEQ ID NO 24
<211> LENGTH: 648
<212> TYPE: PRT
<213> ORGANISM: Artificial Sequence
<220> FEATURE:
<223> OTHER INFORMATION: Recombinant fusion protein

<400> SEQUENCE: 24
```

| | | | | | | | | | | | | | | | |
|---|---|---|---|---|---|---|---|---|---|---|---|---|---|---|---|
| Leu | Glu | Val | Leu | Phe | Gln | Gly | Pro | Leu | Gly | Ser | Thr | Asn | Leu | Ser | Asp |
| 1 | | | | 5 | | | | | 10 | | | | | 15 | |
| Asn | Ile | Thr | Ser | Leu | Thr | Val | Ala | Ser | Ser | Leu | Arg | Asp | Gly | Glu | |
| | | | 20 | | | | | 25 | | | | | 30 | | |
| Arg | Thr | Thr | Val | Lys | Val | Ala | Phe | Asp | Asp | Lys | Lys | Gln | Lys | Ile | Lys |
| | | 35 | | | | | 40 | | | | | 45 | | | |
| Ala | Gly | Asp | Thr | Ile | Glu | Val | Thr | Trp | Pro | Thr | Ser | Gly | Asn | Val | Tyr |
| 50 | | | | | 55 | | | | | 60 | | | | | |
| Ile | Gln | Gly | Phe | Asn | Lys | Thr | Ile | Pro | Leu | Asn | Ile | Arg | Gly | Val | Asp |
| 65 | | | | | 70 | | | | | 75 | | | | | 80 |
| Val | Gly | Thr | Leu | Glu | Val | Thr | Leu | Asp | Lys | Ala | Val | Phe | Thr | Phe | Asn |
| | | | | 85 | | | | | 90 | | | | | 95 | |
| Gln | Asn | Ile | Glu | Thr | Met | His | Asp | Val | Ser | Gly | Trp | Gly | Glu | Phe | Asp |
| | | | 100 | | | | | 105 | | | | | 110 | | |
| Ile | Thr | Val | Arg | Asn | Val | Thr | Gln | Thr | Thr | Ala | Glu | Thr | Ser | Gly | Thr |
| | | 115 | | | | | 120 | | | | | 125 | | | |
| Thr | Thr | Val | Lys | Val | Gly | Asn | Arg | Thr | Ala | Thr | Ile | Thr | Val | Thr | Lys |
| 130 | | | | | 135 | | | | | 140 | | | | | |
| Pro | Glu | Ala | Gly | Thr | Gly | Thr | Ser | Ser | Phe | Tyr | Tyr | Lys | Thr | Gly | Asp |
| 145 | | | | | 150 | | | | | 155 | | | | | 160 |
| Met | Gln | Pro | Asn | Asp | Thr | Glu | Arg | Val | Arg | Trp | Phe | Leu | Leu | Ile | Asn |
| | | | | 165 | | | | | 170 | | | | | 175 | |
| Asn | Asn | Lys | Glu | Trp | Val | Ala | Asn | Thr | Val | Thr | Val | Glu | Asp | Asp | Ile |
| | | | 180 | | | | | 185 | | | | | 190 | | |
| Gln | Gly | Gly | Gln | Thr | Leu | Asp | Met | Ser | Ser | Phe | Asp | Ile | Thr | Val | Ser |
| | | 195 | | | | | 200 | | | | | 205 | | | |
| Gly | Tyr | Arg | Asn | Glu | Arg | Phe | Val | Gly | Glu | Asn | Ala | Leu | Thr | Glu | Phe |
| 210 | | | | | 215 | | | | | 220 | | | | | |
| His | Thr | Thr | Phe | Pro | Asn | Ser | Val | Ile | Thr | Ala | Thr | Asp | Asn | His | Ile |
| 225 | | | | | 230 | | | | | 235 | | | | | 240 |
| Ser | Val | Arg | Leu | Asp | Gln | Tyr | Asp | Ala | Ser | Gln | Asn | Thr | Val | Asn | Ile |
| | | | | 245 | | | | | 250 | | | | | 255 | |
| Ala | Tyr | Lys | Thr | Lys | Ile | Thr | Asp | Phe | Asp | Gln | Lys | Glu | Phe | Ala | Asn |
| | | | 260 | | | | | 265 | | | | | 270 | | |
| Asn | Ser | Lys | Ile | Trp | Tyr | Gln | Ile | Leu | Tyr | Lys | Asp | Gln | Val | Ser | Gly |
| | | 275 | | | | | 280 | | | | | 285 | | | |
| Gln | Glu | Ser | Asn | His | Gln | Val | Ala | Asn | Ile | Asn | Ala | Asn | Gly | Gly | Val |
| | 290 | | | | | 295 | | | | | 300 | | | | |
| Asp | Gly | Ser | Arg | Tyr | Thr | Ser | Phe | Thr | Val | Lys | Glu | Leu | Ser | Glu | Pro |
| 305 | | | | | 310 | | | | | 315 | | | | | 320 |
| Asn | Pro | Tyr | Pro | Asp | Val | Arg | Arg | Phe | Leu | Asp | Glu | Lys | Tyr | Asp | Gly |
| | | | | 325 | | | | | 330 | | | | | 335 | |
| Asp | Val | Asp | Lys | Leu | Ser | Lys | Gln | Leu | Gln | Gly | Tyr | Phe | Gly | Ser | Leu |
| | | | 340 | | | | | 345 | | | | | 350 | | |
| Arg | Glu | Tyr | Ile | Glu | Phe | Glu | Leu | Lys | Asn | Gly | Lys | Gln | Gly | Pro | Ser |
| | | 355 | | | | | 360 | | | | | 365 | | | |

```
Arg Leu Ser Gly Pro Pro Gly Tyr Pro Leu Thr Arg Asp Phe Ser Arg
    370                 375                 380

Asn Phe Leu Glu Glu Asn Thr Ala Lys Tyr Leu Asp Gln Leu Arg Glu
385                 390                 395                 400

His Leu Gln His Arg Phe Ser Glu Leu Glu Ser Leu Thr Arg Lys Leu
                405                 410                 415

Glu Lys Glu Gly Gly Thr Arg Gly Pro Leu Gln Asp Gln Pro Ala Ala
            420                 425                 430

Leu Lys Tyr Pro Glu Pro Arg Asp Tyr Phe Leu His Thr Arg Glu Gly
        435                 440                 445

Asp Val Ile Tyr Asp Glu Asp Ile Lys Arg Tyr Phe Glu Asp Leu Glu
450                 455                 460

Ala Tyr Leu Thr Ala Arg Leu Gly Gly Ile Asp Lys Lys Val Glu Glu
465                 470                 475                 480

Ala Ala Gln Lys Pro Glu Leu Leu Asp Ala Ala Thr Val Leu Glu Pro
            485                 490                 495

Thr Thr Ala Phe Ile Arg Glu Ala Val Arg Glu Ile Asn Gln Leu Ser
        500                 505                 510

Asp Asp Tyr Ala Asp Asn Gln Glu Leu Gln Ala Val Leu Ala Asn Ala
        515                 520                 525

Gly Val Glu Ala Leu Ala Ala Asp Thr Val Asp Gln Ala Lys Ala Ala
    530                 535                 540

Leu Asp Lys Ala Lys Ala Ala Val Ala Gly Val Gln Leu Asp Glu Ala
545                 550                 555                 560

Arg Arg Glu Ala Tyr Arg Thr Ile Asn Ala Leu Ser Asp Gln His Lys
                565                 570                 575

Ser Asp Gln Lys Val Gln Leu Ala Leu Val Ala Ala Ala Lys Val
            580                 585                 590

Ala Asp Ala Ala Ser Val Asp Gln Val Asn Ala Ile Asn Asp Ala
        595                 600                 605

His Thr Ala Ile Ala Asp Ile Thr Gly Ala Ala Leu Leu Glu Ala Lys
    610                 615                 620

Glu Ala Ala Ile Asn Glu Leu Lys Gln Tyr Gly Ile Ser Asp Tyr Tyr
625                 630                 635                 640

Val Thr Leu Ile Asn Lys Ala Lys
                645

<210> SEQ ID NO 25
<211> LENGTH: 996
<212> TYPE: DNA
<213> ORGANISM: Streptococcus equi

<400> SEQUENCE: 25
ctggaagttc tgttccaggg gcccctggga tccgacgatt accaaaggaa tgctacggaa      60
gcttatgcca agaagtacc acatcagatc acttctgtat ggaccaaagg tgttacacca     120
ctaacacccg agcagtttcg atataataac gaagatgtga tccatgcgcc atatcttgct     180
catcaaggct ggtacgatat caccaaggcc ttcgatggga aggataatct cttgtgtggc     240
gcagcaacgg caggtaatat gctgcattgg tggtttgatc aaaataaaac agagattgaa     300
gcctatttaa gtaaacaccc tgaaaagcaa aaatcatttt taacaaccaa agagctattt     360
gatttgaaag ctgctatcga taccaaggac agtcaaacca atagtcagct ttttaattat     420
tttagagata agcctttcc aaatctatca gcacgtcaac tcggggttat gcctgatctt     480
```

-continued

```
gttctagaca tgtttatcaa tggttactac ttaaatgtgt ttaaaacaca gtctactgat    540
gtcaatcgac cttatcagga caaggacaaa cgaggtggta ttttcgatgc tgttttcacc    600
agaggagatc agacaacgct cttgacagct cgtcatgatt taaaaaataa aggactaaat    660
gacatcagca ccattatcaa gcaagaactg actgaaggaa gagcccttgc tttatcacat    720
acctacgcca atgttagcat tagccatgtg attaacttgt ggggagctga ttttaatgct    780
gaaggaaacc ttgaggccat ctatgtcaca gactcagatg ctaatgcgtc tattggtatg    840
aaaaaatatt ttgtcggcat taatgctcat agacatgtcg ccatttctgc caagaaaata    900
gaaggagaaa acattggcgc tcaagtatta ggcttattta cgctttccag tggcaaggac    960
atatggcaga aactgagcta actcgagcgg ccgcat                              996
```

<210> SEQ ID NO 26
<211> LENGTH: 326
<212> TYPE: PRT
<213> ORGANISM: Streptococcus equi

<400> SEQUENCE: 26

```
Leu Glu Val Leu Phe Gln Gly Pro Leu Gly Ser Asp Asp Tyr Gln Arg
1               5                   10                  15

Asn Ala Thr Glu Ala Tyr Ala Lys Glu Val Pro His Gln Ile Thr Ser
            20                  25                  30

Val Trp Thr Lys Gly Val Thr Pro Leu Thr Pro Glu Gln Phe Arg Tyr
        35                  40                  45

Asn Asn Glu Asp Val Ile His Ala Pro Tyr Leu Ala His Gln Gly Trp
    50                  55                  60

Tyr Asp Ile Thr Lys Ala Phe Asp Gly Lys Asp Asn Leu Leu Cys Gly
65                  70                  75                  80

Ala Ala Thr Ala Gly Asn Met Leu His Trp Trp Phe Asp Gln Asn Lys
                85                  90                  95

Thr Glu Ile Glu Ala Tyr Leu Ser Lys His Pro Glu Lys Gln Lys Ile
            100                 105                 110

Ile Phe Asn Asn Gln Glu Leu Phe Asp Leu Lys Ala Ala Ile Asp Thr
        115                 120                 125

Lys Asp Ser Gln Thr Asn Ser Gln Leu Phe Asn Tyr Phe Arg Asp Lys
    130                 135                 140

Ala Phe Pro Asn Leu Ser Ala Arg Gln Leu Gly Val Met Pro Asp Leu
145                 150                 155                 160

Val Leu Asp Met Phe Ile Asn Gly Tyr Tyr Leu Asn Val Phe Lys Thr
                165                 170                 175

Gln Ser Thr Asp Val Asn Arg Pro Tyr Gln Asp Lys Asp Lys Arg Gly
            180                 185                 190

Gly Ile Phe Asp Ala Val Phe Thr Arg Gly Asp Gln Thr Thr Leu Leu
        195                 200                 205

Thr Ala Arg His Asp Leu Lys Asn Lys Gly Leu Asn Asp Ile Ser Thr
    210                 215                 220

Ile Ile Lys Gln Glu Leu Thr Glu Gly Arg Ala Leu Ala Leu Ser His
225                 230                 235                 240

Thr Tyr Ala Asn Val Ser Ile Ser His Val Ile Asn Leu Trp Gly Ala
                245                 250                 255

Asp Phe Asn Ala Glu Gly Asn Leu Glu Ala Ile Tyr Val Thr Asp Ser
            260                 265                 270

Asp Ala Asn Ala Ser Ile Gly Met Lys Lys Tyr Phe Val Gly Ile Asn
        275                 280                 285
```

Ala His Arg His Val Ala Ile Ser Ala Lys Lys Ile Glu Gly Glu Asn
            290                 295                 300

Ile Gly Ala Gln Val Leu Gly Leu Phe Thr Leu Ser Ser Gly Lys Asp
305                 310                 315                 320

Ile Trp Gln Lys Leu Ser
                325

<210> SEQ ID NO 27
<211> LENGTH: 1452
<212> TYPE: DNA
<213> ORGANISM: Artificial Sequence
<220> FEATURE:
<223> OTHER INFORMATION: Recombinant gene fusion fragment

<400> SEQUENCE: 27

```
ctggaagttc tgttccaggg gcccctggga tccactaatc ttagtgacaa catcacatca    60
ttgacggttg cttcttcatc actccgagat ggagagagaa cgacggtaaa ggttgcgttt   120
gatgacaaaa aacagaaaat caaggcaggg gatacgatag aggtcacctg cctacaagt   180
ggtaatgtct acattcaggg ctttaataaa accataccgc ttaatattag aggggtagat   240
gttggtacct tggaggtcac gctagacaag gctgttttca cattcaatca aaatattgaa   300
acaatgcatg atgtctctgg ttggggagag tttgatatta ctgttagaaa tgtgacacaa   360
accaccgctg aaacatcagg aacgaccaca gtaaaggtag gcaatcgcac tgctactatc   420
actgttacta agcctgaggc aggcactggt accagctcat tttattataa gactggtgat   480
atgcagccca tgatactga gcgtgtgaga tggttcctgc tgattaacaa caacaaggaa    540
tgggtggcca atactgttac agtcgaagac gatattcaag gtggtcaaac cttggatatg   600
agcagctttg acatcaccgt atctggttat cgtaacgagc gcttcgttgg ggaaaacgct   660
ctgacagagt ttcatacaac atttccaaat tctgtcatta cggcaacaga taatcacatt   720
agtgtgcggt tagatcaata tgatgcctca caaaacactg tcaacattgc ttataagaca   780
aagataacgg actttgacca aaaagaattt gccaacaaca gtaaaatctg gtaccagatt   840
ttatacaagg atcaggtatc gggtcaagag tcaaaccacc aagtagccaa atcaatgct   900
aacggcgggg ttgatggcag tcgctatacc agctttactg tcaaggagct cttagacgca   960
gcaacagtgt tagagcctac aacagccttc attagagaag ctgttaggga aatcaatcag  1020
ctgagtgatg actacgctga caatcaagag cttcaggctg ttcttgctaa tgctggagtt  1080
gaggcacttg ctgcagatac tgttgatcag gctaaagcag ctcttgacaa agcaaaggca  1140
gctgttgctg gtgttcagct tgatgaagca agacgtgagg cttacagaac aatcaatgcc  1200
ttaagtgatc agcacaaaag cgatcaaaag gttcagctag ctctagttgc tgcagcagct  1260
aaggtggcag atgctgcttc agttgatcaa gtgaatgcag ccattaatga tgctcataca  1320
gctattgcgg acattacagg agcagccttg ttggaggcta agaagctgc tatcaatgaa  1380
ctaaagcagt atggcattag tgattactat gtgaccttaa tcaacaaagc caaataactc  1440
gagcggccgc at                                                      1452
```

<210> SEQ ID NO 28
<211> LENGTH: 478
<212> TYPE: PRT
<213> ORGANISM: Artificial Sequence
<220> FEATURE:
<223> OTHER INFORMATION: Recombinant fusion protein

<400> SEQUENCE: 28

```
Leu Glu Val Leu Phe Gln Gly Pro Leu Gly Ser Thr Asn Leu Ser Asp
1               5                   10                  15

Asn Ile Thr Ser Leu Thr Val Ala Ser Ser Leu Arg Asp Gly Glu
            20                  25                  30

Arg Thr Thr Val Lys Val Ala Phe Asp Asp Lys Lys Gln Lys Ile Lys
        35                  40                  45

Ala Gly Asp Thr Ile Glu Val Thr Trp Pro Thr Ser Gly Asn Val Tyr
50                  55                  60

Ile Gln Gly Phe Asn Lys Thr Ile Pro Leu Asn Ile Arg Gly Val Asp
65                  70                  75                  80

Val Gly Thr Leu Glu Val Thr Leu Asp Lys Ala Val Phe Thr Phe Asn
                85                  90                  95

Gln Asn Ile Glu Thr Met His Asp Val Ser Gly Trp Gly Glu Phe Asp
                100                 105                 110

Ile Thr Val Arg Asn Val Thr Gln Thr Thr Ala Glu Thr Ser Gly Thr
            115                 120                 125

Thr Thr Val Lys Val Gly Asn Arg Thr Ala Thr Ile Thr Val Thr Lys
        130                 135                 140

Pro Glu Ala Gly Thr Gly Thr Ser Ser Phe Tyr Tyr Lys Thr Gly Asp
145                 150                 155                 160

Met Gln Pro Asn Asp Thr Glu Arg Val Arg Trp Phe Leu Leu Ile Asn
                165                 170                 175

Asn Asn Lys Glu Trp Val Ala Asn Thr Val Thr Val Glu Asp Asp Ile
                180                 185                 190

Gln Gly Gly Gln Thr Leu Asp Met Ser Ser Phe Asp Ile Thr Val Ser
            195                 200                 205

Gly Tyr Arg Asn Glu Arg Phe Val Gly Glu Asn Ala Leu Thr Glu Phe
        210                 215                 220

His Thr Thr Phe Pro Asn Ser Val Ile Thr Ala Thr Asp Asn His Ile
225                 230                 235                 240

Ser Val Arg Leu Asp Gln Tyr Asp Ala Ser Gln Asn Thr Val Asn Ile
                245                 250                 255

Ala Tyr Lys Thr Lys Ile Thr Asp Phe Asp Gln Lys Glu Phe Ala Asn
                260                 265                 270

Asn Ser Lys Ile Trp Tyr Gln Ile Leu Tyr Lys Asp Gln Val Ser Gly
            275                 280                 285

Gln Glu Ser Asn His Gln Val Ala Asn Ile Asn Ala Asn Gly Gly Val
        290                 295                 300

Asp Gly Ser Arg Tyr Thr Ser Phe Thr Val Lys Glu Leu Leu Asp Ala
305                 310                 315                 320

Ala Thr Val Leu Glu Pro Thr Thr Ala Phe Ile Arg Glu Ala Val Arg
                325                 330                 335

Glu Ile Asn Gln Leu Ser Asp Asp Tyr Ala Asp Asn Gln Glu Leu Gln
                340                 345                 350

Ala Val Leu Ala Asn Ala Gly Val Glu Ala Leu Ala Ala Asp Thr Val
            355                 360                 365

Asp Gln Ala Lys Ala Ala Leu Asp Lys Ala Lys Ala Ala Val Ala Gly
        370                 375                 380

Val Gln Leu Asp Glu Ala Arg Arg Glu Ala Tyr Arg Thr Ile Asn Ala
385                 390                 395                 400

Leu Ser Asp Gln His Lys Ser Asp Gln Lys Val Gln Leu Ala Leu Val
                405                 410                 415
```

Ala Ala Ala Ala Lys Val Asp Ala Ala Ser Val Asp Gln Val Asn
            420                 425                 430

Ala Ala Ile Asn Asp Ala His Thr Ala Ile Ala Asp Ile Thr Gly Ala
                435                 440                 445

Ala Leu Leu Glu Ala Lys Glu Ala Ala Ile Asn Glu Leu Lys Gln Tyr
    450                 455                 460

Gly Ile Ser Asp Tyr Tyr Val Thr Leu Ile Asn Lys Ala Lys
465                 470                 475

<210> SEQ ID NO 29
<211> LENGTH: 2322
<212> TYPE: DNA
<213> ORGANISM: Artificial Sequence
<220> FEATURE:
<223> OTHER INFORMATION: Recombinant gene fusion fragment

<400> SEQUENCE: 29

| | | | | | |
|---|---|---|---|---|---|
| ctggaagttc | tgttccaggg | gccccthggga | tccgacgatt | accaaaggaa | tgctacggaa | 60 |
| gcttatgcca | agaagtacc | acatcagatc | acttctgtat | ggaccaaagg | tgttacacca | 120 |
| ctaacacccg | agcagtttcg | atataataac | gaagatgtga | tccatgcgcc | atatcttgct | 180 |
| catcaaggct | ggtacgatat | caccaaggcc | ttcgatggga | aggataatct | cttgtgtggc | 240 |
| gcagcaacgg | caggtaatat | gctgcattgg | tggtttgatc | aaaataaaac | agagattgaa | 300 |
| gcctatttaa | gtaaacaccc | tgaaaagcaa | aaaatcattt | ttaacaacca | agagctattt | 360 |
| gatttgaaag | ctgctatcga | taccaaggac | agtcaaacca | atagtcagct | ttttaattat | 420 |
| tttagagata | aagcctttcc | aaatctatca | gcacgtcaac | tcggggttat | gcctgatctt | 480 |
| gttctagaca | tgtttatcaa | tggttactac | ttaaatgtgt | ttaaaacaca | gtctactgat | 540 |
| gtcaatcgac | cttatcagga | caaggacaaa | cgaggtggta | ttttcgatgc | tgttttcacc | 600 |
| agaggagatc | agacaacgct | cttgacagct | cgtcatgatt | taaaaaataa | aggactaaat | 660 |
| gacatcagca | ccattatcaa | gcaagaactg | actgaaggaa | gagcccttgc | tttatcacat | 720 |
| acctacgcca | atgttagcat | tagccatgtg | attaacttgt | ggggagctga | ttttaatgct | 780 |
| gaaggaaacc | ttgaggccat | ctatgtcaca | gactcagatg | ctaatgcgtc | tattggtatg | 840 |
| aaaaaatatt | ttgtcggcat | taatgctcat | agacatgtcg | ccatttctgc | caagaaaata | 900 |
| gaaggagaaa | acattggcgc | tcaagtatta | ggcttattta | cgctttccag | tgcaaggac | 960 |
| atatggcaga | aactgagccc | atgggaaacg | actactgcta | gtgcatttga | aaataatggg | 1020 |
| acaggtcaac | atctgaactg | gcacatagat | attccacaag | aatatacagt | tgaattagga | 1080 |
| gaaccaatta | ctatctcaga | tcttatgagt | caaattacgg | ttactcgtaa | aggtagtaat | 1140 |
| gggactgtta | atgatggaga | tactttttgac | tttatttcga | atggagatgg | ttcaagagga | 1200 |
| attgataccc | ctggagtaaa | aatatggttt | gacttttaca | atgctgcggg | tacttccttt | 1260 |
| ttaactgatg | aaatgttagc | ttcgcctaca | tatgctgtac | cggggggatc | ttatactatt | 1320 |
| aaagcttggg | tattctatgg | gaaaaatgat | accaaaaagc | tcttcacatt | taaactaaaa | 1380 |
| aattccaaca | gcaataaaac | tgagttaagg | aagtcgttag | aggaggctaa | gctaaaactc | 1440 |
| agccagcctg | aaggaacgta | ttctgatgaa | tcactgcaag | ccttgcaatc | agcggttact | 1500 |
| attggtaaga | cctatttaaa | cagtgaccct | gatcaaaata | cagtagatca | atctgttact | 1560 |
| actattgatt | ccgctattac | tagtcttgtt | aatcttaatg | ctttaaatga | agctattaat | 1620 |
| caagctacac | tttttataac | agatggcaaa | gagtatccta | agaagcgta | tgacggtctt | 1680 |
| gtgcaaaagc | ttgcagcggc | agctaagctt | caaaattcat | ttggtccttc | acaaggagat | 1740 |

-continued

```
gttgataagg ctgcgactga tttaacgcaa gctcttacga cgcttaagac tgctgtagcg    1800
catgaagcct tagatcaagc cttggctaag ctgttagagc tttaccgaga aaatccaaat    1860
cttgctttga catcagagtc tttgaaggaa ttgtacaata aggccattga agcagcaggt    1920
accttctata gaactgttaa caaggataaa gagagaaaag acatttccct ttatgagcta    1980
gagcgctaca ctacagaaac aaattcagtt gttgatacta ttttaaaggt aaaggctgcg    2040
attgccgaag aaggaaaggc aaaattgcgt tctgctttag accaattaaa tgctcttatc    2100
ggagaaaatc tagacctatc tccatataca gcagcttctg ctcaagccta tacagaccag    2160
ctagctaagg ctaaggaggt cgcagcagcg ggtgagacag cttatgctca ggagacagaa    2220
ccgacagcta ttactaacag cttggttaag gtgttaaatg ctaagaaatc cctctcagat    2280
gccaaggcag ccttggttgc taaataactc gagcggccgc at                       2322
```

<210> SEQ ID NO 30
<211> LENGTH: 768
<212> TYPE: PRT
<213> ORGANISM: Artificial Sequence
<220> FEATURE:
<223> OTHER INFORMATION: Recombinant fusion protein

<400> SEQUENCE: 30

```
Leu Glu Val Leu Phe Gln Gly Pro Leu Gly Ser Asp Asp Tyr Gln Arg
1               5                   10                  15

Asn Ala Thr Glu Ala Tyr Ala Lys Glu Val Pro His Gln Ile Thr Ser
            20                  25                  30

Val Trp Thr Lys Gly Val Thr Pro Leu Thr Pro Glu Gln Phe Arg Tyr
        35                  40                  45

Asn Asn Glu Asp Val Ile His Ala Pro Tyr Leu Ala His Gln Gly Trp
    50                  55                  60

Tyr Asp Ile Thr Lys Ala Phe Asp Gly Lys Asp Asn Leu Leu Cys Gly
65                  70                  75                  80

Ala Ala Thr Ala Gly Asn Met Leu His Trp Trp Phe Asp Gln Asn Lys
                85                  90                  95

Thr Glu Ile Glu Ala Tyr Leu Ser Lys His Pro Glu Lys Gln Lys Ile
            100                 105                 110

Ile Phe Asn Asn Gln Glu Leu Phe Asp Leu Lys Ala Ala Ile Asp Thr
        115                 120                 125

Lys Asp Ser Gln Thr Asn Ser Gln Leu Phe Asn Tyr Phe Arg Asp Lys
    130                 135                 140

Ala Phe Pro Asn Leu Ser Ala Arg Gln Leu Gly Val Met Pro Asp Leu
145                 150                 155                 160

Val Leu Asp Met Phe Ile Asn Gly Tyr Tyr Leu Asn Val Phe Lys Thr
                165                 170                 175

Gln Ser Thr Asp Val Asn Arg Pro Tyr Gln Asp Lys Asp Lys Arg Gly
            180                 185                 190

Gly Ile Phe Asp Ala Val Phe Thr Arg Gly Asp Gln Thr Thr Leu Leu
        195                 200                 205

Thr Ala Arg His Asp Leu Lys Asn Lys Gly Leu Asn Asp Ile Ser Thr
    210                 215                 220

Ile Ile Lys Gln Glu Leu Thr Glu Gly Arg Ala Leu Ala Leu Ser His
225                 230                 235                 240

Thr Tyr Ala Asn Val Ser Ile Ser His Val Ile Asn Leu Trp Gly Ala
                245                 250                 255
```

```
Asp Phe Asn Ala Glu Gly Asn Leu Glu Ala Ile Tyr Val Thr Asp Ser
            260                 265                 270

Asp Ala Asn Ala Ser Ile Gly Met Lys Lys Tyr Phe Val Gly Ile Asn
        275                 280                 285

Ala His Arg His Val Ala Ile Ser Ala Lys Lys Ile Glu Gly Glu Asn
    290                 295                 300

Ile Gly Ala Gln Val Leu Gly Leu Phe Thr Leu Ser Ser Gly Lys Asp
305                 310                 315                 320

Ile Trp Gln Lys Leu Ser Pro Trp Glu Thr Thr Thr Ala Ser Ala Phe
                325                 330                 335

Glu Asn Asn Gly Thr Gly Gln His Leu Asn Trp His Ile Asp Ile Pro
            340                 345                 350

Gln Glu Tyr Thr Val Glu Leu Gly Glu Pro Ile Thr Ile Ser Asp Leu
        355                 360                 365

Met Ser Gln Ile Thr Val Thr Arg Lys Gly Ser Asn Gly Thr Val Asn
    370                 375                 380

Asp Gly Asp Thr Phe Asp Phe Ile Ser Asn Gly Asp Gly Ser Arg Gly
385                 390                 395                 400

Ile Asp Thr Pro Gly Val Lys Ile Trp Phe Asp Phe Tyr Asn Ala Ala
                405                 410                 415

Gly Thr Ser Phe Leu Thr Asp Glu Met Leu Ala Ser Pro Thr Tyr Ala
            420                 425                 430

Val Pro Gly Ser Tyr Thr Ile Lys Ala Trp Val Phe Tyr Gly Lys
        435                 440                 445

Asn Asp Thr Lys Lys Leu Phe Thr Phe Lys Leu Lys Asn Ser Asn Ser
450                 455                 460

Asn Lys Thr Glu Leu Arg Lys Ser Leu Glu Glu Ala Lys Leu Lys Leu
465                 470                 475                 480

Ser Gln Pro Glu Gly Thr Tyr Ser Asp Glu Ser Leu Gln Ala Leu Gln
                485                 490                 495

Ser Ala Val Thr Ile Gly Lys Thr Tyr Leu Asn Ser Asp Pro Asp Gln
            500                 505                 510

Asn Thr Val Asp Gln Ser Val Thr Thr Ile Asp Ser Ala Ile Thr Ser
        515                 520                 525

Leu Val Asn Leu Asn Ala Leu Asn Glu Ala Ile Asn Gln Ala Thr Pro
    530                 535                 540

Phe Ile Thr Asp Gly Lys Glu Tyr Pro Lys Glu Ala Tyr Asp Gly Leu
545                 550                 555                 560

Val Gln Lys Leu Ala Ala Ala Lys Leu Gln Asn Ser Phe Gly Pro
                565                 570                 575

Ser Gln Gly Asp Val Asp Lys Ala Ala Thr Asp Leu Thr Gln Ala Leu
            580                 585                 590

Thr Thr Leu Lys Thr Ala Val Ala His Glu Ala Leu Asp Gln Ala Leu
        595                 600                 605

Ala Lys Leu Leu Glu Leu Tyr Arg Glu Asn Pro Asn Leu Ala Leu Thr
    610                 615                 620

Ser Glu Ser Leu Lys Glu Leu Tyr Asn Lys Ala Ile Glu Ala Ala Gly
625                 630                 635                 640

Thr Phe Tyr Arg Thr Val Asn Lys Asp Lys Glu Arg Lys Asp Ile Ser
                645                 650                 655

Leu Tyr Glu Leu Glu Arg Tyr Thr Thr Glu Thr Asn Ser Val Val Asp
            660                 665                 670

Thr Ile Leu Lys Val Lys Ala Ala Ile Ala Glu Glu Gly Lys Ala Lys
```

| | | 675 | | | 680 | | | 685 | | | |
|---|---|---|---|---|---|---|---|---|---|---|---|
| Leu | Arg | Ser | Ala | Leu | Asp | Gln | Leu | Asn | Ala | Leu | Ile | Gly | Glu | Asn | Leu |
| | | 690 | | | | 695 | | | | 700 | |

| Asp | Leu | Ser | Pro | Tyr | Thr | Ala | Ala | Ser | Ala | Gln | Ala | Tyr | Thr | Asp | Gln |
|---|---|---|---|---|---|---|---|---|---|---|---|---|---|---|---|
| 705 | | | | 710 | | | | 715 | | | | 720 |

| Leu | Ala | Lys | Ala | Lys | Glu | Val | Ala | Ala | Ala | Gly | Glu | Thr | Ala | Tyr | Ala |
|---|---|---|---|---|---|---|---|---|---|---|---|---|---|---|---|
| | | | 725 | | | | 730 | | | | 735 |

| Gln | Glu | Thr | Glu | Pro | Thr | Ala | Ile | Thr | Asn | Ser | Leu | Val | Lys | Val | Leu |
|---|---|---|---|---|---|---|---|---|---|---|---|---|---|---|---|
| | | | 740 | | | | 745 | | | | 750 |

| Asn | Ala | Lys | Lys | Ser | Leu | Ser | Asp | Ala | Lys | Ala | Ala | Leu | Val | Ala | Lys |
|---|---|---|---|---|---|---|---|---|---|---|---|---|---|---|---|
| | | 755 | | | | 760 | | | | 765 |

<210> SEQ ID NO 31
<211> LENGTH: 3004
<212> TYPE: DNA
<213> ORGANISM: Streptococcus equi

<400> SEQUENCE: 31

```
ctggaagttc tgttccaggg gcccctggga tccgaggata aggttgtgca aactagtcca      60
tcagtctctg ctattgatga cctacattac ctgtcggaaa acagtaaaaa agaatttaag     120
gagggttat caaaggcagg agaagtacct gaaaagctaa aggatatttt atccaaggca     180
cagcaggcag ataagcaggc aaaggttctt gcagaaatga aggttcctga aaaatagcc      240
atgaagcctt taaggggcc tctttatggt ggctatttta ggacttggca tgataaaaca      300
tcagatccgg ctgaaaagga taaggttaat tctatgggag aattgcctaa ggaggttgac     360
ttagcctttg ttttccatga ttggaccaag gattatagct ttttctggca agaattggcg     420
accaagcatg tgccaacgct gaacaagcag ggaacacgtg tgattcgtac cattccatgg     480
cggttccttg caggcggtga tcatagtggt attgctgaag atacgcaaaa atacccaaat     540
actccagagg gaaataaggc cttggcaaag gctattgtag atgaatacgt ttataaatat     600
aatcttgatg gtttagatgt tgatattgag cgggatagca ttccaaaagt aaatggaaaa     660
gagagtaacg aaaatattca gcgctctatt gctgtttttg aagaaattgg caagcttatt     720
gggccaaagg gcgctgacaa gtcacgtttg ttcattatgg atagcaccta catggctgac     780
aagaacccat tgattgagcg cggtgcccaa tatattgatt tgctgcttgt gcaggtttat     840
ggcactcaag gtgagaaggg agattgggat ccagtcgcta gaaaacctga aaagacaatg     900
gaggaacgtt gggaatcgta tagcaaatac attcgtcctg agcagtacat ggttggtttt     960
tctttctatg aggaatatgc gggcagtggt aacctctggt atgatattaa tgagaggaaa    1020
gatgatcata tccgttaaa ttcagagata gctggtactc gtgctgagcg ttatgcaaaa    1080
tggcagccta agacaggtgg tgtcaaggga gggattttct cttatgcgat tgatcgcgat    1140
ggtgtagcgc atcaacctaa aaaagtctca gatgatgaga aagaactaa caaggctata    1200
aaggatataa cagatggtat tgtcaaatca gattataagg tttctaaggc cttgaagaag    1260
gttatggaaa atgacaaatc ctatgagctg attgatcaga agattttcc agacaaggct    1320
ttgcgagaag cagttattgc acaggttgga agcagaagag gggatttaga gcggttcaat    1380
ggaaccctgc gcttagacaa tccggatatc aagagtttag aaggcctgaa taagcttaaa    1440
aaactagcta agctagagct aatcggtcta tcacaaatca caaagctgga tagcttagtc    1500
ctacctgcaa atgctaagcc gaccaaggat acgctggcca atgttcttga agcctacgac    1560
agcgctaaga aggaagagac taaggcgatt ccacaggtgg ctctgaccat ttctggtcta    1620
```

```
actggcttga aggaattaaa tcttgctggc tttgatcgtg atagcttggc tggaattgac    1680
gcagctagcc taacctctct tgaaaaggtg gatctctcta gtaataagct ggacttagca    1740
gctggtacgg aaaatcgtca gattcttgat accatgctgg caacagtgac taagcatggc    1800
ggtgttagcg aaaagacgtt tgtatttgat catcaaaagc ctactggtct ttatcctgat    1860
acttatggca ctaagagcct tcagttacca gtagcaaatg atacaattga tttgcaggct    1920
aagcttttat ttggaacagt taccaatcag ggcacgctaa tcaatagcga agctgactat    1980
aaggcttatc aggagcagga aatagcaggt caccgttttg ttgattcaag ctatgattac    2040
aaagcctttg cagtgaccta caaggactat aagatcaagg tgactgactc aaccttaggt    2100
gtcactgatc acaaggactt atccactagc aaggaggaga cctacaaggt tgaattcttt    2160
agccctacta atagcactaa gcctgtgcat gaggctaagg ttgtcgttgg tgcggaaaaa    2220
accatgatgg ttaacctagc agagggagca actgtgattg gtggtgatgc agatccaaca    2280
aatgcaaaaa aagtgtttga tggtttgctc aataatgata caacaattct gtcaactagc    2340
aataaagctt ctatcatttt tgaacttaaa gagcctggct tagtcaagta ttggcgtttc    2400
tttaatgaca gcaaaattag taaagctgac tgtattaagg aggccaagct tgaagccttt    2460
gttggccatc ttgaagctgg ctcaaaggta aggatagct tggaaaaatc atcaaaatgg    2520
gtaacagttt cagattattc aggagaggac caagagttta gccagccgtt aaacaacatt    2580
ggtgccaaat attggagaat aacagttgat actaagggag gacgttacaa ttggccatca    2640
cttcctgagc ttcaaatcat tggttatcaa ttaccggctg cggatcttgt gatggcaatg    2700
ctagctactg cagaggagct atctcagcaa aaagacaagt tctctcaaga gcagcttaag    2760
gagctcgaag tcaaaatagc tgccttaaag gctgctttag atagtaagat gtttaatgcc    2820
gatgctatta cgctagtac tgctgatctg aaggcttatg ttgataagct tttagctgat    2880
agaactgatc aggaaaaagt agctaaagca gctaaagttg agcagcctgt ggctactgac    2940
ataaaagaaa atactgagcc agaaaatcca aagacagact agcttatccc tcgagcggcc    3000
gcat                                                                3004
```

<210> SEQ ID NO 32
<211> LENGTH: 993
<212> TYPE: PRT
<213> ORGANISM: Streptococcus equi

<400> SEQUENCE: 32

Leu Glu Val Leu Phe Gln Gly Pro Leu Gly Ser Glu Asp Lys Val Val
1               5                   10                  15

Gln Thr Ser Pro Ser Val Ser Ala Ile Asp Asp Leu His Tyr Leu Ser
            20                  25                  30

Glu Asn Ser Lys Lys Glu Phe Lys Glu Gly Leu Ser Lys Ala Gly Glu
        35                  40                  45

Val Pro Glu Lys Leu Lys Asp Ile Leu Ser Lys Ala Gln Gln Ala Asp
    50                  55                  60

Lys Gln Ala Lys Val Leu Ala Glu Met Lys Val Pro Glu Lys Ile Ala
65                  70                  75                  80

Met Lys Pro Leu Lys Gly Pro Leu Tyr Gly Gly Tyr Phe Arg Thr Trp
                85                  90                  95

His Asp Lys Thr Ser Asp Pro Ala Glu Lys Asp Lys Val Asn Ser Met
            100                 105                 110

Gly Glu Leu Pro Lys Glu Val Asp Leu Ala Phe Val Phe His Asp Trp
        115                 120                 125

```
Thr Lys Asp Tyr Ser Phe Phe Trp Gln Glu Leu Ala Thr Lys His Val
130                 135                 140

Pro Thr Leu Asn Lys Gln Gly Thr Arg Val Ile Arg Thr Ile Pro Trp
145                 150                 155                 160

Arg Phe Leu Ala Gly Gly Asp His Ser Gly Ile Ala Glu Asp Thr Gln
                165                 170                 175

Lys Tyr Pro Asn Thr Pro Glu Gly Asn Lys Ala Leu Ala Lys Ala Ile
                180                 185                 190

Val Asp Glu Tyr Val Tyr Lys Tyr Asn Leu Asp Gly Leu Asp Val Asp
                195                 200                 205

Ile Glu Arg Asp Ser Ile Pro Lys Val Asn Gly Lys Glu Ser Asn Glu
210                 215                 220

Asn Ile Gln Arg Ser Ile Ala Val Phe Glu Glu Ile Gly Lys Leu Ile
225                 230                 235                 240

Gly Pro Lys Gly Ala Asp Lys Ser Arg Leu Phe Ile Met Asp Ser Thr
                245                 250                 255

Tyr Met Ala Asp Lys Asn Pro Leu Ile Glu Arg Gly Ala Gln Tyr Ile
                260                 265                 270

Asp Leu Leu Leu Val Gln Val Tyr Gly Thr Gln Gly Glu Lys Gly Asp
                275                 280                 285

Trp Asp Pro Val Ala Arg Lys Pro Glu Lys Thr Met Glu Glu Arg Trp
290                 295                 300

Glu Ser Tyr Ser Lys Tyr Ile Arg Pro Glu Gln Tyr Met Val Gly Phe
305                 310                 315                 320

Ser Phe Tyr Glu Glu Tyr Ala Gly Ser Gly Asn Leu Trp Tyr Asp Ile
                325                 330                 335

Asn Glu Arg Lys Asp Asp His Asn Pro Leu Asn Ser Glu Ile Ala Gly
                340                 345                 350

Thr Arg Ala Glu Arg Tyr Ala Lys Trp Gln Pro Lys Thr Gly Gly Val
                355                 360                 365

Lys Gly Gly Ile Phe Ser Tyr Ala Ile Asp Arg Asp Gly Val Ala His
                370                 375                 380

Gln Pro Lys Lys Val Ser Asp Glu Lys Arg Thr Asn Lys Ala Ile
385                 390                 395                 400

Lys Asp Ile Thr Asp Gly Ile Val Lys Ser Asp Tyr Lys Val Ser Lys
                405                 410                 415

Ala Leu Lys Lys Val Met Glu Asn Asp Lys Ser Tyr Glu Leu Ile Asp
                420                 425                 430

Gln Lys Asp Phe Pro Asp Lys Ala Leu Arg Glu Ala Val Ile Ala Gln
                435                 440                 445

Val Gly Ser Arg Arg Gly Asp Leu Glu Arg Phe Asn Gly Thr Leu Arg
450                 455                 460

Leu Asp Asn Pro Asp Ile Lys Ser Leu Glu Gly Leu Asn Lys Leu Lys
465                 470                 475                 480

Lys Leu Ala Lys Leu Glu Leu Ile Gly Leu Ser Gln Ile Thr Lys Leu
                485                 490                 495

Asp Ser Leu Val Leu Pro Ala Asn Ala Lys Pro Thr Lys Asp Thr Leu
                500                 505                 510

Ala Asn Val Leu Glu Ala Tyr Asp Ser Ala Lys Lys Glu Glu Thr Lys
                515                 520                 525

Ala Ile Pro Gln Val Ala Leu Thr Ile Ser Gly Leu Thr Gly Leu Lys
                530                 535                 540
```

-continued

```
Glu Leu Asn Leu Ala Gly Phe Asp Arg Asp Ser Leu Ala Gly Ile Asp
545                 550                 555                 560

Ala Ala Ser Leu Thr Ser Leu Glu Lys Val Asp Leu Ser Ser Asn Lys
                565                 570                 575

Leu Asp Leu Ala Ala Gly Thr Glu Asn Arg Gln Ile Leu Asp Thr Met
            580                 585                 590

Leu Ala Thr Val Thr Lys His Gly Gly Val Ser Glu Lys Thr Phe Val
        595                 600                 605

Phe Asp His Gln Lys Pro Thr Gly Leu Tyr Pro Asp Thr Tyr Gly Thr
    610                 615                 620

Lys Ser Leu Gln Leu Pro Val Ala Asn Asp Thr Ile Asp Leu Gln Ala
625                 630                 635                 640

Lys Leu Leu Phe Gly Thr Val Thr Asn Gln Gly Thr Leu Ile Asn Ser
                645                 650                 655

Glu Ala Asp Tyr Lys Ala Tyr Gln Glu Gln Glu Ile Ala Gly His Arg
            660                 665                 670

Phe Val Asp Ser Ser Tyr Asp Tyr Lys Ala Phe Ala Val Thr Tyr Lys
        675                 680                 685

Asp Tyr Lys Ile Lys Val Thr Asp Ser Thr Leu Gly Val Thr Asp His
    690                 695                 700

Lys Asp Leu Ser Thr Ser Lys Glu Glu Thr Tyr Lys Val Glu Phe Phe
705                 710                 715                 720

Ser Pro Thr Asn Ser Thr Lys Pro Val His Glu Ala Lys Val Val Val
                725                 730                 735

Gly Ala Glu Lys Thr Met Met Val Asn Leu Ala Glu Gly Ala Thr Val
            740                 745                 750

Ile Gly Gly Asp Ala Asp Pro Thr Asn Ala Lys Lys Val Phe Asp Gly
        755                 760                 765

Leu Leu Asn Asn Asp Thr Thr Ile Leu Ser Thr Ser Asn Lys Ala Ser
    770                 775                 780

Ile Ile Phe Glu Leu Lys Glu Pro Gly Leu Val Lys Tyr Trp Arg Phe
785                 790                 795                 800

Phe Asn Asp Ser Lys Ile Ser Lys Ala Asp Cys Ile Lys Glu Ala Lys
                805                 810                 815

Leu Glu Ala Phe Val Gly His Leu Glu Ala Gly Ser Lys Val Lys Asp
            820                 825                 830

Ser Leu Glu Lys Ser Ser Lys Trp Val Thr Val Ser Asp Tyr Ser Gly
        835                 840                 845

Glu Asp Gln Glu Phe Ser Gln Pro Leu Asn Asn Ile Gly Ala Lys Tyr
    850                 855                 860

Trp Arg Ile Thr Val Asp Thr Lys Gly Gly Arg Tyr Asn Trp Pro Ser
865                 870                 875                 880

Leu Pro Glu Leu Gln Ile Ile Gly Tyr Gln Leu Pro Ala Ala Asp Leu
                885                 890                 895

Val Met Ala Met Leu Ala Thr Ala Glu Glu Leu Ser Gln Gln Lys Asp
            900                 905                 910

Lys Phe Ser Gln Glu Gln Leu Lys Glu Leu Glu Val Lys Ile Ala Ala
        915                 920                 925

Leu Lys Ala Ala Leu Asp Ser Lys Met Phe Asn Ala Asp Ala Ile Asn
    930                 935                 940

Ala Ser Thr Ala Asp Leu Lys Ala Tyr Val Asp Lys Leu Leu Ala Asp
945                 950                 955                 960

Arg Thr Asp Gln Glu Lys Val Ala Lys Ala Ala Lys Val Glu Gln Pro
```

```
                 965                 970                 975
Val Ala Thr Asp Ile Lys Glu Asn Thr Glu Pro Glu Asn Pro Lys Thr
            980                 985                 990

Asp

<210> SEQ ID NO 33
<211> LENGTH: 2715
<212> TYPE: DNA
<213> ORGANISM: Artificial Sequence
<220> FEATURE:
<223> OTHER INFORMATION: Recombinant gene fusion fragment

<400> SEQUENCE: 33
ctggaagttc tgttccaggg gcccctggga tccactaatc ttagtgacaa catcacatca      60
ttgacggttg cttcttcatc actccgagat ggagagagaa cgacggtaaa ggttgcgttt     120
gatgacaaaa aacagaaaat caaggcaggg gatacgatag aggtcacctg cctacaagt     180 ggtaatgtct acattcaggg ctttaataaa accataccgc ttaatattag aggggtagat     240
gttggtacct tggaggtcac gctagacaag gctgttttca cattcaatca aatattgaa     300 acaatgcatg atgtctctgg ttggggagag tttgatatta ctgttagaaa tgtgacacaa     360
accaccgctg aaacatcagg aacgaccaca gtaaaggtag gcaatcgcac tgctactatc     420
actgttacta agcctgaggc aggcactggt accagctcat tttattataa gactggtgat     480
atgcagccca tgatactga  gcgtgtgaga tggttcctgc tgattaacaa caacaaggaa     540
tgggtggcca atactgttac agtcgaagac gatattcaag gtggtcaaac cttggatatg     600
agcagctttg acatcaccgt atctggttat cgtaacgagc gcttcgttgg ggaaaacgct     660
ctgacagagt ttcatacaac atttccaaat tctgtcatta cggcaacaga taatcacatt     720
agtgtgcggt tagatcaata tgatgcctca caaaacactg tcaacattgc ttataagaca     780
aagataacgg actttgacca aaaagaattt gccaacaaca gtaaaatctg gtaccagatt     840
ttatacaagg atcaggtatc gggtcaagag tcaaccacc aagtagccaa tatcaatgct     900
aacggcgggg ttgatggcag tcgctatacc agctttactg tcaaggagct cgatacagca     960
agctatacca tcactgttga gggagctaca gcaggtcaca cctatgaggc ttatcagatt    1020
ttcaagggtg acttgtttga cagtaccta tcaaacatca catggggagg tggtgttaca    1080
ccttttgaat ttgatggttc aaaagacgct gctaagattg cagagggatt gaaggaagca    1140
aatgcagctg cctttgccaa ggaagcaggt aagcacttga cagcaaccat tgcaggaaca    1200
ggaacacatg caatcaccgt taacgaggct ggctactacc tcatcaagga caaaaatgat    1260
tctcaaacag gcaagcatga cgcctacacc tcatttgtcc tgaaggttgt taaaaacacc    1320
agcttcaaac caaatctgc tatcccaaca gtccttaaaa aggtcaagga ccgtaatgac    1380
aagacaggtc ttgagacagg ctggcaagat tcagctgact atgacaaaaa tgacaaggtg    1440
ccattccagc taaccgcaac cctaccgtca aattacgatg cctttcaaga atactacctt    1500
gaatttgtag ataccttatc aaaagggcta agctacaaca aagacgccaa ggtctatgtg    1560
gttaatggag atactcgtca agatattact aattcattta cagttagtga agatggttca    1620
tcttttaaaa tcaataacct aaaggctgtt cagggagtaa caataacagc taccagtaag    1680
atcgttgtcg aatacactgc taccctcaat gaccaagcgg ccatcggcaa aaaggaaat    1740 ccaaacgaag ttgctttgaa atactcaaac gatccaaacg ctcttggaaa aggagaggag    1800
tctccaaaag gggagacacc aaaagacaag gttatcgttt tcacctataa aacttctaga    1860
```

| | |
|---|---:|
| ttatctggtc cgccaggata cccacttact cgtgatttct cccgtaactt cctagaagaa | 1920 |
| aatactgcaa aatatttaga tcaattaaga gaacatctac agcacagatt tagtgaactt | 1980 |
| gagagcttaa caagaaaatt agagaaagaa ggcggtaccc gaggtccact gcaggaccag | 2040 |
| ccagcagcac taaatatcc agaacctaga gactattttc ttcatactcg tgaaggtgat | 2100 |
| gttatttatg atgaggatat aaaaagatat tttgaggatt tagaagccta tttaacagct | 2160 |
| agacttggtg ggattgataa aaagtagaaa gaagctgccc aaaagccaga gctcttagac | 2220 |
| gcagcaacag tgttagagcc tacaacagcc ttcattagag aagctgttag ggaaatcaat | 2280 |
| cagctgagtg atgactacgc tgacaatcaa gagcttcagg ctgttcttgc taatgctgga | 2340 |
| gttgaggcac ttgctgcaga tactgttgat caggctaaag cagctcttga caaagcaaag | 2400 |
| gcagctgttg ctggtgttca gcttgatgaa gcaagacgtg aggcttacag aacaatcaat | 2460 |
| gccttaagtg atcagcacaa aagcgatcaa aaggttcagc tagctctagt tgctgcagca | 2520 |
| gctaaggtgg cagatgctgc ttcagttgat caagtgaatg cagccattaa tgatgctcat | 2580 |
| acagctattg cggacattac aggagcagcc ttgttggagg ctaaagaagc tgctatcaat | 2640 |
| gaactaaagc agtatggcat tagtgattac tatgtgacct aatcaacaa agccaaataa | 2700 |
| ctcgagcggc cgcat | 2715 |

<210> SEQ ID NO 34
<211> LENGTH: 899
<212> TYPE: PRT
<213> ORGANISM: Artificial Sequence
<220> FEATURE:
<223> OTHER INFORMATION: Recombinant fusion protein

<400> SEQUENCE: 34

Leu Glu Val Leu Phe Gln Gly Pro Leu Gly Ser Thr Asn Leu Ser Asp
1               5                   10                  15

Asn Ile Thr Ser Leu Thr Val Ala Ser Ser Ser Leu Arg Asp Gly Glu
            20                  25                  30

Arg Thr Thr Val Lys Val Ala Phe Asp Asp Lys Lys Gln Lys Ile Lys
        35                  40                  45

Ala Gly Asp Thr Ile Glu Val Thr Trp Pro Thr Ser Gly Asn Val Tyr
    50                  55                  60

Ile Gln Gly Phe Asn Lys Thr Ile Pro Leu Asn Ile Arg Gly Val Asp
65                  70                  75                  80

Val Gly Thr Leu Glu Val Thr Leu Asp Lys Ala Val Phe Thr Phe Asn
                85                  90                  95

Gln Asn Ile Glu Thr Met His Asp Val Ser Gly Trp Gly Glu Phe Asp
            100                 105                 110

Ile Thr Val Arg Asn Val Thr Gln Thr Thr Ala Glu Thr Ser Gly Thr
        115                 120                 125

Thr Thr Val Lys Val Gly Asn Arg Thr Ala Thr Ile Thr Val Thr Lys
    130                 135                 140

Pro Glu Ala Gly Thr Gly Thr Ser Ser Phe Tyr Tyr Lys Thr Gly Asp
145                 150                 155                 160

Met Gln Pro Asn Asp Thr Glu Arg Val Arg Trp Phe Leu Leu Ile Asn
                165                 170                 175

Asn Asn Lys Glu Trp Val Ala Asn Thr Val Thr Val Glu Asp Asp Ile
            180                 185                 190

Gln Gly Gly Gln Thr Leu Asp Met Ser Ser Phe Asp Ile Thr Val Ser
        195                 200                 205

-continued

```
Gly Tyr Arg Asn Glu Arg Phe Val Gly Glu Asn Ala Leu Thr Glu Phe
    210                 215                 220
His Thr Thr Phe Pro Asn Ser Val Ile Thr Ala Thr Asp Asn His Ile
225                 230                 235                 240
Ser Val Arg Leu Asp Gln Tyr Asp Ala Ser Gln Asn Thr Val Asn Ile
                245                 250                 255
Ala Tyr Lys Thr Lys Ile Thr Asp Phe Asp Gln Lys Glu Phe Ala Asn
            260                 265                 270
Asn Ser Lys Ile Trp Tyr Gln Ile Leu Tyr Lys Asp Gln Val Ser Gly
        275                 280                 285
Gln Glu Ser Asn His Gln Val Ala Asn Ile Asn Ala Asn Gly Gly Val
    290                 295                 300
Asp Gly Ser Arg Tyr Thr Ser Phe Thr Val Lys Glu Leu Asp Thr Ala
305                 310                 315                 320
Ser Tyr Thr Ile Thr Val Glu Gly Ala Thr Ala Gly His Thr Tyr Glu
                325                 330                 335
Ala Tyr Gln Ile Phe Lys Gly Asp Leu Phe Asp Ser Thr Leu Ser Asn
            340                 345                 350
Ile Thr Trp Gly Gly Gly Val Thr Pro Phe Glu Phe Asp Gly Ser Lys
        355                 360                 365
Asp Ala Ala Lys Ile Ala Glu Gly Leu Lys Glu Ala Asn Ala Ala Ala
    370                 375                 380
Phe Ala Lys Glu Ala Gly Lys His Leu Thr Ala Ile Ala Gly Thr
385                 390                 395                 400
Gly Thr His Ala Ile Thr Val Asn Glu Ala Gly Tyr Tyr Leu Ile Lys
                405                 410                 415
Asp Lys Asn Asp Ser Gln Thr Gly Lys His Asp Ala Tyr Thr Ser Phe
            420                 425                 430
Val Leu Lys Val Val Lys Asn Thr Ser Phe Lys Pro Lys Ser Ala Ile
        435                 440                 445
Pro Thr Val Leu Lys Lys Val Lys Asp Arg Asn Asp Lys Thr Gly Leu
    450                 455                 460
Glu Thr Gly Trp Gln Asp Ser Ala Asp Tyr Asp Lys Asn Asp Lys Val
465                 470                 475                 480
Pro Phe Gln Leu Thr Ala Thr Leu Pro Ser Asn Tyr Asp Ala Phe Gln
                485                 490                 495
Glu Tyr Tyr Leu Glu Phe Val Asp Thr Leu Ser Lys Gly Leu Ser Tyr
            500                 505                 510
Asn Lys Asp Ala Lys Val Tyr Val Asn Gly Asp Thr Arg Gln Asp
        515                 520                 525
Ile Thr Asn Ser Phe Thr Val Ser Glu Asp Gly Ser Ser Phe Lys Ile
    530                 535                 540
Asn Asn Leu Lys Ala Val Gln Gly Val Thr Ile Thr Ala Thr Ser Lys
545                 550                 555                 560
Ile Val Val Glu Tyr Thr Ala Thr Leu Asn Asp Gln Ala Ala Ile Gly
                565                 570                 575
Lys Lys Gly Asn Pro Asn Glu Val Ala Leu Lys Tyr Ser Asn Asp Pro
            580                 585                 590
Asn Ala Leu Gly Lys Gly Glu Ser Pro Lys Gly Thr Pro Lys
        595                 600                 605
Asp Lys Val Ile Val Phe Thr Tyr Lys Thr Ser Arg Leu Ser Gly Pro
    610                 615                 620
Pro Gly Tyr Pro Leu Thr Arg Asp Phe Ser Arg Asn Phe Leu Glu Glu
```

```
                625                 630                 635                 640
        Asn Thr Ala Lys Tyr Leu Asp Gln Leu Arg Glu His Leu Gln His Arg
                        645                 650                 655

Phe Ser Glu Leu Glu Ser Leu Thr Arg Lys Leu Glu Lys Glu Gly Gly
                        660                 665                 670

Thr Arg Gly Pro Leu Gln Asp Gln Pro Ala Ala Leu Lys Tyr Pro Glu
                        675                 680                 685

Pro Arg Asp Tyr Phe Leu His Thr Arg Glu Gly Asp Val Ile Tyr Asp
                        690                 695                 700

Glu Asp Ile Lys Arg Tyr Phe Glu Asp Leu Glu Ala Tyr Leu Thr Ala
        705                 710                 715                 720

Arg Leu Gly Gly Ile Asp Lys Lys Val Glu Glu Ala Ala Gln Lys Pro
                        725                 730                 735

Glu Leu Leu Asp Ala Ala Thr Val Leu Glu Pro Thr Thr Ala Phe Ile
                        740                 745                 750

Arg Glu Ala Val Arg Glu Ile Asn Gln Leu Ser Asp Asp Tyr Ala Asp
                        755                 760                 765

Asn Gln Glu Leu Gln Ala Val Leu Ala Asn Ala Gly Val Glu Ala Leu
                        770                 775                 780

Ala Ala Asp Thr Val Asp Gln Ala Lys Ala Ala Leu Asp Lys Ala Lys
        785                 790                 795                 800

Ala Ala Val Ala Gly Val Gln Leu Asp Glu Ala Arg Arg Glu Ala Tyr
                        805                 810                 815

Arg Thr Ile Asn Ala Leu Ser Asp Gln His Lys Ser Asp Gln Lys Val
                        820                 825                 830

Gln Leu Ala Leu Val Ala Ala Ala Lys Val Ala Asp Ala Ala Ser
                        835                 840                 845

Val Asp Gln Val Asn Ala Ala Ile Asn Asp Ala His Thr Ala Ile Ala
                        850                 855                 860

Asp Ile Thr Gly Ala Ala Leu Leu Glu Ala Lys Glu Ala Ala Ile Asn
        865                 870                 875                 880

Glu Leu Lys Gln Tyr Gly Ile Ser Asp Tyr Tyr Val Thr Leu Ile Asn
                        885                 890                 895

Lys Ala Lys

<210> SEQ ID NO 35
<211> LENGTH: 28
<212> TYPE: DNA
<213> ORGANISM: Artificial Sequence
<220> FEATURE:
<223> OTHER INFORMATION: PCR primer

<400> SEQUENCE: 35
gcatccatgg atacagcaag ctatacca                                              28

<210> SEQ ID NO 36
<211> LENGTH: 31
<212> TYPE: DNA
<213> ORGANISM: Artificial Sequence
<220> FEATURE:
<223> OTHER INFORMATION: PCR primer

<400> SEQUENCE: 36
caattatttt ttcccagata ggagctcagc t                                          31

<210> SEQ ID NO 37
<211> LENGTH: 1283
```

```
<212> TYPE: DNA
<213> ORGANISM: Streptococcus equi

<400> SEQUENCE: 37
ccatggatac agcaagctat accatcactg ttgagggagc tacagcaggt cacacctatg      60
aggcttatca gattttcaag ggtgacttgt ttgacagtac cctatcaaac atcacatggg     120
gaggtggtgt tacaccttt gaatttgatg gttcaaaaga cgctgctaag attgcagagg     180
gattgaagga agcaaatgca gctgcctttg ccaaggaagc aggtaagcac ttgacagcaa     240
ccattgcagg aacaggaaca catgcaatca ccgttaacga ggctggctac tacctcatca     300
aggacaaaaa tgattctcaa acaggcaagc atgacgccta cacctcattt gtcctgaagg     360
ttgttaaaaa caccagcttc aaaccaaaat ctgctatccc aacagtcctt aaaaaggtca     420
aggaccgtaa tgacaagaca ggtcttgaga caggctggca agattcagct gactatgaca     480
aaaatgacaa ggtgccattc agctaaccg caaccctacc gtcaaattac gatgcctttc     540
aagaatacta ccttgaattt gtagatacct tatcaaaagg gctaagctac aacaaagacg     600
ccaaggtcta tgtggttaat ggagatactc gtcaagatat tactaattca tttacagtta     660
gtgaagatgg ttcatctttt aaaatcaata acctaaaggc tgttcaggga gtaacaataa     720
cagctaccag taagatcgtt gtcgaataca ctgctaccct caatgaccaa gcggccatcg     780
gcaaaaaagg aaatccaaac gaagttgctt tgaaatactc aaacgatcca aacgctcttg     840
gaaaaggaga ggagtctcca aaaggggaga caccaaaaga caaggttatc gttttcacct     900
ataaaactat catcaataag gttgatcaag atcaaaaagc cctaaaaggt gcaggcttta     960
ccctttataa gctggtcaaa ggtgataatg gcgaggaaaa atatcaaata gtccaagaaa    1020
ttaaagcagg ggatacaact agctttgagt ttgttggact tgacgctggt gattacaagc    1080
tcagcgaaac aacaacacct ggcggttaca acactattgc agatgtcatg ttcagcattg    1140
tagcgcagca tgaaaccgag tcagacgatc ctcagttgac tagcctaacc gttgacaaag    1200
caactggctt cactgctgat acagaagctg gtaccgtatc cgcaactatt gttaataaaa    1260
ggtctatcct cgagcccggg tgc                                            1283

<210> SEQ ID NO 38
<211> LENGTH: 426
<212> TYPE: PRT
<213> ORGANISM: Streptococcus equi

<400> SEQUENCE: 38

Met Asp Thr Ala Ser Tyr Thr Ile Thr Val Glu Gly Ala Thr Ala Gly
1               5                   10                  15

His Thr Tyr Glu Ala Tyr Gln Ile Phe Lys Gly Asp Leu Phe Asp Ser
            20                  25                  30

Thr Leu Ser Asn Ile Thr Trp Gly Gly Gly Val Thr Pro Phe Glu Phe
        35                  40                  45

Asp Gly Ser Lys Asp Ala Ala Lys Ile Ala Glu Gly Leu Lys Glu Ala
    50                  55                  60

Asn Ala Ala Ala Phe Ala Lys Glu Ala Gly Lys His Leu Thr Ala Thr
65                  70                  75                  80

Ile Ala Gly Thr Gly Thr His Ala Ile Thr Val Asn Glu Ala Gly Tyr
                85                  90                  95

Tyr Leu Ile Lys Asp Lys Asn Asp Ser Gln Thr Gly Lys His Asp Ala
            100                 105                 110

Tyr Thr Ser Phe Val Leu Lys Val Val Lys Asn Thr Ser Phe Lys Pro
```

```
              115                 120                 125
Lys Ser Ala Ile Pro Thr Val Leu Lys Val Lys Asp Arg Asn Asp
130                 135                 140

Lys Thr Gly Leu Glu Thr Gly Trp Gln Asp Ser Ala Asp Tyr Asp Lys
145                 150                 155                 160

Asn Asp Lys Val Pro Phe Gln Leu Thr Ala Thr Leu Pro Ser Asn Tyr
                165                 170                 175

Asp Ala Phe Gln Glu Tyr Tyr Leu Glu Phe Val Asp Thr Leu Ser Lys
            180                 185                 190

Gly Leu Ser Tyr Asn Lys Asp Ala Lys Val Tyr Val Asn Gly Asp
        195                 200                 205

Thr Arg Gln Asp Ile Thr Asn Ser Phe Thr Val Ser Glu Asp Gly Ser
210                 215                 220

Ser Phe Lys Ile Asn Asn Leu Lys Ala Val Gln Gly Val Thr Ile Thr
225                 230                 235                 240

Ala Thr Ser Lys Ile Val Val Glu Tyr Thr Ala Thr Leu Asn Asp Gln
                245                 250                 255

Ala Ala Ile Gly Lys Lys Gly Asn Pro Asn Glu Val Ala Leu Lys Tyr
            260                 265                 270

Ser Asn Asp Pro Asn Ala Leu Gly Lys Gly Glu Ser Pro Lys Gly
        275                 280                 285

Glu Thr Pro Lys Asp Lys Val Ile Val Phe Thr Tyr Lys Thr Ile Ile
290                 295                 300

Asn Lys Val Asp Gln Asp Gln Lys Ala Leu Lys Gly Ala Gly Phe Thr
305                 310                 315                 320

Leu Tyr Lys Leu Val Lys Gly Asp Asn Gly Glu Lys Tyr Gln Ile
                325                 330                 335

Val Gln Glu Ile Lys Ala Gly Asp Thr Thr Ser Phe Glu Phe Val Gly
            340                 345                 350

Leu Asp Ala Gly Asp Tyr Lys Leu Ser Glu Thr Thr Pro Gly Gly
        355                 360                 365

Tyr Asn Thr Ile Ala Asp Val Met Phe Ser Ile Val Ala Gln His Glu
370                 375                 380

Thr Glu Ser Asp Asp Pro Gln Leu Thr Ser Leu Thr Val Asp Lys Ala
385                 390                 395                 400

Thr Gly Phe Thr Ala Asp Thr Glu Ala Gly Thr Val Ser Ala Thr Ile
                405                 410                 415

Val Asn Lys Arg Ser Ile Leu Glu Pro Gly
            420                 425

<210> SEQ ID NO 39
<211> LENGTH: 29
<212> TYPE: DNA
<213> ORGANISM: Artificial Sequence
<220> FEATURE:
<223> OTHER INFORMATION: PCR primer

<400> SEQUENCE: 39
gcagccatgg agagtctgac gagtgttga                                29

<210> SEQ ID NO 40
<211> LENGTH: 31
<212> TYPE: DNA
<213> ORGANISM: Artificial Sequence
<220> FEATURE:
<223> OTHER INFORMATION: PCR primer
```

<400> SEQUENCE: 40

```
tcacctcgag tcctagctca ccgtcataag c                              31
```

<210> SEQ ID NO 41
<211> LENGTH: 1301
<212> TYPE: DNA
<213> ORGANISM: Streptococcus equi

<400> SEQUENCE: 41

```
ccatggagag tctgacgagt gttgagcctg ctgatggtgc ggtcatggtc aagtcagagg    60
ctgctgacca aggctcaaat gagctaccag aagctactga cattagtgat attgctggta   120
tttctgatgt gactaaggtg tcagctgctg tcaatgctga tactgtcaag gaagttcagc   180
cagtagctgt acctcttgta gaggatcagg cgcatgagga aactacagac cagtctcagc   240
cttcatcatc gatagtgtct gttacgacag acagctctct agagacacca gaagctacaa   300
gctcagagga gccgatagcg gagcagacct tgcggctgca tttcaagacc ctgccagctc   360
aagacctatc ctcgcttggt ctttgggtgt gggacgatgt tgacacacca tctgatcagc   420
tgggaggctg gccgactggg gctaccaatt ttagtctagc aagacagat gactatggct   480
attacatgga cgttaagctt tcagccaatc aagccaataa ggttagcttt ttgatcaata   540
acactaaggg agacaatctg acgggcgatc gaaccataga ccttctcagc cctaagatga   600
atgaggtctg gattgatggc caggagctgt cttactatcg ccgctggct cagggctata   660
tccgtatcaa ttattatcgc agtgatggcc attatgacaa caaatcgctc tggctttggg   720
gaagtgctga tgcgtcaatg actagtcagc agggcgcttg gccagatggt attgatttta   780
agcaggtcgg tcgatatggt gcttatatag atgtcaagct agctgatacc aatgagctag   840
gctttctctt gctagatgag cgtcagacag gtgacgctgt taaaattcag cccaatgatt   900
atattttaaa agatttaaag aatcacaccc aaattttctt gaaagacgag gatccaacca   960
tttatacgaa ccttatttt gttaatacag ttagattaat cggtgctcag caggtcagcc  1020
caagcagtat tgaggcgagc tttacgactc tagcagatgt ggataaggaa agcctttaa  1080
aagaattaaa aatcagcact gacagtaagg aagcagttgc tattactgat atcaccttag  1140
atgaaaagac tcataaggct gtcatcacag gtgattttag tcaagcagtg gccacttata  1200
cggtgacctt tcatcatgag agcttccagg ctaggccaaa ttggcaatac aaggatagcc  1260
tgtatgctta tgacggtgag ctaggactcg agcccgggtg c                      1301
```

<210> SEQ ID NO 42
<211> LENGTH: 432
<212> TYPE: PRT
<213> ORGANISM: Streptococcus equi

<400> SEQUENCE: 42

```
Met Glu Ser Leu Thr Ser Val Glu Pro Ala Asp Gly Ala Val Met Val
1               5                   10                  15

Lys Ser Glu Ala Ala Asp Gln Gly Ser Asn Glu Leu Pro Glu Ala Thr
            20                  25                  30

Asp Ile Ser Asp Ile Ala Gly Ile Ser Asp Val Thr Lys Val Ser Ala
        35                  40                  45

Ala Val Asn Ala Asp Thr Val Lys Glu Val Gln Pro Val Ala Val Pro
    50                  55                  60

Leu Val Glu Asp Gln Ala His Glu Glu Thr Thr Asp Gln Ser Gln Pro
65                  70                  75                  80
```

```
Ser Ser Ser Ile Val Ser Val Thr Thr Asp Ser Ser Leu Glu Thr Pro
            85              90              95
Glu Ala Thr Ser Ser Glu Glu Pro Ile Ala Glu Gln Thr Leu Arg Leu
            100             105             110
His Phe Lys Thr Leu Pro Ala Gln Asp Leu Ser Ser Leu Gly Leu Trp
            115             120             125
Val Trp Asp Asp Val Glu Thr Pro Ser Asp Gln Leu Gly Gly Trp Pro
130             135             140
Thr Gly Ala Thr Asn Phe Ser Leu Ala Lys Thr Asp Asp Tyr Gly Tyr
145             150             155             160
Tyr Met Asp Val Lys Leu Ser Ala Asn Gln Ala Asn Lys Val Ser Phe
            165             170             175
Leu Ile Asn Asn Thr Lys Gly Asp Asn Leu Thr Gly Asp Arg Thr Ile
            180             185             190
Asp Leu Leu Ser Pro Lys Met Asn Glu Val Trp Ile Asp Gly Gln Glu
            195             200             205
Leu Ser Tyr Tyr Arg Pro Leu Ala Gln Gly Tyr Ile Arg Ile Asn Tyr
            210             215             220
Tyr Arg Ser Asp Gly His Tyr Asp Asn Lys Ser Leu Trp Leu Trp Gly
225             230             235             240
Ser Ala Asp Ala Ser Met Thr Ser Gln Gln Gly Ala Trp Pro Asp Gly
            245             250             255
Ile Asp Phe Lys Gln Val Gly Arg Tyr Gly Ala Tyr Ile Asp Val Lys
            260             265             270
Leu Ala Asp Thr Asn Glu Leu Gly Phe Leu Leu Leu Asp Glu Arg Gln
            275             280             285
Thr Gly Asp Ala Val Lys Ile Gln Pro Asn Asp Tyr Ile Phe Lys Asp
            290             295             300
Leu Lys Asn His Thr Gln Ile Phe Leu Lys Asp Glu Asp Pro Thr Ile
305             310             315             320
Tyr Thr Asn Pro Tyr Phe Val Asn Thr Val Arg Leu Ile Gly Ala Gln
            325             330             335
Gln Val Ser Pro Ser Ser Ile Glu Ala Ser Phe Thr Thr Leu Ala Asp
            340             345             350
Val Asp Lys Glu Ser Leu Leu Lys Glu Leu Lys Ile Ser Thr Asp Ser
            355             360             365
Lys Glu Ala Val Ala Ile Thr Asp Ile Thr Leu Asp Glu Lys Thr His
            370             375             380
Lys Ala Val Ile Thr Gly Asp Phe Ser Gln Ala Val Ala Thr Tyr Thr
385             390             395             400
Val Thr Phe His His Glu Ser Phe Gln Ala Arg Pro Asn Trp Gln Tyr
            405             410             415
Lys Asp Ser Leu Tyr Ala Tyr Asp Gly Glu Leu Gly Leu Glu Pro Gly
            420             425             430
```